(12) United States Patent
Reuzeau et al.

(10) Patent No.: US 8,119,858 B2
(45) Date of Patent: Feb. 21, 2012

(54) PLANT YIELD IMPROVEMENT BY STE20-LIKE GENE EXPRESSION

(75) Inventors: Christophe Reuzeau, La Chapelle Gonaguet (FR); Ana Isabel Sanz Molinero, Gentbrugge (BE)

(73) Assignee: CropDesign N.V. (BE)

( * ) Notice: Subject to any disclaimer, the term of this patent is extended or adjusted under 35 U.S.C. 154(b) by 122 days.

(21) Appl. No.: 11/988,254

(22) PCT Filed: Jul. 6, 2006

(86) PCT No.: PCT/EP2006/063976
§ 371 (c)(1),
(2), (4) Date: Jan. 23, 2008

(87) PCT Pub. No.: WO2007/003660
PCT Pub. Date: Jan. 11, 2007

(65) Prior Publication Data
US 2009/0025101 A1    Jan. 22, 2009

Related U.S. Application Data

(60) Provisional application No. 60/697,338, filed on Jul. 8, 2005.

(30) Foreign Application Priority Data

Jul. 6, 2005  (EP) ..................................... 05106135

(51) Int. Cl.
| | | |
|---|---|---|
| C12N 15/82 | (2006.01) | |
| A01H 5/00 | (2006.01) | |
| A01H 5/10 | (2006.01) | |
| A23K 1/00 | (2006.01) | |
| A23L 1/00 | (2006.01) | |

(52) U.S. Cl. ..... 800/290; 800/298; 800/320; 800/320.1; 800/320.2; 800/320.3; 426/615

(58) Field of Classification Search .................. None
See application file for complete search history.

(56) References Cited

U.S. PATENT DOCUMENTS

| | | | |
|---|---|---|---|
| 5,912,415 A | 6/1999 | Olszewski et al. | |
| 6,504,083 B1 | 1/2003 | Barbour et al. | |
| 6,613,959 B1 * | 9/2003 | Sheen et al. | 800/278 |
| 2004/0172685 A1 | 9/2004 | Mundy et al. | |
| 2006/0150283 A1 * | 7/2006 | Alexandrov et al. | 800/288 |

FOREIGN PATENT DOCUMENTS

WO    WO-97/43419 A2    11/1997

OTHER PUBLICATIONS

Leprince A. et al. Molecular characterisation of plant cDNAs BnMAP4Kalpha1 and BnMAP4Kalpha2 belonging to the GCK/SPS1 subfamily of MAP kinase kinase kinase kinase. Biochim Biophys Acta. Jan. 18, 1999;1444(1):1-13.* de Pater B.S. et al. The promoter of the rice gene GOS2 is active in various different monocot tissues and binds rice nuclear factor ASF-1. Plant J. Nov. 1992;2(6):837-44.*

Dan et al. The Ste20 group kinases as regulators of MAP kinase cascades Trends Cell Biol. May 2001;11(5):220-30.*

Riou-Khamlichi C et al. Cytokinin activation of *Arabidopsis* cell division through a D-type cyclin. Science. Mar. 5, 1999;283(5407):1541-4.*

Cockcroft CE et al. Cyclin D control of growth rate in plants. Nature. Jun. 1, 2000;405(6786):575-9.*

Kano-Murakami Y. et al. A rice homeotic gene, OSH1, causes unusual phenotypes in transgenic tobacco. FEBS Lett. Nov. 22, 1993;334(3):365-8.*

Kronberg et al. The silver lining of a viral agent: increasing seed yield and harvest index in *Arabidopsis* by ectopic expression of the potato leaf roll virus movement protein. Plant Physiol. Nov. 2007; 145(3):905-18.*

Leprince, A.-S., et al., "Molecular characterisation of plant cDNAs *BnMAP4Kα1* and BnMAP4Kα2 belonging to the GCK/SPS1 subfamily of MAP kinase kinase kinase kinase", Biochemica et Biophysica Acta, 1999, vol. 1444, pp. 1-13.

Mayer, K., et al., "Sequence and analysis of chromosome 4 of the plant *Arabidopsis thaliana*", Nature, 1999, vol. 402, pp. 769-777.

"Kinase like protein", Database EMBL-EBI, Accession No. 023304, Jan. 1, 1998.

Assem, S.K., et al., "Comparison of the Efficiency of Some Novel Maize Promoters in Monocot and Dicot Plants", Arab J. Biotech., vol. 5, No. 1, (2002), pp. 57-66.

Gaborit, C., et al., "Molecular Cloning of a Full-Length cDNA and Gene from *Coffea arabica* Encoding a Protein Homologous to the Yeast Translation Initiation Factor SUI1: Expression Analysis in Plant Organs", Braz. J. Plant Physiol., vol. 15, No. 1, (2003), pp. 55-58.

Marraccini, P., et al., "Update on Coffee Biochemical Compounds, Protein and Gene Expression during Bean Maturation and in other Tissues", Proceedings of the 19th International Scientific Colloquium on Coffee, May 14-18, 2001, Trieste, Italy. Ed. ASIC., Paris, France, (2001), 12 pp.

"*Arabidopsis thaliana* DNA chromosome 4, ESSA I FCA contig fragment No. 1", Database EMBL Accession No. Z97336, Jul. 4, 1997.

English Translation of Chinese Office Action for Chinese Patent Application for Invention No. 2006800323571, (2010), pp. 1-4.

* cited by examiner

*Primary Examiner* — Cynthia Collins
(74) *Attorney, Agent, or Firm* — Connolly Bove Lodge & Hutz LLP

(57) ABSTRACT

The present invention concerns a method for increasing plant yield by modulating expression in a plant of a nucleic acid encoding a Ste20-like polypeptide or a homologue thereof. One such method comprises introducing into a plant a Ste20-like nucleic acid or variant thereof. The invention also relates to transgenic plants having introduced therein a Ste20-like nucleic acid or variant thereof, which plants have increased yield relative to control plants. The present invention also concerns constructs useful in the methods of the invention.

22 Claims, 19 Drawing Sheets

SEQ ID NO: 1, Ste20-like coding sequence, start and stop codon in bold

CATAACAATTCAATAAGCAAGAGTGTACTCATCTTCTTTCTATTTATGGCTCGGAACAAGCT
CGAGTTCCCTCTTGATGCTGAAGCCTACGAGATCATCTGCAAGATAGGCGTTGGTGTTAGTG
CTTCGGTCTACAAGGCCATATGCATTCCGATGAACTCAATGGTAGTTGCTATCAAAGCCATC
GATCTTGATCAGTCGCGGGCTGACTTTGACAGTCTTCGCCGTGAAACCAAGACGATGTCTCT
GCTTTCTCATCCGAATATTCTCAATGCTTATTGTTCATTCACCGTTGATCGATGTCTCTGGG
TGGTTATGCCATTCATGTCTTGTGGCTCTCTTCATTGATCGTCTCTTCGTCTTTTCCAAGT
GGGTTACCAGAAAACTGCATTTCCGTCTTCCTCAAGGAAACTCTGAATGCAATCTCGTATCT
TCACGATCAGGGTCATTTGCACCGTGACATCAAGGCAGGTAACATTCTGGTAGATTCTGATG
GATCCGTGAAGCTCGCTGATTTCGGAGTATCTGCATCCATCTATGAACCCGTGACATCTTCC
TCTGGAACAACATCTTCTTCTTTAAGGTTAACTGATATAGCGGGAACACCGTATTGGATGGC
TCCGGAAGTGGTTCATTCCCACACAGGGTATGGTTTCAAAGCAGACATTTGGTCTTTCGGGA
TAACAGCGTTGGAGTTAGCACATGGAAGACCTCCGTTATCTCACTTACCGCCGTTGAAGAGT
CTGCTCATGAAGATCACCAAAAGGTTTCATTTTTCTGATTACGAGATCAATACGAGCGGAAG
CAGCAAAAAGGGTAACAAGAAGTTCTCAAAAGCTTTTAGAGAAATGGTTGGTTTGTGTCTAG
AGCAAGATCCTACTAAAAGACCATCGGCAGAGAAGTTGTTGAAGCATCCTTTTTTCAAGAAC
TGTAAAGGACTCGACTTTGTGGTCAAGAACGTGTTGCATAGCTTGTCAAACGCAGAGCAGAT
GTTTATGGAGAGTCAGATTTTGATCAAGAGTGTTGGAGATGATGATGAAGAAGAAGAAGAAG
AAGACGAAGAGATAGTGAAGAATAGAAGAATCAGTGGGTGGAATTTCCGTGAAGACGATCTC
CAACTTAGTCCAGTGTTCCCAGCTACTGAATCAGACTCTTCTGAGTCCAGTCCACGTGAAGA
AGATCAATCAAAAGACAAAAAGGAAGACGATAACGTCACAATAACGGGGTATGAACTCGGTT
TAGGTTTGTCGAACGAGGAAGCTAAGAACCAAGAAGGTGAGGTTGTTGGGTTTGATAAAGAT
TTGGTGTTAGAGAAACTGAAAGTGTTGAAGAAAAGTTTAGAGCATCAAAGAGCAAGAGTGTC
GATTATAATCGAAGCATTGAGTGGGGACAAGGAAGAGAAGAGCAGAGAAGAAGAGCTTCTAG
AGATGGTGGAGAAGTTAAAGATTGAATTGGAAACTGAGAAGCTAAAGACCTTGCGTGCTGAT
AAAGATAGTGTTTTGGGTTAACTATTCTAAACTTGTTAATATTTTTTTCTATATGCTAAAA
TTAT

SEQ ID NO: 2, Ste20-like deduced protein sequence

MARNKLEFPLDAEAYEIICKIGVGVSASVYKAICIPMNSMVVAIKAIDLDQSRADFDSLRRE
TKTMSLLSHPNILNAYCSFTVDRCLWVVMPFMSCGSLHSIVSSSFPSGLPENCISVFLKETL
NAISYLHDQGHLHRDIKAGNILVDSDGSVKLADFGVSASIYEPVTSSSGTTSSSLRLTDIAG
TPYWMAPEVVHSHTGYGFKADIWSFGITALELAHGRPPLSHLPPLKSLLMKITKRFHFSDYE
INTSGSSKKGNKKFSKAFREMVGLCLEQDPTKRPSAEKLLKHPFFKNCKGLDFVVKNVLHSL
SNAEQMFMESQILIKSVGDDDEEEEEDEEIVKNRRISGWNFREDDLQLSPVFPATESDSSE
SSPREEDQSKDKKEDDNVTITGYELGLGLSNEEAKNQEGEVVGFDKDLVLEKLKVLKKSLEH
QRARVSIIIEALSGDKEEKSREEELLEMVEKLKIELETEKLKTLRADKDSVLG

SEQ ID NO: 3, prm03186; start codon in bold, AttB1 site in italics

*GGGGACAAGTTTGTACAAAAAAGCAGGCTTCAC*AATGGCTCGGAACAAGCTC

FIGURE 3

SEQ ID NO: 4, prm03187

*GGGGACCACTTTGTACAAGAAAGCTGGGT*AATAGTTAACCCAAAACACTATCTTTA

**SEQ ID NO: 5, Expression cassette p*GOS2*::*Ste20-like***

AATCCGAAAAGTTTCTGCACCGTTTTCACCCCCTAACTAACAATATAGGGAACGTGTGCTAA
ATATAAAATGAGACCTTATATATGTAGCGCTGATAACTAGAACTATGCAAGAAAAACTCATC
CACCTACTTTAGTGGCAATCGGGCTAAATAAAAAAGAGTCGCTACACTAGTTTCGTTTTCCT
TAGTAATTAAGTGGGAAAATGAAATCATTATTGCTTAGAATATACGTTCACATCTCTGTCAT
GAAGTTAAATTATTCGAGGTAGCCATAATTGTCATCAAACTCTTCTTGAATAAAAAAATCTT
TCTAGCTGAACTCAATGGGTAAAGAGAGAGATTTTTTTTAAAAAAATAGAATGAAGATATTC
TGAACGTATTGGCAAAGATTTAAACATATAATTATATAATTTTATAGTTTGTGCATTCGTCA
TATCGCACATCATTAAGGACATGTCTTACTCCATCCCAATTTTTATTTAGTAATTAAAGACA
ATTGACTTATTTTTATTATTTATCTTTTTTCGATTAGATGCAAGGTACTTACGCACACACTT
TGTGCTCATGTGCATGTGTGAGTGCACCTCCTCAATACACGTTCAACTAGCAACACATCTCT
AATATCACTCGCCTATTTAATACATTTAGGTAGCAATATCTGAATTCAAGCACTCCACCATC
ACCAGACCACTTTTAATAATATCTAAAATACAAAAAATAATTTTACAGAATAGCATGAAAAG
TATGAAACGAACTATTTAGGTTTTTCACATACAAAAAAAAAAAGAATTTTGCTCGTGCGCGA
GCGCCAATCTCCCATATTGGGCACACAGGCAACAACAGAGTGGCTGCCCACAGAACAACCCA
CAAAAAACGATGATCTAACGGAGGACAGCAAGTCCGCAACAACCTTTTAACAGCAGGCTTTG
CGGCCAGGAGAGAGGAGGAGAGGCAAAGAAAACCAAGCATCCTCCTCCTCCCATCTATAAAT
TCCTCCCCCCTTTTCCCCTCTCTATATAGGAGGCATCCAAGCCAAGAAGAGGGAGAGCACCA
AGGACACGCGACTAGCAGAAGCCGAGCGACCGCCTTCTTCGATCCATATCTTCCGGTCGAGT
TCTTGGTCGATCTCTTCCCTCCTCCACCTCCTCCTCACAGGGTATGTGCCCTTCGGTTGTTC
TTGGATTTATTGTTCTAGGTTGTGTAGTACGGGCGTTGATGTTAGGAAAGGGGATCTGTATC
TGTGATGATTCCTGTTCTTGGATTTGGGATAGAGGGGTTCTTGATGTTGCATGTTATCGGTT
CGGTTTGATTAGTAGTATGGTTTTCAATCGTCTGGAGAGCTCTATGGAAATGAAATGGTTTA
GGGTACGGAATCTTGCGATTTTGTGAGTACCTTTTGTTTGAGGTAAAATCAGAGCACCGGTG
ATTTTGCTTGGTGTAATAAAAGTACGGTTGTTTGGTCCTCGATTCTGGTAGTGATGCTTCTC
GATTTGACGAAGCTATCCTTTGTTTATTCCCTATTGAACAAAAATAATCCAACTTTGAAGAC
GGTCCCGTTGATGAGATTGAATGATTGATTCTTAAGCCTGTCCAAAATTTCGCAGCTGGCTT
GTTTAGATACAGTAGTCCCCATCACGAAATTCATGGAAACAGTTATAATCCTCAGGAACAGG
GGATTCCCTGTTCTTCCGATTTGCTTTAGTCCCAGAATTTTTTTCCCAAATATCTTAAAAA
GTCACTTTCTGGTTCAGTTCAATGAATTGATTGCTACAAATAATGCTTTTATAGCGTTATCC
TAGCTGTAGTTCAGTTAATAGGTAATACCCCTATAGTTTAGTCAGGAGAAGAACTTATCCGA
TTTCTGATCTCCATTTTAATTATATGAAATGAACTGTAGCATAAGCAGTATTCATTTGGAT
TATTTTTTTTATTAGCTCTCACCCCTTCATTATTCTGAGCTGAAAGTCTGGCATGAACTGTC
CTCAATTTTGTTTTCAAATTCACATCGATTATCTATGCATTATCCTCTTGTATCTACCTGTA
GAAGTTTCTTTTTGGTTATTCCTTGACTGCTTGATTACAGAAAGAAATTTATGAAGCTGTAA
TCGGGATAGTTATACTGCTTGTTCTTATGATTCATTTCCTTTGTGCAGTTCTTGGTGTAGCT
TGCCACTTTCACCAGCAAAGTTCATTTAAATCAACTAGGGATATCACAAGTTTGTACAAAAA
AGCAGGCTTCACATGGCTCGGAACAAGCTCGAGTTCCCTCTTGATGCTGAAGCCTACGAGA
TCATCTGCAAGATAGGCGTTGGTGTTAGTGCTTCGGTCTACAAGGCCATATGCATTCCGATG

FIGURE 3 (continued)

```
AACTCAATGGTAGTTGCTATCAAAGCCATCGATCTTGATCAGTCGCGGGCTGACTTTGACAG
TCTTCGCCGTGAAACCAAGACGATGTCTCTGCTTTCTCATCCGAATATTCTCAATGCTTATT
GTTCATTCACCGTTGATCGATGTCTCTGGGTGGTTATGCCATTCATGTCTTGTGGCTCTCTT
CATTCGATCGTCTCTTCGTCTTTTCCAAGTGGGTTACCAGAAAACTGCATTTCCGTCTTCCT
CAAGGAAACTCTGAATGCAATCTCGTATCTTCACGATCAGGGTCATTTGCACCGTGACATCA
AGGCAGGTAACATTCTGGTAGATTCTGATGGATCCGTGAAGCTCGCTGATTTCGGAGTATCT
GCATCCATCTATGAACCCGTGACATCTTCCTCTGGAACAACATCTTCTTCTTTAAGGTTAAC
TGATATAGCGGGAACACCGTATTGGATGGCTCCGGAAGTGGTTCATTCCCACACAGGGTATG
GTTTCAAAGCAGACATTTGGTCTTTCGGGATAACAGCGTTGGAGTTAGCACATGGAAGACCT
CCGTTATCTCACTTACCGCCGTTGAAGAGTCTGCTCATGAAGATCACCAAAAGGTTTCATTT
TTCTGATTACGAGATCAATACGAGCGGAAGCAGCAAAAAGGGTAACAAGAAGTTCTCAAAAG
CTTTTAGAGAAATGGTTGGTTTGTGTCTAGAGCAAGATCCTACTAAAAGACCATCGGCAGAG
AAGTTGTTGAAGCATCCTTTTTTCAAGAACTGTAAAGGACTCGACTTTGTGGTCAAGAACGT
GTTGCATAGCTTGTCAAACGCAGAGCAGATGTTTATGGAGAGTCAGATTTTGATCAAGAGTG
TTGGAGATGATGATGAAGAAGAAGAAGAAGAAGACGAAGAGATAGTGAAGAATAGAAGAATC
AGTGGGTGGAATTTCCGTGAAGACGATCTCCAACTTAGTCCAGTGTTCCCAGCTACTGAATC
AGACTCTTCTGAGTCCAGTCCACGTGAAGAAGATCAATCAAAAGACAAAAAGGAAGACGATA
ACGTCACAATAACGGGGTATGAACTCGGTTTAGGTTTGTCGAACGAGGAAGCTAAGAACCAA
GAAGGTGAGGTTGTTGGGTTTGATAAAGATTTGGTGTTAGAGAAACTGAAAGTGTTGAAGAA
AAGTTTAGAGCATCAAAGAGCAAGAGTGTCGATTATAATCGAAGCATTGAGTGGGGACAAGG
AAGAGAAGAGCAGAGAAGAAGAGCTTCTAGAGATGGTGGAGAAGTTAAAGATTGAATTGGAA
ACTGAGAAGCTAAAGACCTTGCGTGCTGATAAAGATAGTGTTTTGGGTAAC
```

SEQ ID NO: 6, Ste20 signature sequence

G(T/N)P(Y/C/R)(W/R)MAPE(V/K)

SEQ ID NO: 7, consensus sequence

(S/H/N)(I/L)(V/I/L/M)(S/K)(S/H/T/A/I/V)(S/G/V/A)(F/Y)(P/Q)(S/N/D/E)G

SEQ ID NO: 8, consensus sequence

(V/I)HSH(T/N/V)GY(G/S)(F/I)

SEQ ID NO: 9, consensus sequence

RPPLSHLPP(L/S)KS

SEQ ID NO: 10, consensus sequence

RRISGWNF

FIGURE 3 (continued)

SEQ ID NO: 11, At5g14720 coding sequence

```
CAGACGACAGAAAAGCTAACCACAAGAGGAGGAGAGAAACTCGATAACAAACAAGAGAAAGA
GAAAGCGAGATTCTAAAATCTAATCTCGTGCTTCCAATTCAAATAATTTTGTCTCCTTAGCG
GATCGATCGTAGATTATAAAGCTCCGCCGTCGCCTCCGCCGCAATCGACGGCGGTGTCTACG
TCGCTTTCGTTTCGTGCGTAACAGGAGGAGCAGCAGCAAAATAAGTCAGCTTAAGTAACGCC
GTCTTTGATTTGACTTGAGATAAGTATTTTGGTGATATGGCATTGATGATGTTTCCGCATTT
GCTCGACGTTGACGAAAAGTAAAATGCTGGCGAATTGGAAGAAACCACATACAGATTGATGC
TCTCTTCAGTCGACCTCTTTTGTAAATTTGTTGAAACTTACGGGGTCGAAGGTGTGTAGCAT
ATATGCTATAAGAAGATTATAAAGTAAAAATTATGGAATCGGGTTCAGAGAAAAAGTTCCCT
CTCAATGCAAAAGACTACAAGTTATATGAAGAAATTGGAGATGGTGTCAGTGCGACTGTGCA
TAGAGCTTTGTGTATACCGCTTAATGTGGTAGTTGCTATCAAGGTTCTTGATCTGGAAAAGT
GCAACAACGATCTGGATGGGATCCGGAGAGAGGTGCAAACAATGAGTCTGATCAACCATCCA
AATGTGTTGCAAGCTCATTGCTCATTTACCACCGGACACCAGCTTTGGGTTGTGATGCCTTA
CATGGCTGGAGGATCTTGTCTCCATATAATTAAGTCTTCCTATCCAGATGGATTTGAGGAAC
CTGTTATCGCTACTTTACTTCGTGAGACTCTGAAAGCTCTTGTATATCTTCATGCTCATGGG
CATATCCACAGGGATGTGAAGGCTGGAAACATTTTATTGGATTCCAATGGTGCCGTTAAGTT
AGCAGACTTTGGAGTATCAGCTTGCATGTTTGATACGGGAGATAGACAACGTTCCAGAAATA
CATTTGTTGGGACTCCATGCTGGATGGCTCCTGAAGTCATGCAGCAACTACATGGATATGAT
TTCAAAGCAGATGTATGGTCATTTGGAATAACAGCACTTGAATTGGCACATGGTCATGCCCC
ATTTTCCAAATATCCGCCAATGAAGGTTTTGCTGATGACCTTACAAAATGCACCTCCTGGAC
TTGACTACGAGAGAGACAAAAGATTCTCGAAAGCCTTCAAGGAAATGGTGGGTACATGCCTG
GTGAAGGACCCAAAGAAGCGTCCAACTTCAGAAAAGCTTTTGAAACACCCTTTCTTCAAACA
TGCACGTCCAGCTGATTACCTGGTTAAAACAATTCTAAATGGTCTTCCTCCATTAGGTGATC
GCTATAGACAAATAAAGTCGAAGGAAGCTGATCTCCTAATGCAAAACAAATCTGAATATGAA
GCGCACTTATCACAGCAAGAGTATATAAGGGGAATAAGCGCTTGGAATTTCAATCTCGAGGA
CCTAAAAACTCAAGCTGCCCTTATTTCAGATGATGATACTTCACATGCTGAAGAGCCCGATT
TCAACCAAAAGCAATGTGAAAGACAGGATGAATCTGCTCTTTCCCCTGAAAGGGCTAGCAGC
TCAGCAACAGCTCCTAGTCAAGATGACGAACTGAATGATATTCATGATTTAGAGAGTTCTTT
CGCCTCATTTCCAATCAAACCTCTTCAAGCACTAAAAGGCTGCTTTGATATCAGTGAGGACG
AGGATAATGCAACTACTCCTGATTGGAAAGATGCTAATGTAAATTCTGGACAACAGCTTTTA
ACAAAGGCTTCCATTGGATCTTTGGCCGAAACCACGAAAGAAGAGGACACTGCAGCACAAAA
CACTTCTTTACCACGTCATGTCATTTCTGAACAGAAAAAATATTTGAGCGGTTCAATTATAC
CAGAGAGTACTTTCTCTCCAAAAAGAATCACATCTGATGCTGATAGGGAGTTTCAACAGCGT
AGATATCAAACAGAGCGGAGCTACAGCGGATCATTATACCGCACCAAGAGAGATTCCGTGGA
CGAGACGTCAGAAGTCCCGCATGTGGAGCACAAGGGACGGTTTAAGGTCACATCAGCAGATC
TGAGTCCCAAGGGATCTACAAACTCTACATTCACACCATTTAGTGGTGGTACAAGCAGCCCT
AGTTGCCTCAATGCTACAACCGCCTCAATCCTCCCATCAATTCAGTCGATTTTGCAGCAAAA
TGCTATGCAACGGGAAGAGATTTTGAGACTAATCAAATACTTGGAGCAAACCTCTGCCAAGC
AACCTGGATCGCCTGAGACGAACGTCGATGACCTATTGCAGACGCCTCCTGCAACCTCACGA
GAGAGAGAACTTCAGTCTCAAGTCATGCTACTACAACAAAGCTTTTCCAGCCTAACAGAAGA
ACTAAAGAAACAGAAGCAGAAAATGGGCAGTTGGAGAATCAGTTGAACGCATTAACACACA
GAAATGATTGAGTCTCAAAAGCCATCGAGACAAGGCTGAGAGATACAACTGGGATCTTGAG
TTAAAAAAACACAAAATTCCCTTTCAAGGCAAAAGAAGAAATAGAGAAGATTTGTGTGCTT
TATATTTCTATTGGGTGTAATTTGTTTGACAGGTTTATATTATGTGACAACTACTACAGTGA
TTTTCTTATTTTTGGGGAAGTTTTCCCCACTTTTCTTTTTTACTTATTTGTGTTTTATGATA
TGCTATGTAAACAAAATACTATTGTTTAATTATGTTTCTGTGTG
```

FIGURE 3 (continued)

SEQ ID NO: 12, At5g14720 deduced protein sequence

MESSSEKKFPLNAKDYKLYEEIGDGVSATVHRALCIPLNVVVAIKVLDLEKCNNDLDGIRRE
VQTMSLINHPNVLQAHCSFTTGHQLWVVMPYMAGGSCLHIIKSSYPDGFEEPVIATLLRETL
KALVYLHAHGHIHRDVKAGNILLDSNGAVKLADFGVSACMFDTGDRQRSRNTFVGTPCWMAP
EVMQQLHGYDFKADVWSFGITALELAHGHAPFSKYPPMKVLLMTLQNAPPGLDYERDKRFSK
AFKEMVGTCLVKDPKKRPTSEKLLKHPFFKHARPADYLVKTILNGLPPLGDRYRQIKSKEAD
LLMQNKSEYEAHLSQQEYIRGISAWNFNLEDLKTQAALISDDDTSHAEEPDFNQKQCERQDE
SALSPERASSSATAPSQDDELNDIHDLESSFASFPIKPLQALKGCFDISEDEDNATTPDWKD
ANVNSGQQLLTKASIGSLAETTKEEDTAAQNTSLPRHVISEQKKYLSGSIIPESTFSPKRIT
SDADREFQQRRYQTERSYSGSLYRTKRDSVDETSEVPHVEHKGRFKVTSADLSPKGSTNSTF
TPFSGGTSSPSCLNATTASILPSIQSILQQNAMQREEILRLIKYLEQTSAKQPGSPETNVDD
LLQTPPATSRERELQSQVMLLQQSFSSLTEELKKQKQKNGQLENQLNALTHRND

SEQ ID NO: 13, At1g70430 coding sequence

ATGGCTGGTTCATCAACGAAACGATTTCCTCTATATGCTAAAGATTATGAGCTCTTTGAAGA
GGTAGGAGAAGGTGTTAGTGCTACTGTGTATAGAGCTCGTTGCATTGCTCTTAACGAGATTG
TCGCTGTTAAAATCTTGGATCTCGAAAAATGCAGGAATGATTTGGAAACAATACGCAAGGAA
GTTCATATAATGAGTTTGATTGATCATCCGAATTTATTGAAAGCGCATTGTTCGTTTATCGA
CAGTAGTAGTTTGTGGATTGTAATGCCTTATATGTCGGGTGGTTCTTGTTTTCATTTAATGA
AATCTGTATATCCGGAAGGTCTTGAGCAACCTATAATTGCTACTTTGTTGAGGGAAGTGCTT
AAAGCTCTTGTTTATCTTCATAGACAAGGTCACATCCATAGAGATGTTAAGGCTGGGAATAT
ATTGATTCACTCAAAAGGCGTAGTTAAACTTGGAGACTTTGGAGTTTCAGCATGTATGTTTG
ATAGTGGAGAAAGAATGCAAACAAGGAATACATTCGTTGGGACTCCTTGTTGGATGGCACCT
GAGGTTATGCAGCAACTAGATGGATATGATTTCAAGTATCTTGCTCATGGTCATGCCCCATT
TTCCAAATATCCACCTATGAAGGTGCTACTAATGACATTACAAAATGCACCTCCTCGTCTAG
ACTATGACAGAGATAAGAAATTCTCAAAGTCATTTAGAGAGTTAATCGCAGCGTGCTTAGTT
AAAGATCCGAAAAAGCGTCCAACTGCAGCAAAACTTCTGAAACATCCTTTCTTCAAACATGC
TCGGTCTACAGATTATTTGTCCCGTAAAATTCTTCATGGTCTTTCTCCACTTGGTGAACGTT
TTAAAAAGCTCAAGGAGGCAGAGGCTGAGTTGTTCAAAGGCATAAATGGTGACAAAGAACAG
TTGTCTCAGCATGAGTATATGAGAGGAATTAGTGCTTGGAACTTTGATCTTGAAGCATTGAG
AAGGCAGGCATCACTTGTAATTATTCCAAATGAAGAAATCTATAATTCAGAGATACAGGAAC
TGAACAGAAATGGAGATGTACCAAAAGGAAAACCAGTGATACAAAGGTCACAGACTATGCCT
TTGGAATATTTCTCAGAAAAGGCAAGTGATATGGTGAGTGAGAGTAGCAGTCAATTAACCGG
TTCATTACTTCCTTCGTTTCATCGCAAATTCCTCCCGGCTCTTGGCAATGCATGTAACTCGA
GCGATAGAGCAGCAGAGAAGCTCGCTTTTGAAGAGCCACGTCAAGTACTACACCCATTAGCG
GATACAAAGAAAATTAGAAAAGCAGGAAGTGATCAGCAGGAGAAACCAAAAAATGGTTACGC
AGATAGTCCTGTGAACCGTGAATCTTCCACATTATCAAAGGAACCATTAGCGGATACAAAGC
AAGTTAGAAAACCAGGAAATGAGCAGGAGAAACCAAAAAACGGCTATATAGTTAGTCATGTG
AACCGTGAATCTTCCACATCAGAGGAAATCCTCCCACTGTTGCAGAGTCTCCTGGTTCAGAA
TGACATTCAAAGGGCGCAAGTAATCAGGTTAATTAGATTTTTTGATCGAACTGCGAAAACGG
AAAATCCAATCTCAAAAACCGAAGGAGTGCAGGAGAAAGATCTGCAATCTCAAGTTCAGTTT
TTGGAGCAAAGTGTTGAGAAGCTTGTAGAGGAAGTTCAGAGAAGAAAGATATAAATAGTCA
GCTAGAGCAACAGATCAGCTCTCTGATTAGCAGCAACAACATCTCTTAA

FIGURE 3 (continued)

SEQ ID NO: 14, At1g70430 deduced protein sequence

MAGSSTKRFPLYAKDYELFEEVGEGVSATVYRARCIALNEIVAVKILDLEKCRNDLETIRKE
VHIMSLIDHPNLLKAHCSFIDSSSLWIVMPYMSGGSCFHLMKSVYPEGLEQPIIATLLREVL
KALVYLHRQGHIHRDVKAGNILIHSKGVVKLGDFGVSACMFDSGERMQTRNTFVGTPCWMAP
EVMQQLDGYDFKYLAHGHAPFSKYPPMKVLLMTLQNAPPRLDYDRDKKFSKSFRELIAACLV
KDPKKRPTAAKLLKHPFFKHARSTDYLSRKILHGLSPLGERFKKLKEAEAELFKGINGDKEQ
LSQHEYMRGISAWNFDLEALRRQASLVIIPNEEIYNSEIQELNRNGDVPKGKPVIQRSQTMP
LEYFSEKASDMVSESSSQLTGSLLPSFHRKFLPALGNACNSSDRAAEKLAFEEPRQVLHPLA
DTKKIRKAGSDQQEKPKNGYADSPVNRESSTLSKEPLADTKQVRKPGNEQEKPKNGYIVSHV
NRESSTSEEILPLLQSLLVQNDIQRAQVIRLIRFFDRTAKTENPISKTEGVQEKDLQSQVQF
LEQSVEKLVEEVQRRKDINSQLEQQISSLISSNNIS

SEQ ID NO: 15, At1g23700 coding sequence

ATGACGAGTTCACCGGAAACGAGATTTCCTCTGGTTGCGAAAGATTACGAGATTTTAGAAGA
GATAGGCGATGGTGTTTACAGAGCTCGATGCATTCTACTTGATGAAATTGTAGCCATCAAGA
TCTGGAACCTTGAAAAATGCACCAACGATCTGGAAACCATAAGGAAAGAAGTTCATAGATTG
AGCTTAATTGATCATCCAAATCTATTGAGGGTGCATTGCTCTTTCATAGATAGTAGCAGCTT
GTGGATTGTGATGCCTTTTATGTCGTGCGGCTCTTCCTTGAACATAATGAAATCAGTCTATC
CAAATGGTCTTGAGGAACCTGTAATTGCTATATTGTTGCGGGAGATTCTTAAAGCTCTTGTT
TACCTTCATGGACTAGGACACATCCATCGAAATGTTAAGGCTGGGAATGTACTGGTTGACTC
AGAAGGAACTGTTAAGCTCGGTGACTTTGAAGTTTCAGCATCCATGTTTGATAGTGTGGAAA
GGATGCGTACTAGTTCTGAGAATACTTTTGTTGGAAATCCACGCCGGATGGCACCTGAGAAG
GATATGCAGCAAGTTGATGGCTATGATTTCAAAGTGGATATCTGGTCGTTTGGCATGACTGC
CCTGGAACTTGCCCATGGTCATTCACCTACCACGGTGCTACCATTGAACTTACAAAATTCTC
CCTTTCCTAACTATGAAGAAGACACGAAATTCTCTAAGTCTTTTAGAGAGTTGGTCGCAGCT
TGCTTGATAGAAGATCCAGAAAAACGTCCGACCGCTTCACAACTACTGGAATATCCGTTCTT
ACAGCAAACTCTTTCTACTGAATACTTGGCTAGTACATTTCTTGATGGCCTCTCTCCGCTTG
GTGAGCGTTATAGAAAGCTGAAGGAGGAAAAGGCCAAGTTGGTTAAAGGTGTAGATGGTAAC
AAGGAGAAAGTATCTCAGGAAAATGTTGAAGCGCTGCTGATGGAACCTGCTAGTCTTGTGAA
CCCTGTTTCTTGTGATACTGCTCAAGTCCTCCCAATCTTACAGAATATCCTGATCCAAAATG
ATATCCAAAGGGAAAATGTTGAAGCGCTGCTGACGGAACCTGCTATTCTTGTGAACCCTGTT
TCTTGTGATACTGCTCAAGTCCTCCCAATCGTACAGAATATCCTGATCCAGAATGATATCCA
AAGGAAAAGGTTAATCGGTTTAATGCAACTCTGTGATCCAACTGCTGGTAAGTTTGCTGTTC
TATCACTAGAATTTGCATCTTCTCTATGTTACAAGTTCCATGACCTGATCTTGATTTTTGTA
CAGAAATCAGAATTCCGATTGGCAATACAGAAGTTGGGCAGATATCAACAACAGAGACAGAT
CTATTGTCTGAGGTTCACGTTTTGCAGCAGAGGTAATGATAAATTCCACAAGCTTTAA

FIGURE 3 (continued)

SEQ ID NO: 16, At1g23700 deduced protein sequence

MTSSPETRFPLVAKDYEILEEIGDGVYRARCILLDEIVAIKIWNLEKCTNDLETIRKEVHRL
SLIDHPNLLRVHCSFIDSSSLWIVMPFMSCGSSLNIMKSVYPNGLEEPVIAILLREILKALV
YLHGLGHIHRNVKAGNVLVDSEGTVKLGDFEVSASMFDSVERMRTSSENTFVGNPRRMAPEK
DMQQVDGYDFKVDIWSFGMTALELAHGHSPTTVLPLNLQNSPFPNYEEDTKFSKSFRELVAA
CLIEDPEKRPTASQLLEYPFLQQTLSTEYLASTFLDGLSPLGERYRKLKEEKAKLVKGVDGN
KEKVSQENVEALLMEPASLVNPVSCDTAQVLPILQNILIQNDIQRENVEALLTEPAILVNPV
SCDTAQVLPIVQNILIQNDIQRKRLIGLMQLCDPTAGKFAVLSLEFASSLCYKFHDLILIFV
QKSEFRLAIQKLGRYQQQRQIYCLRFTFCSRGNDKFHKL

SEQ ID NO: 17, At1g79640 coding sequence

ATGGAGAAGAAGAAGTATCCAATTGGACCAGAGCATTATACTCTCTACGAGTTTATTGGACA
AGGTGTTAGTGCTCTAGTGCATCGTGCTTTGTGCATTCCGTTTGATGAAGTCGTTGCTATTA
AGATTCTTGATTTTGAACGCGATAACTGCGATCTGAACAACATCTCTCGTGAAGCGCAGACG
ATGATGCTTGTTGATCATCCCAATGTGTTGAAGTCACATTGTTCCTTTGTTAGTGATCACAA
TTTGTGGGTCATCATGCCATACATGTCTGGTGGTTCTTGTCTTCACATTCTAAAAGCTGCAT
ATCCTGATGGTTTTGAAGAAGCTATTATAGCTACTATATTGCGTGAAGCTTTGAAGGGATTA
GACTATCTCCATCAGCATGGCCACATTCATCGCGATGTCAAAGCTGGGAATATATTGCTTGG
TGCTCGAGGTGCAGTCAAGTTGGGAGACTTTGGTGTATCTGCCTGTCTCTTTGATTCAGGTG
ATAGGCAACGGACAAGGAACACATTTGTTGGAACACCTTGCTGGATGGCACCTGAAGTCATG
GAGCAGCTACATGGTTATGACTTCAAGGCTGATATTTGGTCGTTTGGTATAACTGGGCTAGA
GCTTGCTCATGGTCACGCTCCTTTCTCTAAATATCCACCAATGAAGGTTCTGCTTATGACGT
TGCAAAATGCACCACCAGGGCTGGATTACGAAAGAGATAAGAAGTTTTCCAGGTCTTTCAAG
CAGATGATCGCCAGTTGTCTAGTTAAAGACCCTTCCAAACGCCCGTCTGCAAAAAAGTTGTT
AAAGCACTCCTTTTTCAAGCAAGCAAGATCAAGCGATTACATTGCACGAAAACTTCTGGATG
GGTTACCAGATCTTGTTAATCGTGTTCAGGCAATAAAGAGAAAGGAAGAAGATATGCTTGCA
CAAGAGAAAATGGCAGATGGAGAAAAGGAAGAATTGTCCCAGCCTTTAAACGCTTGTCATAG
TACCATGCAGAATGAATATAAGAGAGGTATCAGCGGGTGGAATTTCAATCTTGATGATATGA
AAGCCCAGGCTTCATTGATCCAGGACATGGACTGTGGCTTTTCGGACAGTTTATCGGGAAGT
GCAACTTCGTTGCAGGCTCTAGATTCACAGGATACACAATCGGAGATTCAGGAGGATACTGG
TCAAATAACTAATAAGTATCTCCAACCTCTGATTCACCGAAGTCTAAGTATCGCGAGGGATA
AATCTGATGATGATTCAAGTCTTGCCAGCCCCAGTTATGATAGCTACGTATATTCCTCCCCC
CGTCATGAGGATTTATCTTTAAACAATACACATGTTGGTAGTACGCATGCAAACAATGGGAA
ACCAACGGATGCCACATCAATCCCAACCAATCAACCAACAGAGATTATAGCAGGGAGCTCTG
TTTTGGCAGATGGAAATGGTGCTCCCAATAAAGGAGAGAGTGATAAAACTCAAGAACAGCTT
CAAAACGGGTCAAACTGCAATGGGACACATCCTACAGTGGGAGGAGATGACGTACCAACGGA
GATGGCTGTTAAACCACCCAAAGCAGCATCAAGCCTAGATGAATCTGATGACAAATCAAAGC
CGCCAGTTGTGCAGCAAAGAGGGCGTTTTAAAGTAACTTCTGAAAATCTCGACATCGAGAAG
GTGGTGGCGCCTTCGCCAATACTGCAAAAGAGTCACAGCATGCAGGTGCTCTGCCAACATTC
CTCTGCTTCTCTACCTCACTCTGATGTCACATTGCCAAACCTAACCAGCTCATATGTTTACC
CGCTGGTGTATCCAGTTCTGCAAACTAATATTTTGGAAAGGGATAACATTTTGCATATGATG
AAAGTACTCACCAACAGAGAGTTGACAGATGGACGTGCAGTTGAACAAGGAAGTATACAACA
ACCTACTGTGCCCCCAACTGAGAAATCCATGCTTGAAGCAGCACACGAAAGAGAGAAAGAAC
TGCTCCATGACATAACCGACCTGCAATGGAGGCTCATTTGTGCAGAAGAAGAGCTTCAGAAA
TACAAAACCGAACACGCCCAAGTAAGTATGAGTAACTAA

FIGURE 3 (continued)

SEQ ID NO: 18, At1g79640 deduced protein sequence

MEKKKYPIGPEHYTLYEFIGQGVSALVHRALCIPFDEVVAIKILDFERDNCDLNNISREAQT
MMLVDHPNVLKSHCSFVSDHNLWVIMPYMSGGSCLHILKAAYPDGFEEAIIATILREALKGL
DYLHQHGHIHRDVKAGNILLGARGAVKLGDFGVSACLFDSGDRQRTRNTFVGTPCWMAPEVM
EQLHGYDFKADIWSFGITGLELAHGHAPFSKYPPMKVLLMTLQNAPPGLDYERDKKFSRSFK
QMIASCLVKDPSKRPSAKKLLKHSFFKQARSSDYIARKLLDGLPDLVNRVQAIKRKEEDMLA
QEKMADGEKEELSQPLNACHSTMQNEYKRGISGWNFNLDDMKAQASLIQDMDCGFSDSLSGS
ATSLQALDSQDTQSEIQEDTGQITNKYLQPLIHRSLSIARDKSDDDSSLASPSYDSYVYSSP
RHEDLSLNNTHVGSTHANNGKPTDATSIPTNQPTEIIAGSSVLADGNGAPNKGESDKTQEQL
QNGSNCNGTHPTVGGDDVPTEMAVKPPKAASSLDESDDKSKPPVVQQRGRFKVTSENLDIEK
VVAPSPILQKSHSMQVLCQHSSASLPHSDVTLPNLTSSYVYPLVYPVLQTNILERDNILHMM
KVLTNRELTDGRAVEQGSIQQPTVPPTEKSMLEAAHEREKELLHDITDLQWRLICAEEELQK
YKTEHAQVSMSN

SEQ ID NO: 19, At4g10730 coding sequence start and stop codon in bold

GTCACACAAGCCGAATCCAAAAATGTAACAAGAAAAACAAATCTTCACAAGGCAAAAAATCC
AAAATTGAGTTTTTTTTTTCTTCATTTTTTACAATGGTGTCTCGGTTTCGTCTTGCTCTAGA
GGCTGTTTTGGGTTCGAGACGACGTAAGAAGATGGCGAGTACTAGTAGTGGTGGTGGTGGTG
GTGGTGATAAGAAGAAGAAGAAAGGTTTCTCTGTAAACCCTAAAGATTATAAACTTATGGAA
GAAGTTGGATATGGTGCTAGTGCTGTTGTTCATCGTGCTATTTATCTTCCTACTAATGAAGT
TGTTGCTATCAAGTCTTTGGATCTCGATCGCTGCAATAGTAATCTGGATGATATAAGGAGGG
AGGCTCAGACTATGACTTTGATAGACCATCCGAATGTTATAAAGTCGTTTTGTTCGTTTGCT
GTTGATCATCATCTATGGGTCGTTATGCCATTTATGGCTCAGGGTTCGTGTTTGCATCTAAT
GAAAGCAGCGTATCCAGATGGATTTGAAGAGGCGGCTATATGTTCTATGCTGAAAGAAACAC
TTAAAGCTCTTGATTATCTTCATAGACAAGGGCATATCCATCGAGATGTTAAGGCTGGAAAC
ATACTTCTTGATGACACTGGCGAGATTAAGTTAGGTGATTTTGGTGTCTCTGCATGTTTGTT
TGACAATGGCGATAGGCAACGTGCAAGAAATACATTTGTTGGTACTCCATGCTGGATGGCAC
CGGAAGTCTTGCAGCCAGGGAGTGGATACAATTCAAAGGCTGATATATGGTCTTTTGGAATA
ACGGCGCTGGAGTTGGCTCACGGTCATGCACCTTTCTCAAAATATCCCCCTATGAAGGTACT
CTTAATGACTATCCAAAATGCACCACCTGGCCTTGATTATGACCGTGATAAGAAGTTTTCAA
AGTCCTTTAAAGAATTGGTAGCATTGTGTCTGGTGAAAGATCAAACAAAAAGGCCAACTGCT
GAAAAATTGTTGAAACACTCATTTTTCAAGAATGTGAAGCCTCCAGAGATCTGTGTAAAAAA
ATTATTTGTCGATTTACCACCTCTTTGGACTCGCGTAAAAGCTCTTCAGGCCAAGGATGCTG
CACAGCTTGCTTTGAAAGGAATGGCCTCTGCTGACCAGGATGCTATATCACAGAGTGAATAC
CAAAGAGGAGTAAGTGCTTGGAACTTCAATATCGAAGATTTGAAAGAACAAGCATCTTTGCT
AGATGATGATGACATTCTAACAGAGAGTAGGGAAGAAGAAGAATCTTTTGGCGAACAGTTGC
ATAATAAGGCTAGGCAAGTATCTGGTAGTCAATTGCTATCTGAAAACATGAATGGAAAGGAA
AAAGCTTCAGATACTGAGGTGGTAGAACCTATCTGTGAAGAGAAATCCACTCTCAATTCAAC
CACTTCTTCTGTGGAACAACCGGCATCAAGTTCAGAACAAGACGTTCCACAGGCCAAGGGTA
AGCCAGTGAGACTCCAGACTCATAGTGGACCACTTTCATCCGGTGTCGTGTTAATCAATTCA
GACTCAGAGAAGGTTCATGGTTATGAAAGGTCTGAGAGTGAACGGCAACTGAAATCATCAGT
CCGGAGGGCACCCAGCTTTAGTGGTCCTTTGAATCTTCCAAATCGTGCTTCAGCAAACAGTC
TTTCAGCTCCTATCAAATCTTCTGGAGGATTTCGTGATTCTATAGATGACAAGTCGAAGGCT
AATGTGGTTCAAATCAAAGGAAGATTTTCAGTAACATCAGAAAACTTGGATCTTGCAAGGGC

FIGURE 3 (continued)

ATCCCCTTTGAGAAAATCTGCCAGTGTTGGGAATTGGATACTTGATTCTAAAATGCCAACGG
GCCAGGCCATCAAGGAGTCAAGTAGTCATCTCTCATTCATTATACCTCAGCTTCAAAATCTG
TTCCAGCAAAATTCAATGCAGCAGGATCTTATTATGAATCTAGTGAATACCTTACAACAAGC
TGCTGAAACAACAGATGGTTCTCAAAATGGAAAGTTGCCGCCTTTGCCTCGAGGATCTGACA
GCAATGGAACCGTTGTAGAACTTACAGCAGCTGAGCGAGAGAGGTTACTACTTACCAAGATA
ACCGAGCTTCGAGCTAGGATGAAAGAGTTGACGGAAGAACTTGAAGTAGAAAAATCAAAACA
GACCCAACTGCAGCAGAAATTGAAATCAGTCACCGGTCGCGAGCAATTGTAATCAGAGACCG
GGAACACTGACCTTACTACAGAGAAGCTTTTTAGGAGGAGAGAAAAGTATGTTTTGTACACT
AAGAAAACCAGAGAGCTCTCTGATCATGAAAGCAAAAAGGACAGGTTTGGTTCTGTTCTGTA
TAAGTGCAGAAGCAGAGTCACCATCGGCCATTTGTTTCTGACAGAAGAAGCCGGAAACAAAA
ACAGATAGAGAGAGATAAATAGAGAAGAAAGCTCTTTGGCCATGGAAAATTGTATTTGTTTA
TTTAATCTAAACACTACAAAACTTTACATTTTTTATTATTGTTAGCAACAAATATAGACTCT
TCCTTTTTTGTGTGGATTGTAAATGAAACATTATTTGATGTATTTGTTT

SEQ ID NO: 20, At4g10730 deduced protein sequence

MVSRFRLALEAVLGSRRRKKMASTSSGGGGGGDKKKKKGFSVNPKDYKLMEEVGYGASAVVH
RAIYLPTNEVVAIKSLDLDRCNSNLDDIRREAQTMTLIDHPNVIKSFCSFAVDHHLWVVMPF
MAQGSCLHLMKAAYPDGFEEAAICSMLKETLKALDYLHRQGHIHRDVKAGNILLDDTGEIKL
GDFGVSACLFDNGDRQRARNTFVGTPCWMAPEVLQPGSGYNSKADIWSFGITALELAHGHAP
FSKYPPMKVLLMTIQNAPPGLDYDRDKKFSKSFKELVALCLVKDQTKRPTAEKLLKHSFFKN
VKPPEICVKKLFVDLPPLWTRVKALQAKDAAQLALKGMASADQDAISQSEYQRGVSAWNFNI
EDLKEQASLLDDDDILTESREEEESFGEQLHNKARQVSGSQLLSENMNGKEKASDTEVVEPI
CEEKSTLNSTTSSVEQPASSSEQDVPQAKGKPVRLQTHSGPLSSGVVLINSDSEKVHGYERS
ESERQLKSSVRRAPSFSGPLNLPNRASANSLSAPIKSSGGFRDSIDDKSKANVVQIKGRFSV
TSENLDLARASPLRKSASVGNWILDSKMPTGQAIKESSSHLSFIIPQLQNLFQQNSMQQDLI
MNLVNTLQQAAETTDGSQNGKLPPLPRGSDSNGTVVELTAAERERLLLTKITELRARMKELT
EELEVEKSKQTQLQQKLKSVTGREQL

SEQ ID NO: 21, At4g24100 coding sequence

AAACTACTAGTCTCTATCTCTCTCAGCTCCAGATTTTGTTTCTTCTTCTTCTGTGTTAAATT
CATTTGATTTGTTGTATCTGAAGGCGAAATTACTGGTTTCTGATTTTTGGTGGTATTCAGGG
CGGTTTTAAAGCGACGGAAGAAGATGGTGGGAGGAGGAGGAGGTAGTAGTGGTCGTGGTGGT
GGTAGTGGTAGTGGTAGTAGTAAGCAGCAGAGAGGTTTCTCTATGAATCCTAAAGACTATAA
GCTAATGGAAGAAATAGGCCATGGAGCTAGCGCTGTTGTCTATCGAGCGATCTATCTCCCTA
CTAATGAAGTCGTCGCCATCAAGTGTTTGGATCTCGATCGCTGCAATAGCAATCTGGATGAT
ATTAGGAGGGAATCTCAGACTATGAGTTTGATAGACCATCCCAACGTTATAAAGTCGTTTTG
TTCATTCTCTGTCGACCATAGTCTTTGGGTTGTTATGCCATTCATGGCTCAAGGTTCGTGTT
TGCATCTTATGAAGACTGCGTATTCAGACGGATTTGAAGAGTCTGCTATATGTTGTGTATTA
AAAGAAACTCTTAAAGCTCTTGATTATCTTCATAGACAAGGCCATATCCATCGGGATGTTAA
GGCTGGAAACATACTTCTTGATGACAATGGTGAGATTAAGCTTGGCGATTTTGGTGTCTCTG
CTTGCTTGTTTGATAACGGTGATAGGCAACGTGCTAGAAACACATTTGTTGGTACTCCTTGC
TGGATGGCACCGGAAGTTTTGCAGCCGGGAAATGGATACAATTCCAAGGCTGATATCTGGTC
ATTTGGTATAACAGCACTTGAATTGGCCCATGGTCATGCACCTTTCTCAAAATATCCTCCCA

FIGURE 3 (continued)

```
TGAAGGTGCTCCTAATGACTATTCAAAACGCACCTCCTGGCCTTGATTATGACCGTGATAAG
AAATTTTCTAAGTCCTTTAAAGAAATGGTTGCAATGTGTTTGGTGAAAGATCAAACAAAAAG
GCCAACTGCTGAAAAACTGCTGAAGCACTCCTGTTTCAAACACACGAAGCCTCCAGAGCAAA
CTGTGAAAATTTTATTTTCCGATTTACCACCTCTTTGGACACGTGTAAAATCTCTTCAGGAT
AAGGATGCTCAACAGCTTGCATTAAAGAGAATGGCCACTGCTGACGAGGAAGCTATATCACA
GAGCGAATACCAAAGAGGAGTGAGCGCTTGGAACTTTGACGTCAGAGACTTGAAAACACAAG
CATCTTTGTTAATTGATGATGATGATCTAGAAGAGAGTAAGGAAGATGAAGAAATATTATGT
GCACAGTTTAATAAGGTGAATGACAGAGAGCAAGTATTTGATAGTCTGCAACTATATGAAAA
CATGAACGGAAAAGAAAAGGTTTCCAATACTGAGGTGGAAGAACCAACCTGCAAAGAGAAAT
TCACTTTCGTTACAACTACTTCTTCTTTAGAACGAATGTCACCAAATTCAGAGCATGACATT
CCCGAGGCCAAGGTTAAGCCATTAAGACGCCAAAGTCAGAGTGGACCACTTACAAGCAGGAC
TGTATTAAGCCACTCGGCTTCAGAGAAAAGTCATATCTTTGAAAGATCCGAGAGTGAACCGC
AGACGGCACCAACAGTCCGAAGAGCACCCAGCTTTAGTGGTCCTTTGAATCTTTCAACCCGT
GCTTCTTCAAACAGTTTGTCTGCTCCCATCAAATACTCAGGAGGATTCCGTGATTCTCTGGA
TGATAAGTCAAAGGCTAATCTGGTTCAGAAAGGACGATTTTCAGTAACATCAGGAAATGTAG
ATCTTGCGAAGGATGTTCCATTAAGTATAGTCCCTCGTCGATCTCCACAGGCGACCCCCCTG
AGAAAATCTGCAAGTGTGGGTAACTGGATACTTGAGCCCAAAATGCCAACAGCTCAGCCTCA
GACGATCAAGGAGCATAGTAGCCATCCTACGTCTTCCTCACCCATCATGCCTCAACTTCAAC
ATCTATTCCAGCAAAACTCAATACAACAGGATCTTATTATGAATTTACTAAATAGCTTACAA
CCCGTGGAGGCAACAGAAGGTTCTCAATCTGGGAAGTTACCACCTTTGCCTCGCTCAGACAG
TAATGGAAACGTTGAACCTGTGGCTTCAGAGAGGGAGAGGTTACTTCTTAGCAGTATCTCCG
ACCTCCGTGCTAGGCTGGACGACTTAACGGAGGAACTCGATATAGAGAAATCAAAATACAGC
CAACTGCAACAGAAATTGAAAGCATTCACGGGTCGCGAACACTAAGTGTAACCAGAGGGAAA
GCGACACTGGAAACACTGAACTGCACAGAACCTGTAGGAGAAAGAGTGAAGTCTCTTTTGGT
TATAACAGTAATAACCAGACAAGAGCTTAGAGACAGTGAGGCATAGAGCATATCAATTTCTT
TAGTTGGGTTCAGTGTAGGTTCCAGACGATGACAATGACGACTAAAACAAGATACGACCGAT
GTCTGCTTCTGATGTAAACTACTAGTTGAAGACAACAGAAACGAATACAGAAATAAAAGAAA
AGGAGAAGAAAGTTCCTTTGGGGGGTCTCAACCCCACATATATTTGCTTATATATTTATTAT
CACACGTTTTGATCATTTTTTGTTTTATTTTGTTTGGTGTATCATAATTTACTAGTGAGATA
AAGGAGAAAGCTCTTCTTTTGGGTTCTTTGTGTATTGTAATTTGTAAATGCAAATTGATTGA
TGTACTTTTGTGTTTTCATCACATTCTTAAACATTATCTTCTGGTTTTACCTTA
```

SEQ ID NO: 22, At4g24100 deduced protein sequence

MVGGGGGSSGRGGGSGSGSSKQQRGFSMNPKDYKLMEEIGHGASAVVYRAIYLPTNEVVAIK
CLDLDRCNSNLDDIRRESQTMSLIDHPNVIKSFCSFSVDHSLWVVMPFMAQGSCLHLMKTAY
SDGFEESAICCVLKETLKALDYLHRQGHIHRDVKAGNILLDDNGEIKLGDFGVSACLFDNGD
RQRARNTFVGTPCWMAPEVLQPGNGYNSKADIWSFGITALELAHGHAPFSKYPPMKVLLMTI
QNAPPGLDYDRDKKFSKSFKEMVAMCLVKDQTKRPTAEKLLKHSCFKHTKPPEQTVKILFSD
LPPLWTRVKSLQDKDAQQLALKRMATADEEAISQSEYQRGVSAWNFDVRDLKTQASLLIDDD
DLEESKEDEEILCAQFNKVNDREQVFDSLQLYENMNGKEKVSNTEVEEPTCKEKFTFVTTTS
SLERMSPNSEHDIPEAKVKPLRRQSQSGPLTSRTVLSHSASEKSHIFERSESEPQTAPTVRR
APSFSGPLNLSTRASSNSLSAPIKYSGGFRDSLDDKSKANLVQKGRFSVTSGNVDLAKDVPL
SIVPRRSPQATPLRKSASVGNWILEPKMPTAQPQTIKEHSSHPTSSSPIMPQLQHLFQQNSI
QQDLIMNLLNSLQPVEATEGSQSGKLPPLPRSDSNGNVEPVASERERLLLSSISDLRARLDD
LTEELDIEKSKYSQLQQKLKAFTGREH

FIGURE 3 (continued)

**SEQ ID NO: 23, *Oryza sativa* Ste20-like XM_469286 coding sequence**

ATGGCCAAGGCGTGGGAGAAGGTGGCGACGGCGGCGGGGTTGGGTGGGTCGGGGGAGAGGCG
CAAGTACCCGATCCGCGTGGAGGACTACGAGCTGTACGAGGAGATCGGGCAGGGGGTCAGCG
CCATCGTGTACCGATCGCTCTGCAAGCCCCTCGACGAGATCGTCGCCGTCAAGGTGCTCGAC
TTCGAGCGCACAAACAGTGACCTGTGGTTAGTTGTAATGCAAGTAGGTTATACTCGGATTGT
TGCGATTTACGTACCGCCGCTTGATCTGTCTAAAATGATAGTAACACGGATATGCTTGACGC
AGAACAACATCATGCGTGAAGCTCAGACGATGATTCTCATAGATCAGCCTAACGTCATGAAG
GCACATTGTTCATTTACAAATAACCACTCGTTGTGGGTGGTCATGCCATACATGGCTGGAGG
GTCTTGCCTTCACATAATGAAGTCAGTCTATCCAGATGGTTTTGAAGAAGCTGTCATTGCAA
CTGTACTTCGTGAAGTCCTGAAAGGTTTGGAGTACCTTCATCATCATGGGCATATACATCGT
GATGTGAAGGCAGGGAATATACTTGTTGATTCACGGGGTGTAGTCAAGCTTGGAGATTTTGG
GGTTTCTGCTTGCCTTTTTGATTCTGGTGACAGGCAACGGGCTAGGAATACTTTCGTGGGAA
CTCCTTGCTGGATGGCACCAGAGGTTATGGAGCAGCTACATGGATACGATTTCAAGGCAGAC
ATATGGTCCTTCGGAATTACTGCACTTGAACTTGCCCATGGTCATGCTCCTTTCTCGAAGTT
CCCTCCCATGAAGGTCTTACTTATGACACTTCAGAATGCCCCTCCGGGCCTTGACTATGAGA
GAGATAAGAAATTTTCAAGGCATTTCAAGCAAATGGTTGCTATGTGTCTGGTAAAAGACCCT
TCAAAAAGGCCTACAGCGAAAAAATTGCTGAAGCAACCCTTTTTCAAGCAAGCTCGCTCCAG
TGATTTCATTAGTCGAAAGCTTTTGGAGGGATTGCCTGGCCTTGGTGCCAGATATTTAGCTC
TGAAGGAAAAGGATGAAGTTTTACTTTCTCAAAAGAAAATGCCTGATGGACAGAAGGAAGAA
ATCTCACAGGATGAATACAAAAGAGGCATCAGTAGCTGGAACTTTGATATGGATGACCTGAA
GTCTCAAGCTTCACTTATTACAGAGTGTGATGACAGTATATCGTGCAAAGATTCAGATGCAT
CATGTTTCTATGACTTGGACACCATTTTACCAGAGCGAGCAACAGGACCTCATATGTCAAGA
GTTTTTTCAATTAAGTATGATACGGACACCGAAAATGATGTGATGAGCAATGATAAGTCAGC
AGTTTCATCTCCTGAGCACCCCATTTGTTTAGCAAGGAATACATCAATGCTCAGGACTACAA
ACGGGGTACATGCAAATGGCCAGGTCAGGAAACACAGCTCCACAGAAAGTAGTGAACTGGAC
TTGCAAGAGAAAGATTCAGATGCTATTCCAACCAGTTCATTCAGCTCATTTCATGAAAGGAA
GTTTTCTTTCAGTTCTTGCTCATCTGATGGATTTCTTTCATCCAAAGAGAGCTCGAAGCATC
AAATTAACATTCATAACCGTGACAAGTGCAACGGAGGACCCTTGCAAGTTGCAGATGAACCA
TCCCCTGAAGCTGTTCCAAAGGTGCCTAAATCATCAGCAGCAAATGTTGAGGACCACGACGA
TAGATCGAAACCTCCTCTTATACAGCAAAGAGGCCGTTTTAAAGTTACGCCTGGGCATGTTG
AGTTGGATAAGGATTTTCAATATCGTTCGATTCAAGAATTGATGCCATCTGTTGGGAGCAAT
ATACAGGCAATTTCGCACCTTCCTTCGTTAAGTATACCATCCTCAATTGAGGCTGCATCAAC
CATTATTGGTGGGTCCCTTTATATGCAGCTGTACAATGTTCTACAGACAAATATGCTTCAGA
GGGAGCAAATACTTCATGCGATGAAACAGTTAAGTGGTTGCGATATGGCAATGACGTCACCT
GCCTGCATTGCTCCTGCAAGTCGCGCATCATCTCCATCATCAGCATTATCAATTGACAGATC
ATTGTTGGAAGCGGCACACGAAAAGGAGAAGGAGCTGGTCAATGAGATCACTGAGCTGCAAT
GGCGGTTAGTGTGTTCGCAGGACGAGATACAGAGGCTCAAAGCAAAGGCAGCCCAGGTGACC
ATATCTGATCTTGTGGAGATGCTGTTAGATATGGAACAGCACGGGAAGGATTGA

FIGURE 3 (continued)

SEQ ID NO: 24, *Oryza sativa* Ste20-like XP_469286 deduced protein sequence

MAAAAGSVGGDDHHHHQQARYPLDAGSYRLLCKIGSGVSAVVYKAACVPLGSAVVAIKAIDL
ERSRANLDEVWREAKAMALLSHRNVLRAHCSFTVGSHLWVVMPFMAAGSLHSILSHGFPDGL
PEQCIAVVLRDTLRALCYLHEQGRIHRDIKAGNILVDSDGSVKLADFGVSASIYETAPSTSS
AFSGPINHAPPPSGAALSSSCFNDMAGTPYWMAPEVIHSHVGYGIKADIWSFGITALELAHG
RPPLSHLPPSKSMLMRITSRVRLEVDASSSSSEGSSSAARKKKKFSKAFKDMVSSCLCQEPA
KRPSAEKLLRHPFFKGCRSRDYDYLVRNVLDAVPTVEERCRDSTQLCGCARGARCVSPCRHA
SSGSNVVAAKNRRISGWNFNEESFELDPTDKPPEQQQQQPCFPFHHDNDDDMVEHEQEQRRR
QDGNDGSSDVAVPHLVTILGSLEMQRDMVMQVLEGDGGGGGETAGREEMLVGYVRELEKRVQ
ELSTEVEEEMARNAHLQELLHERACENHTDSSHTSGSR

SEQ ID NO: 25, *Oryza sativa* Ste20-like AK065283 coding sequence

GACCTTCTCTTCCTCCCTCGACACCTCTCCCCACGTTACGCTGCCTCCTCCTCCTCGCC
TCCCTCTCGTGGGCGTCGTCCCCCTCCGCCACCGCCGCCGCCCGCCGCAGCAGCCGCAGAAG
GGGACTCCACCTCCTCCCGGATCTGCTCGATCGCCCCCGATTCTGTAGCTTCTCCTCTGCTC
AGATCCGCCCCCTTGCTTTTCATCCAGCTCGTGGCACCCGAGATCCGCTGCCGCCGCCGCCG
TCTCTGCGGTCCTCCTCCCCCCTCGCCGGTGGGGAACCCCGCCGCCCCGAAGCGCGTTGCAG
CGTGTACTACTGCCGGACTGCCAAAGTACGCTTGCTGCTAGCCATTTCGGTAGCTTTTGTGG
TTTCTACTTAACTATCGTGTTTGGCAATACAACACCTTGGACCAAAGGATGCTTGAAAGATA
GACTGGATAATTAAGACTGGATGCCAAAGTACGCTTGCTGCTAGCCATTTCGGTAGCTTTTG
TGGTTTCTACTTAACTATCGTGTTTGGCAATACAACACCTTGGACCAAAGGATGCTTGAAAG
ATAGACTGGATAATTAAGAACTATATTGGACTGTACATTCGCCTATAGACTTAGTCATGCTG
CTGGTTGTTCTCTGTCGCTGCTACAAGGTGTTCGTGCTATTGCCTTCTGCTTCTGTGTGCTA
TGGTAATTGTAACTCTGTGGTTATTGCGCATGATGCTCTTTGAATTTGAGCCATGGAGCATG
CAAGGAGATTTCCAACAGATCCCAAAGAATATAAATTATGTGAGGAAGTTGGAGATGGTGTA
GTGCTACGGTGTACAAAGCTCTTTGTATCCCACTTAATATTGAAGTTGCCATTAAAGTTCTT
GACCTTGAGAAGTGCAGTAATGACCTGGATGGGATAAGACGAGAAGTACAAACCATGAGCTT
GATTGATCATCCAAATCTTCTTCGAGCATATTGCTCGTTTACAAATGGTCATCAGCTTTGGG
TTATTATGCCTTACATGGCCGCTGGATCTGCTCTGCACATTATGAAAACTTCTTTTCCAGAT
GGGTTTGAGGAGCCAGTCATTGCAACTCTTTTGCGGGAGGTTCTTAAAGCTCTTGTCTACCT
ACACTCCCAAGGGCATATTCACAGAGATGTAAAGGCTGGAAATATCCTAATAGATACAAATG
GAGCTGTCAAGCTAGGAGACTTTGGAGTGTCAGCCTGCATGTTTGATACTGGGAATAGGCAA
AGAGCACGAAACACTTTTGTAGGGACCCCTTGCTGGATGGCTCCAGAAGTTATGCAACAACT
GCATGGTTATGATTACAAAGCTGACATTTGGTCCTTTGGTATAACGGCATTGGAACTAGCAT
ATGGTCATGCTCCATTTTCAAAGTACCTCCAATGAAGGTATTGCTTATGACCTTGCAAAAT
GCACCACCAGGTCTAGACTATGAGAGGGACAAGCGATTTTCAAAGTCTTTCAAGGATTTGGT
TGCAACTTGCTTAGTCAAGGATCCACGCAAGCGTCCATCTTCAGAAAAGCTCTTGAAGCATT
CTTTTTTTAAGCATGCACGTACAGCTGAATTTCTTGCACGAAGTATTCTTGACGGCCTCCCC
CCGCTGGGTGAACGCTTTAGGACATTGAAGGGAAAAGAGGCTGACTTGCTTCTTAGTAATAA
GCTTGGTTCAGAGAGCAAGGAGCAACTATCACAGAAAGAGTACATACGAGGAATCAGTGGTT
GGAACTTCAATCTGGAGGACTTGAAAAATGCAGCCGCCCTTATAGACAATACAAACGGAACG

FIGURE 3 (continued)

```
TGCCATTTAGATGGTGTTAACAGCAAATTCAAGGATGGTTTACAAGAAGCTAATGAACCAGA
AAATATTTACCAGGGACGGGCTAACCTTGTTGCTTCTGCAAGGCCTGAGGATGAGATACAAG
AGGTCGAAGATCTGGATGGTGCTCTCGCCTCTTCTTTCCCCAGCCGCCCCCTTGAGGCACTA
AAATCTTGCTTTGATGTTTGTGGGGATGATGATCCCCCTACTGCTACTGATTTGAGGGAGCA
ACCAAATATGGAATCTACATCACCTATGCAGCAGTTCCAACAAATTGAGAATCATAAAAGTG
CCAACTGTAATGGTGAAAGTTTGGAAAGAAGTGCCTCTGTACCATCAAATTTGGTCAATAGT
GGGTCCCACAAGTTCTTAAGTGGTTCCCTGATACCTGAACATGTTCTTTCTCCTTACAGGAA
TGTTGGCAATGACCCAGCAAGGAATGAGTGTCATCAGAAAAATACATGCAACAGGAACCGCA
GTGGGCCTTTATTCCGCCAAATGAAAGATCCACGCGCACATCTGCCTGTTGAACCTGAGGAG
CAATCCGAAGGAAAAGTTATCCAGCGAAGGGGCGTTTTCAGGTTACATCAGATAGTATTGC
TCAAAAGGTAGCTTCATCCGCAAGCAGCAGTAGGTGCTCAAATTTACCAATCGGAGTAACAC
GATCAACTGTCCATCCATCGACAATTCTTCCAACACTACAATTCATGATACAGCAAAATACT
ATGCAAAAGGAAGTGATAAGTAGACTGATTTCTTCAATTGAGGAAATATCTGATGCTGCTGA
TGCAAGTACAACTGGTTCATCTCAGCCATCTGGAGTGCATTTCAGAGAGAAGGAACTGCAGT
CGTACATCGCCAACTTGCAGCAAAGTGTCACCGAACTTGCTGAGGAAGTTCAGAGATTAAAG
CTCAAAAACACTCAGCTCGAGGAGCAGATCAATGCATTGCCCAAAAAAGATGAAAGGTTACG
AAGAGAGGATACCCGACAACAATGATATGCACAATGCACTTGTAACCCCCGCTGTAAAATCA
GTTCCCCAATTTTGAATTTGGTTAGCAAAATTATTTGTATTTTGTTCGAAGTCAGGCCTGGT
GTATCTTTGTAATTTGTAATTATTTTAGCAAGGTGAAATTATAGTTATTTTCATTTGTACAG
GATATTTCAATCTATACCAAAGTTAAAAGCTTGGTACTAGAAAATACCAAATCATCTTTCCT
```

**SEQ ID NO: 26, *Oryza sativa* Ste20-like deduced protein sequence (BAD37346)**

```
MEHARRFPTDPKEYKLCEEVGDGVSATVYKALCIPLNIEVAIKVLDLEKCSNDLDGIRREVQ
TMSLIDHPNLLRAYCSFTNGHQLWVIMPYMAAGSALHIMKTSFPDGFEEPVIATLLREVLKA
LVYLHSQGHIHRDVKAGNILIDTNGAVKLGDFGVSACMFDTGNRQRARNTFVGTPCWMAPEV
MQQLHGYDYKADIWSFGITALELAHGHAPFSKYPPMKVLLMTLQNAPPGLDYERDKRFSKSF
KDLVATCLVKDPRKRPSSEKLLKHSFFKHARTAEFLARSILDGLPPLGERFRTLKGKEADLL
LSNKLGSESKEQLSQKEYIRGISGWNFNLEDLKNAAALIDNTNGTCHLDGVNSKFKDGLQEA
NEPENIYQGRANLVASARPEDEIQEVEDLDGALASSFPSRPLEALKSCFDVCGDDDPPTATD
LREQPNMESTSPMQQFQQIENHKSANCNGESLERSASVPSNLVNSGSHKFLSGSLIPEHVLS
PYRNVGNDPARNECHQKNTCNRNRSGPLFRQMKDPRAHLPVEPEEQSEGKVIQRRGRFQVTS
DSIAQKVASSASSSRCSNLPIGVTRSTVHPSTILPTLQFMIQQNTMQKEVISRLISSIEEIS
DAADASTTGSSQPSGVHFREKELQSYIANLQQSVTELAEEVQRLKLKNTQLEEQINALPKKD
ERLRREDTRQQ
```

FIGURE 3 (continued)

**SEQ ID NO: 27, *Oryza sativa* Ste20-like XM_468215 coding sequence**

ATGGCCAAGGCGTGGGAGAAGGTGGCGACGGCGGCGGGGTTGGGTGGGTCGGGGGAGAGGCG
CAAGTACCCGATCCGCGTGGAGGACTACGAGCTGTACGAGGAGATCGGGCAGGGGGTCAGCG
CCATCGTGTACCGATCGCTCTGCAAGCCCCTCGACGAGATCGTCGCCGTCAAGGTGCTCGAC
TTCGAGCGCACAAACAGTGACCTGTGGTTAGTTGTAATGCAAGTAGGTTATACTCGGATTGT
TGCGATTTACGTACCGCCGCTTGATCTGTCTAAAATGATAGTAACACGGATATGCTTGACGC
AGAACAACATCATGCGTGAAGCTCAGACGATGATTCTCATAGATCAGCCTAACGTCATGAAG
GCACATTGTTCATTTACAAATAACCACTCGTTGTGGGTGGTCATGCCATACATGGCTGGAGG
GTCTTGCCTTCACATAATGAAGTCAGTCTATCCAGATGGTTTTGAAGAAGCTGTCATTGCAA
CTGTACTTCGTGAAGTCCTGAAAGGTTTGGAGTACCTTCATCATCATGGGCATATACATCGT
GATGTGAAGGCAGGGAATATACTTGTTGATTCACGGGGTGTAGTCAAGCTTGGAGATTTTGG
GGTTTCTGCTTGCCTTTTTGATTCTGGTGACAGGCAACGGGCTAGGAATACTTTCGTGGGAA
CTCCTTGCTGGATGGCACCAGAGGTTATGGAGCAGCTACATGGATACGATTTCAAGGCAGAC
ATATGGTCCTTCGGAATTACTGCACTTGAACTTGCCCATGGTCATGCTCCTTTCTCGAAGTT
CCCTCCCATGAAGGTCTTACTTATGACACTTCAGAATGCCCCTCCGGGCCTTGACTATGAGA
GAGATAAGAAATTTTCAAGGCATTTCAAGCAAATGGTTGCTATGTGTCTGGTAAAAGACCCT
TCAAAAAGGCCTACAGCGAAAAAATTGCTGAAGCAACCCTTTTTCAAGCAAGCTCGCTCCAG
TGATTTCATTAGTCGAAAGCTTTTGGAGGGATTGCCTGGCCTTGGTGCCAGATATTTAGCTC
TGAAGGAAAAGGATGAAGTTTTACTTTCTCAAAAGAAAATGCCTGATGGACAGAAGGAAGAA
ATCTCACAGGATGAATACAAAAGAGGCATCAGTAGCTGGAACTTTGATATGGATGACCTGAA
GTCTCAAGCTTCACTTATTACAGAGTGTGATGACAGTATATCGTGCAAAGATTCAGATGCAT
CATGTTTCTATGACTTGGACACCATTTTACCAGAGCGAGCAACAGGACCTCATATGTCAAGA
GTTTTTTCAATTAAGTATGATACGGACACCGAAAATGATGTGATGAGCAATGATAAGTCAGC
AGTTTCATCTCCTGAGCACCCCATTTGTTTAGCAAGGAATACATCAATGCTCAGGACTACAA
ACGGGGTACATGCAAATGGCCAGGTCAGGAAACACAGCTCCACAGAAAGTAGTGAACTGGAC
TTGCAAGAGAAAGATTCAGATGCTATTCCAACCAGTTCATTCAGCTCATTTCATGAAAGGAA
GTTTTCTTTCAGTTCTTGCTCATCTGATGGATTTCTTTCATCCAAAGAGAGCTCGAAGCATC
AAATTAACATTCATAACCGTGACAAGTGCAACGGAGGACCCTTGCAAGTTGCAGATGAACCA
TCCCCTGAAGCTGTTCCAAAGGTGCCTAAATCATCAGCAGCAAATGTTGAGGACCACGACGA
TAGATCGAAACCTCCTCTTATACAGCAAAGAGGCCGTTTTAAAGTTACGCCTGGGCATGTTG
AGTTGGATAAGGATTTTCAATATCGTTCGATTCAAGAATTGATGCCATCTGTTGGGAGCAAT
ATACAGGCAATTTCGCACCTTCCTTCGTTAAGTATACCATCCTCAATTGAGGCTGCATCAAC
CATTATTGGTGGGTCCCTTTATATGCAGCTGTACAATGTTCTACAGACAAATATGCTTCAGA
GGGAGCAAATACTTCATGCGATGAAACAGTTAAGTGGTTGCGATATGGCAATGACGTCACCT
GCCTGCATTGCTCCTGCAAGTCGCGCATCATCTCCATCATCAGCATTATCAATTGACAGATC
ATTGTTGGAAGCGGCACACGAAAGGAGAAGGAGCTGGTCAATGAGATCACTGAGCTGCAAT
GGCGGTTAGTGTGTTCGCAGGACGAGATACAGAGGCTCAAAGCAAAGGCAGCCCAGGTGACC
ATATCTGATCTTGTGGAGATGCTGTTAGATATGGAACAGCACGGGAAGGATTGA

FIGURE 3 (continued)

**SEQ ID NO: 28, *Oryza sativa* Ste20-like XP_468215 deduced protein sequence**

MAKAWEKVATAAGLGGSGERRKYPIRVEDYELYEEIGQGVSAIVYRSLCKPLDEIVAVKVLD
FERTNSDLWLVVMQVGYTRIVAIYVPPLDLSKMIVTRICLTQNNIMREAQTMILIDQPNVMK
AHCSFTNNHSLWVVMPYMAGGSCLHIMKSVYPDGFEEAVIATVLREVLKGLEYLHHHGHIHR
DVKAGNILVDSRGVVKLGDFGVSACLFDSGDRQRARNTFVGTPCWMAPEVMEQLHGYDFKAD
IWSFGITALELAHGHAPFSKFPPMKVLLMTLQNAPPGLDYERDKKFSRHFKQMVAMCLVKDP
SKRPTAKKLLKQPFFKQARSSDFISRKLLEGLPGLGARYLALKEKDEVLLSQKKMPDGQKEE
ISQDEYKRGISSWNFDMDDLKSQASLITECDDSISCKDSDASCFYDLDTILPERATGPHMSR
VFSIKYDTDTENDVMSNDKSAVSSPEHPICLARNTSMLRTTNGVHANGQVRKHSSTESSELD
LQEKDSDAIPTSSFSSFHERKFSFSSCSSDGFLSSKESSKHQINIHNRDKCNGGPLQVADEP
SPEAVPKVPKSSAANVEDHDDRSKPPLIQQRGRFKVTPGHVELDKDFQYRSIQELMPSVGSN
IQAISHLPSLSIPSSIEAASTIIGGSLYMQLYNVLQTNMLQREQILHAMKQLSGCDMAMTSP
ACIAPASRASSPSSALSIDRSLLEAAHEKEKELVNEITELQWRLVCSQDEIQRLKAKAAQVT
ISDLVEMLLDMEQHGKD

**SEQ ID NO: 29, *Oryza sativa* Ste20-like AC092696 coding sequence**

ATGGGGAGGAACGGGAGCGTCAAGCGTACGTCGTCGTCGGGGGCGGCGGCGGCGTTCACGGC
GAATCCCCGCGACTACCAGCTCATGGAGGAGGTCGGGTACGGGGCGCACGCCGTCGTGTACC
GCGCGCTGTTCGTCCCCAGGAACGACGTCGTGGCTGTCAAGTGCCTGGATCTCGATCAGCTC
AACAACAACATCGATGAAATCCAACGGGAGGCTCAAATCATGAGCTTGATAGAGCATCCTAA
TGTCATCAGGGCTTACTGCTCATTTGTTGTTGAGCACAGCCTTTGGGTAGTAATGCCATTTA
TGACTGAGGGTTCATGTCTGCACCTAATGAAGATTGCATATCCTGATGGTTTCGAGGAACCT
GTTATTGGCTCTATTCTAAAGGAAACACTTAAGGCTTTGGAGTACCTTCACAGGCAAGGACA
AATCCATCGTGATGTCAAGGCCGGCAATATCCTTGTTGATAATGCTGGTATAGTGAAGCTTG
GGGACTTCGGCGTGTCTGCTTGTATGTTTGATAGAGGTGATCGACAAAGATCTAGGAACACA
TTTGTGGGAACACCGTGTTGGATGGCTCCAGAAGTGCTCCAGCCAGGCACTGGATATAACTT
CAAAGCTGACATATGGTCATTTGGAATCACTGCACTTGAACTTGCCCATGGCCATGCACCGT
TTTCAAAGTATCCCCCTATGAAGGTTCTTCTCATGACCCTCCAGAATGCTCCACCTGGTCTC
GACTATGATCGAGACCGAAGATTCTCAAAGTCATTTAAGGAGATGGTTGCAATGTGCTTGGT
AAAAGATCAAACAAAGAGACCAACAGCTGAGAAGTTGCTAAAGCATTCATTTTTCAAAAATG
CAAAACCTCCAGAATTGACAATGAAGGGTATCTTAACTGATTTACCTCCTCTATGGGACCGT
GTAAAGGCTCTCCAGCTTAAAGATGCAGCACAGTTGGCCTTGAAGAAAATGCCTTCTTCTGA
GCAGGAGGCACTCTCCATGAGTGAATACCAACGAGGTGTTAGTGCATGGAACTTCGATGTTG
AAGATCTCAAGGCCCAAGCATCACTAATTCGTGATGATGAACCCCCTGAAATAAAAGAAGAC
GATGATACTGCAAGAACCATTGAAGTTGAAAAGGATTCATTTTCTAGGAATCATTTGGGGAA
GTCGTCGAGTACAATTGAAAATTTCTTCAGTGGACGGACCTCTACCACTGCAGCAAATTCGG
ATGGAAAAGGCGATTTTTCATTTGAAGCTTTTGATTTTGGTGAAAACAACGTTGATACTAAA
ATTATGCCCAATGGGTATGAAAACGCTAGATCAGAGAATAGCTCATCACCCTCTACATCAAA
GCAAGATCCAGAGTCAAAATATTGGAGAAGTACTTCTGGACAGAAACAACAAACTTCTGGCA
CTCCAGCTGTCCATTCTGGTGGGGTTAATAGCTCAACAACTGAAAAGGGCCATGGTGTTGAA
AGGGATGCAACTGTTCAATTGGCATCTGATAAACTTAGGACTGAAACGAGAAGAGCAACAAA
TCTTAGTGGTCCATTGTCACTGCCAACTCGTGCTTCTGCAAACAGTCTGTCAGCTCCTATTC
GATCTTCAGGA

FIGURE 3 (continued)

**SEQ ID NO: 30, *Oryza sativa* Ste20-like AAL54869 deduced protein sequence**
MGRNGSVKRTSSSGAAAAFTANPRDYQLMEEVGYGAHAVVYRALFVPRNDVVAVKCLDLDQL
NNNIDEIQREAQIMSLIEHPNVIRAYCSFVVEHSLWVVMPFMTEGSCLHLMKIAYPDGFEEP
VIGSILKETLKALEYLHRQGQIHRDVKAGNILVDNAGIVKLGDFGVSACMFDRGDRQRSRNT
FVGTPCWMAPEVLQPGTGYNFKADIWSFGITALELAHGHAPFSKYPPMKVLLMTLQNAPPGL
DYDRDRRFSKSFKEMVAMCLVKDQTKRPTAEKLLKHSFFKNAKPPELTMKGILTDLPPLWDR
VKALQLKDAAQLALKKMPSSEQEALSMSEYQRGVSAWNFDVEDLKAQASLIRDDEPPEIKED
DDTARTIEVEKDSFSRNHLGKSSSTIENFFSGRTSTTAANSDGKGDFSFEAFDFGENNVDTK
IMPNGYENARSENSSSPSTSKQDPESKYWRSTSGQKQQTSGTPAVHSGGVNSSTTEKGHGVE
RDATVQLASDKLRTETRRATNLSGPLSLPTRASANSLSAPIRSSG

**SEQ ID NO: 31, *Oryza sativa* Ste20-like NM_187542 coding sequence**
ATGGTGAGGAGCGGGAGTGTGCGGCGGACGGCCGCGTCGTCGTCGCCCGCCGCGGCGGCGGT
GCCGACGGCCTTCACCGCCTCGCCCGGCGACTACCGCCTTCTGGAGGAGGTCGGCTACGGCG
CGAACGCCGTCGTGTACCGGGCGGTGTTCCTGCCATCCAACCGGACCGTCGCCGTCAAGTGC
CTGGATCTCGATCGTGTCAACAGTAACCTCGATGATATAAGAAAGAGGCACAAACGATGAG
CTTGATAGATCACCCTAATGTCATCAGGGCTTACTGCTCATTTGTTGTGGATCATAACCTCT
GGGTGATAATGCCATTCATGTCAGAGGGTTCATGTTTACACCTGATGAAGGTTGCATATCCT
GATGGTTTTGAGGAGCCTGTTATCGCCTCTATCCTAAAGGAAACACTTAAGGCTCTAGAGTA
CCTCCATCGGCAAGGACATATCCATAGGGATGTCAAGCGTAATATTATACAGGCGGGTAATA
TCCTTATGGACAGTCCTGGTATAGTGAAACTTGGGGACTTTGGTGTCTCTGCTTGTATGTTT
GATAGAGGTGATAGACAAAGATCCAGGAATACATTCGTGGGAACACCATGCTGGATGGCTCC
AGAAGTTCTCCAGCCTGGAGCAGGATATAATTTCAAGAAATATGTTTCAAACCATTTGTTTA
CCAACTTAATTTGGTTATTTAAAATTTCCTTAAGGGGTAAGAACTCTAACTACCATAAAAAT
ACTGGGAATAAGGTTCTTCTCATGACCCTTCAAAATGCACCACCAGGCCTTGACTATGACCG
TGATAAAAGATTCTCAAAGTCTTTCAAGGAAATGGTTGCAATGTGCCTGGTCAAAGATCAAA
CAAAGAGGCCAACGGCTGAAAAGTTACTAAAGCACTCATTTTTCAAGAACGCAAAACCTCCA
GAGCTGACTGTTAAGAGTATTTTAACTGATTTGCCCCCTCTGTGGGATCGTGTAAAAGCGCT
CCAGCTAAAAGATGCAGCACAATTAGCTTTGAAGAAAATGCCTTCTTCTGAACAGGAGGCAC
TTTCTATGATTCATGATGATGATCCACCTGAAATAAAGGAAGATGTTGACAATGATAGAATA
AATGAAGCTGATAAGGAGCCGTTTTCTGGCAATCATTTTGGACAACCAAAAATTTTGAGTGG
AAAGCACTTCAGGTTGAATCATGAACAAACTTGTGTCACTGCAGTAAGTCCAGGGGGGAATA
TGCATGAGACAAGCAGAGGATTGGTTTCTGAACCTGGTGATGCTGATAGTGAAAGGAAAGTT
GATGGATATAGAAAACAAGGGGAAGCGGCAGTTAAGTTGGCATCTGATAAACAAAAGAGTTG
TACAAAAAGAACCACAAATCTCAGTGGTCCTCTTGCACTCCCTACTCGTGCTTCTGCAAATA
GTCTGTCTGCTCCTATTCGGTCTTCTGGAGGCTATGTGGGCTCCTTGGGAGATAAGTCTAAG
CGTAGTGTGGTGGAGATAAAAGGACGTTTTTCAGTGACATCTGAGAATGTGGATCTTGCAAA
GGTTCAGGAAGTTCCAACAAGCGGCATTTCACGCAAATTACAGGAGGGATCTTCACTGAGAA
AATCAGCCAGCGTTGGTCATTGGCCGGTGGATGCTAAGCCAATGGATCTCATCACAAACCTC
CTAAGTAGCTTGCAACAGAATGAGAAAGCTGACGCAACACAGTATAGACTTGGTAATATGGA
TGGTGATACAGAGGTTGAAACGTCTATTTCCGAGGGAGAACGGTCATTACTTGTCAAAATAT
TTGAATTGCAATCTAGAATGATTTCATTAACCGATGAACTGATCACAACAAAACTGCAACAT
GTCCAGCTACAAGAAGAGCTAAAAATACTGTACTGTCACGAAGAAATAATCGACACTAGGGA
GGTGGACAATGCTTGA

FIGURE 3 (continued)

SEQ ID NO: 32, *Oryza sativa* Ste20-like NP_912431 deduced protein sequence

MVRSGSVRRTAASSSPAAAAVPTAFTASPGDYRLLEEVGYGANAVVYRAVFLPSNRTVAVKC
LDLDRVNSNLDDIRKEAQTMSLIDHPNVIRAYCSFVVDHNLWVIMPFMSEGSCLHLMKVAYP
DGFEEPVIASILKETLKALEYLHRQGHIHRDVKRNIIQAGNILMDSPGIVKLGDFGVSACMF
DRGDRQRSRNTFVGTPCWMAPEVLQPGAGYNFKKYVSNHLFTNLIWLFKISLRGKNSNYHKN
TGNKVLLMTLQNAPPGLDYDRDKRFSKSFKEMVAMCLVKDQTKRPTAEKLLKHSFFKNAKPP
ELTVKSILTDLPPLWDRVKALQLKDAAQLALKKMPSSEQEALSMIHDDDPPEIKEDVDNDRI
NEADKEPFSGNHFGQPKILSGKHFRLNHEQTCVTAVSPGGNMHETSRGLVSEPGDADSERKV
DGYRKQGEAAVKLASDKQKSCTKRTTNLSGPLALPTRASANSLSAPIRSSGGYVGSLGDKSK
RSVVEIKGRFSVTSENVDLAKVQEVPTSGISRKLQEGSSLRKSASVGHWPVDAKPMDLITNL
LSSLQQNEKADATQYRLGNMDGDTEVETSISEGERSLLVKIFELQSRMISLTDELITTKLQH
VQLQEELKILYCHEEIIDTREVDNA

SEQ ID NO: 33, *Medicago sativa* Ste20-like coding sequence

ATGGCTACCAACATAGCAGAAAGAGTGCAATATCCATTAGACTCTTCCTCCTATAAAATC
GTCGACGAGATTGGCGCCGGTAACAGCGCCGTCGTCTACAAAGCAATCTGCATCCCTATA
AACTCCACACCAGTAGCTATCAAATCCATAGACTTGGATCGTTCGCGCCCCGACCTTGAC
GATGTTAGACGTGAAGCAAAGACATTATCACTTCTTTCCCACCCCAACATCCTCAAAGCT
CACTGTTCTTTCACCGTTGACAACCGTCTTTGGGTGGTTATGCCATTCATGGCTGGAGGT
TCATTACAATCCATTATCTCTCACTCTTTCCAAAACGGCTTAACAGAACAATCCATAGCT
GTTATTCTCAAAGACACTCTCAATGCTCTTTCTTACCTTCATGGACAAGGACATCTTCAT
AGAGATATCAAATCTGGTAACATCCTTGTTGACTCAAATGGATTAGTGAAACTTGCAGAT
TTTGGTGTTTCTGCTTCCATTTATGAATCAAACAACTCTGTAGGAGCATGTTCTTCTTAT
TCATCTTCGTCTTCGAATTCTTCTTCTTCTCATATATTTACTGATTTGCTGGAACACCT
TATTGGATGGCTCCTGAGGTTATTCACTCTCATAATGGTTACAGTTTCAAAGCTGATATC
TGGTCTTTTGGGATAACAGCTTTGGAGTTAGCACATGGAAGACCACCACTTTCTCATCTT
CCTCCTTCTAAGTCATTGATGCTAAACATTACAAAGAGGTTTAAGTTTTCTGATTTTGAT
AAACATAGTTACAAGGGTCATGGTGGTAGTAACAAATTCTCTAAGGCTTTTAAGGATATG
GTTGCTTTATGTTTGAATCAAGATCCTACAAAAAGACCCTCTGCTGAGAAGTTACTTAAG
CATTCATTCTTTAAAAACTGCAAGGGATCAGATGTTTTGGTGAAGAATGTGTTGAATGGA
TTGCCTAGTGTTGAGAAAAGGTATAAAGAGATCAAAGCTATAATGGATCCAGATTCAAAG
TGCAAGGATGATGGAGACGACGATGATGACGAGTCAGTGAAAAATGTGAAACAGAGAAGA
ATCAGTGGCTGGAATTTCAATGAAGATGGATTGGAACTTGTGCCTGTATTCCCAAAGGAT
CAAAGCAAAGATGATGAAGTTGTGAAACAAGTTCGGTTCGAAGAAGAAAAAGTGATCCAA
GAGGATGCTGTTGTTACAGCATCAGGAACTGTGATGGAGCCAAAGACCAATACTTCTGAT
GTGGTTGATCATGAAAATGTCGGTGGTGTTGTTAAGAACCGTGAAGCTACGTTGGCAACG
TTGAATGTGTTGAAAGAGAGCTTGGAACAAGAGTTGGGACAAGTTAAGTTTCTAATGAAT
CTAATTGGTGGAGAGGAGATTCATGTGGCTGAAAGTGATGAGAAATGGTGCAAGAGATC
TCTAAGTTGAGGACAGAATTGGAAAATGAGAAGAAGAAGAACTTGCAGCTGGAGATGCAG
CTGGAGAATATCAAGCTTCACCTAATTTCCTCTGCTGCTAATAGTCCTACTAGT

FIGURE 3 (continued)

SEQ ID NO: 34, *Medicago sativa* Ste20-like deduced protein sequence

MATNIAERVQYPLDSSSYKIVDEIGAGNSAVVYKAICIPINSTPVAIKSIDLDRSRPDLDDV
RREAKTLSLLSHPNILKAHCSFTVDNRLWVVMPFMAGGSLQSIISHSFQNGLTEQSIAVILK
DTLNALSYLHGQGHLHRDIKSGNILVDSNGLVKLADFGVSASIYESNNSVGACSSYSSSSSN
SSSSHIFTDFAGTPYWMAPEVIHSHNGYSFKADIWSFGITALELAHGRPPLSHLPPSKSLML
NITKRFKFSDFDKHSYKGHGGSNKFSKAFKDMVALCLNQDPTKRPSAEKLLKHSFFKNCKGS
DVLVKNVLNGLPSVEKRYKEIKAIMDPDSKCKDDGDDDDDESVKNVKQRRISGWNFNEDGLE
LVPVFPKDQSKDDEVVKQVRFEEEKVIQEDAVVTASGTVMEPKTNTSDVVDHENVGGVVKNR
EATLATLNVLKESLEQELGQVKFLMNLIGGEEIHVAESDEKMVQEISKLRTELENEKKKNLQ
LEMQLENIKLHLISSAANSPTS

FIGURE 3 (continued)

SEQUENCE LISTING

<160> NUMBER OF SEQ ID NOS: 34

<210> SEQ ID NO 1
<211> LENGTH: 1554
<212> TYPE: DNA
<213> ORGANISM: Arabidopsis thaliana

<400> SEQUENCE: 1

```
cataacaatt caataagcaa gagtgtactc atcttctttc tatttatggc tcggaacaag      60
ctcgagttcc ctcttgatgc tgaagcctac gagatcatct gcaagatagg cgttggtgtt     120
agtgcttcgg tctacaaggc catatgcatt ccgatgaact caatggtagt tgctatcaaa     180
gccatcgatc ttgatcagtc gcgggctgac tttgacagtc ttcgccgtga aaccaagacg     240
atgtctctgc tttctcatcc gaatattctc aatgcttatt gttcattcac cgttgatcga     300
tgtctctggg tggttatgcc attcatgtct tgtggctctc ttcattcgat cgtctcttcg     360
tcttttccaa gtgggttacc agaaaactgc atttccgtct tcctcaagga aactctgaat     420
gcaatctcgt atcttcacga tcagggtcat ttgcaccgtg acatcaaggc aggtaacatt     480
ctggtagatt ctgatggatc cgtgaagctc gctgatttcg gagtatctgc atccatctat     540
gaacccgtga catcttcctc tggaacaaca tcttcttctt taaggttaac tgatatagcg     600
ggaacaccgt attggatggc tccggaagtg gttcattccc acacagggta tggtttcaaa     660
gcagacattt ggtctttcgg gataacagcg ttggagttag cacatggaag acctccgtta     720
tctcacttac cgccgttgaa gagtctgctc atgaagatca ccaaaaggtt tcattttttct    780
gattacgaga tcaatacgag cggaagcagc aaaaagggta acaagaagtt ctcaaaagct     840
tttagagaaa tggttggttt gtgtctagag caagatccta ctaaaagacc atcggcagag     900
aagttgttga agcatccttt tttcaagaac tgtaaaggac tcgactttgt ggtcaagaac     960
gtgttgcata gcttgtcaaa cgcagagcag atgtttatgg agagtcagat tttgatcaag    1020
agtgttggag atgatgatga agaagaagaa gaagaagacg aagagatagt gaagaataga    1080
agaatcagtg ggtggaattt ccgtgaagac gatctccaac ttagtccagt gttcccagct    1140
actgaatcag actcttctga gtccagtcca cgtgaagaag atcaatcaaa agacaaaaag    1200
gaagacgata acgtcacaat aacggggtat gaactcggtt taggtttgtc gaacgaggaa    1260
gctaagaacc aagaaggtga ggttgttggg tttgataaag atttggtgtt agagaaactg    1320
aaagtgttga agaaaagttt agagcatcaa agagcaagag tgtcgattat aatcgaagca    1380
ttgagtgggg acaaggaaga gaagagcaga gaagaagagc ttctagagat ggtggagaag    1440
ttaaagattg aattggaaac tgagaagcta aagaccttgc gtgctgataa agatagtgtt    1500
ttgggttaac tattctaaac ttgttaatat ttttttttcta tatgctaaaa ttat           1554
```

<210> SEQ ID NO 2
<211> LENGTH: 487
<212> TYPE: PRT
<213> ORGANISM: Arabidopsis thaliana

<400> SEQUENCE: 2

```
Met Ala Arg Asn Lys Leu Glu Phe Pro Leu Asp Ala Glu Ala Tyr Glu
1               5                   10                  15

Ile Ile Cys Lys Ile Gly Val Gly Val Ser Ala Ser Val Tyr Lys Ala
                20                  25                  30

Ile Cys Ile Pro Met Asn Ser Met Val Val Ala Ile Lys Ala Ile Asp
            35                  40                  45
```

```
Leu Asp Gln Ser Arg Ala Asp Phe Asp Ser Leu Arg Arg Glu Thr Lys
    50                  55                  60

Thr Met Ser Leu Leu Ser His Pro Asn Ile Leu Asn Ala Tyr Cys Ser
65              70                  75                  80

Phe Thr Val Asp Arg Cys Leu Trp Val Val Met Pro Phe Met Ser Cys
            85                  90                  95

Gly Ser Leu His Ser Ile Val Ser Ser Ser Phe Pro Ser Gly Leu Pro
            100                 105                 110

Glu Asn Cys Ile Ser Val Phe Leu Lys Glu Thr Leu Asn Ala Ile Ser
            115                 120                 125

Tyr Leu His Asp Gln Gly His Leu His Arg Asp Ile Lys Ala Gly Asn
    130                 135                 140

Ile Leu Val Asp Ser Asp Gly Ser Val Lys Leu Ala Asp Phe Gly Val
145                 150                 155                 160

Ser Ala Ser Ile Tyr Glu Pro Val Thr Ser Ser Gly Thr Thr Ser
                165                 170                 175

Ser Ser Leu Arg Leu Thr Asp Ile Ala Gly Thr Pro Tyr Trp Met Ala
            180                 185                 190

Pro Glu Val Val His Ser His Thr Gly Tyr Gly Phe Lys Ala Asp Ile
            195                 200                 205

Trp Ser Phe Gly Ile Thr Ala Leu Glu Leu Ala His Gly Arg Pro Pro
    210                 215                 220

Leu Ser His Leu Pro Pro Leu Lys Ser Leu Leu Met Lys Ile Thr Lys
225                 230                 235                 240

Arg Phe His Phe Ser Asp Tyr Glu Ile Asn Thr Ser Gly Ser Ser Lys
            245                 250                 255

Lys Gly Asn Lys Lys Phe Ser Lys Ala Phe Arg Glu Met Val Gly Leu
            260                 265                 270

Cys Leu Glu Gln Asp Pro Thr Lys Arg Pro Ser Ala Glu Lys Leu Leu
            275                 280                 285

Lys His Pro Phe Phe Lys Asn Cys Lys Gly Leu Asp Phe Val Val Lys
            290                 295                 300

Asn Val Leu His Ser Leu Ser Asn Ala Glu Gln Met Phe Met Glu Ser
305                 310                 315                 320

Gln Ile Leu Ile Lys Ser Val Gly Asp Asp Glu Glu Glu Glu Glu Glu
            325                 330                 335

Glu Asp Glu Glu Ile Val Lys Asn Arg Arg Ile Ser Gly Trp Asn Phe
            340                 345                 350

Arg Glu Asp Asp Leu Gln Leu Ser Pro Val Phe Pro Ala Thr Glu Ser
            355                 360                 365

Asp Ser Ser Glu Ser Ser Pro Arg Glu Glu Asp Gln Ser Lys Asp Lys
            370                 375                 380

Lys Glu Asp Asp Asn Val Thr Ile Thr Gly Tyr Glu Leu Gly Leu Gly
385                 390                 395                 400

Leu Ser Asn Glu Glu Ala Lys Asn Gln Glu Gly Glu Val Val Gly Phe
            405                 410                 415

Asp Lys Asp Leu Val Leu Glu Lys Leu Lys Val Leu Lys Lys Ser Leu
            420                 425                 430

Glu His Gln Arg Ala Arg Val Ser Ile Ile Glu Ala Leu Ser Gly
            435                 440                 445

Asp Lys Glu Glu Lys Ser Arg Glu Glu Leu Leu Glu Met Val Glu
            450                 455                 460

Lys Leu Lys Ile Glu Leu Glu Thr Glu Lys Leu Lys Thr Leu Arg Ala
```

Asp Lys Asp Ser Val Leu Gly
              485

<210> SEQ ID NO 3
<211> LENGTH: 52
<212> TYPE: DNA
<213> ORGANISM: Artificial sequence
<220> FEATURE:
<223> OTHER INFORMATION: primer: prm03186

<400> SEQUENCE: 3
ggggacaagt ttgtacaaaa aagcaggctt cacaatggct cggaacaagc tc            52

<210> SEQ ID NO 4
<211> LENGTH: 56
<212> TYPE: DNA
<213> ORGANISM: Artificial sequence
<220> FEATURE:
<223> OTHER INFORMATION: primer: prm03187

<400> SEQUENCE: 4
ggggaccact ttgtacaaga aagctgggta atagttaacc caaaacacta tcttta        56

<210> SEQ ID NO 5
<211> LENGTH: 3710
<212> TYPE: DNA
<213> ORGANISM: Artificial sequence
<220> FEATURE:
<223> OTHER INFORMATION: expression cassette

<400> SEQUENCE: 5

| | | | |
|---|---|---|---|
| aatccgaaaa gtttctgcac cgttttcacc ccctaactaa caatataggg aacgtgtgct |  |  | 60 |
| aaatataaaa tgagacctta tatatgtagc gctgataact agaactatgc aagaaaaact |  |  | 120 |
| catccaccta ctttagtggc aatcgggcta aataaaaaag agtcgctaca ctagtttcgt |  |  | 180 |
| tttccttagt aattaagtgg gaaaatgaaa tcattattgc ttagaatata cgttcacatc |  |  | 240 |
| tctgtcatga agttaaatta ttcgaggtag ccataattgt catcaaactc ttcttgaata |  |  | 300 |
| aaaaaatctt tctagctgaa ctcaatgggt aaagagagag attttttta aaaaaataga |  |  | 360 |
| atgaagatat tctgaacgta ttggcaaaga tttaaacata taattatata attttatagt |  |  | 420 |
| ttgtgcattc gtcatatcgc acatcattaa ggacatgtct tactccatcc caatttttat |  |  | 480 |
| ttagtaatta aagacaattg acttattttt attatttatc tttttcgat tagatgcaag |  |  | 540 |
| gtacttacgc acacactttg tgctcatgtg catgtgtgag tgcacctcct caatacacgt |  |  | 600 |
| tcaactagca acacatctct aatatcactc gcctatttaa tacatttagg tagcaatatc |  |  | 660 |
| tgaattcaag cactccacca tcaccagacc acttttaata atatctaaaa tacaaaaaat |  |  | 720 |
| aattttacag aatagcatga aaagtatgaa acgaactatt taggttttc acatacaaaa |  |  | 780 |
| aaaaaagaa ttttgctcgt gcgcgagcgc caatctccca tattgggcac acaggcaaca |  |  | 840 |
| acagagtggc tgcccacaga acaacccaca aaaaacgatg atctaacgga ggacagcaag |  |  | 900 |
| tccgcaacaa cctttaaca gcaggctttg cggccaggag agaggaggag aggcaaagaa |  |  | 960 |
| aaccaagcat cctcctcctc ccatctataa attcctcccc cctttcccc tctctatata |  |  | 1020 |
| ggaggcatcc aagccaagaa gagggagagc accaaggaca cgcgactagc agaagccgag |  |  | 1080 |
| cgaccgcctt cttcgatcca tatcttccgg tcgagttctt ggtcgatctc ttccctcctc |  |  | 1140 |
| cacctcctcc tcacagggta tgtgcccttc ggttgttctt ggatttattg ttctaggttg |  |  | 1200 |
| tgtagtacgg gcgttgatgt taggaaaggg gatctgtatc tgtgatgatt cctgttcttg |  |  | 1260 |

```
gatttgggat agaggggttc ttgatgttgc atgttatcgg ttcggtttga ttagtagtat   1320
ggttttcaat cgtctggaga gctctatgga aatgaaatgg tttagggtac ggaatcttgc   1380
gattttgtga gtaccttttg tttgaggtaa aatcagagca ccggtgattt tgcttggtgt   1440
aataaaagta cggttgtttg gtcctcgatt ctggtagtga tgcttctcga tttgacgaag   1500
ctatcctttg tttattccct attgaacaaa aataatccaa cttttgaagac ggtcccgttg   1560 atgagattga atgattgatt cttaagcctg tccaaaattt cgcagctggc ttgtttagat   1620
acagtagtcc ccatcacgaa attcatggaa acagttataa tcctcaggaa caggggattc   1680
cctgttcttc cgatttgctt tagtcccaga atttttttc ccaaatatct aaaaagtca    1740 ctttctggtt cagttcaatg aattgattgc tacaaataat gcttttatag cgttatccta   1800
gctgtagttc agttaatagg taataccct atagtttagt caggagaaga acttatccga    1860
tttctgatct ccattttaa ttatatgaaa tgaactgtag cataagcagt attcatttgg    1920 attattttt ttattagctc tcaccccttc attattctga gctgaaagtc tggcatgaac    1980
tgtcctcaat tttgttttca aattcacatc gattatctat gcattatcct cttgtatcta   2040
cctgtagaag tttcttttg gttattcctt gactgcttga ttacagaaag aaatttatga    2100
agctgtaatc gggatagtta tactgcttgt tcttatgatt catttccttt gtgcagttct   2160
tggtgtagct tgccactttc accagcaaag ttcatttaaa tcaactaggg atatcacaag   2220
tttgtacaaa aaagcaggct tcacaatggc tcggaacaag ctcgagttcc ctcttgatgc   2280
tgaagcctac gagatcatct gcaagatagg cgttggtgtt agtgcttcgg tctacaaggc   2340
catatgcatt ccgatgaact caatggtagt tgctatcaaa gccatcgatc ttgatcagtc   2400
gcgggctgac tttgacagtc ttcgccgtga aaccaagacg atgtctctgc tttctcatcc   2460
gaatattctc aatgcttatt gttcattcac cgttgatcga tgtctctggg tggttatgcc   2520
attcatgtct tgtggctctc ttcattcgat cgtctcttcg tcttttccaa gtgggttacc   2580
agaaaactgc atttccgtct tcctcaagga aactctgaat gcaatctcgt atcttcacga   2640
tcagggtcat ttgcaccgtg acatcaaggc aggtaacatt ctggtagatt ctgatggatc   2700
cgtgaagctc gctgatttcg gagtatctgc atccatctat gaacccgtga catcttcctc   2760
tggaacaaca tcttcttctt taaggttaac tgatatagcg ggaacaccgt attggatggc   2820
tccggaagtg gttcattccc acacagggta tggtttcaaa gcagacattt ggtctttcgg   2880
gataacagcg ttggagttag cacatggaag acctccgtta tctcacttac cgccgttgaa   2940
gagtctgctc atgaagatca ccaaaaggtt tcatttttct gattacgaga tcaatacgag   3000
cggaagcagc aaaaagggta acaagaagtt ctcaaaagct tttagagaaa tggttggttt   3060
gtgtctagag caagatccta ctaaaagacc atcggcagag aagttgttga agcatccttt   3120
tttcaagaac tgtaaaggac tcgactttgt ggtcaagaac gtgttgcata gcttgtcaaa   3180
cgcagagcag atgtttatgg agagtcagat tttgatcaag agtgttggag atgatgatga   3240
agaagaagaa gaagaagacg aagagatagt gaagaataga agaatcagtg ggtggaattt   3300
ccgtgaagac gatctccaac ttagtccagt gttcccagct actgaatcag actcttctga   3360
gtccagtcca cgtgaagaag atcaatcaaa agacaaaaag gaagacgata acgtcacaat   3420 aacgggtat gaactcggtt taggtttgtc gaacgaggaa gctaagaacc aagaaggtga    3480
ggttgttggg tttgataaag atttggtgtt agagaaactg aaagtgttga agaaaagttt   3540
agagcatcaa agagcaagag tgtcgattat aatcgagca ttgagtgggg acaaggaaga    3600
gaagagcaga gaagaagagc ttctagagat ggtggagaag ttaaagattg aattggaaac   3660
```
tgagaagcta aagaccttgc gtgctgataa agatagtgtt ttgggttaac    3710

<210> SEQ ID NO 6
<211> LENGTH: 10
<212> TYPE: PRT
<213> ORGANISM: Artificial sequence
<220> FEATURE:
<223> OTHER INFORMATION: ste20 signature sequence
<220> FEATURE:
<221> NAME/KEY: MISC_FEATURE
<222> LOCATION: (2)..(2)
<223> OTHER INFORMATION: Xaa can be Thr or Asn
<220> FEATURE:
<221> NAME/KEY: MISC_FEATURE
<222> LOCATION: (4)..(4)
<223> OTHER INFORMATION: Xaa can be Tyr, Cys or Arg
<220> FEATURE:
<221> NAME/KEY: MISC_FEATURE
<222> LOCATION: (5)..(5)
<223> OTHER INFORMATION: Xaa can be Trp or Arg
<220> FEATURE:
<221> NAME/KEY: MISC_FEATURE
<222> LOCATION: (10)..(10)
<223> OTHER INFORMATION: Xaa can be Val or Lys

<400> SEQUENCE: 6

Gly Xaa Pro Xaa Xaa Met Ala Pro Glu Xaa
1               5                   10

<210> SEQ ID NO 7
<211> LENGTH: 10
<212> TYPE: PRT
<213> ORGANISM: Artificial sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be Ser, His or Asn
<220> FEATURE:
<221> NAME/KEY: MISC_FEATURE
<222> LOCATION: (2)..(2)
<223> OTHER INFORMATION: Xaa can be Ile or LEu
<220> FEATURE:
<221> NAME/KEY: MISC_FEATURE
<222> LOCATION: (3)..(3)
<223> OTHER INFORMATION: Xaa can be Val, Ile, Leu or Met
<220> FEATURE:
<221> NAME/KEY: MISC_FEATURE
<222> LOCATION: (4)..(4)
<223> OTHER INFORMATION: Xaa can be Ser or Lys
<220> FEATURE:
<221> NAME/KEY: MISC_FEATURE
<222> LOCATION: (5)..(5)
<223> OTHER INFORMATION: Xaa can be Ser, His, Thr, Ala, Ile or Val
<220> FEATURE:
<221> NAME/KEY: MISC_FEATURE
<222> LOCATION: (6)..(6)
<223> OTHER INFORMATION: Xaa can be Ser, Gly, Val or Ala
<220> FEATURE:
<221> NAME/KEY: MISC_FEATURE
<222> LOCATION: (7)..(7)
<223> OTHER INFORMATION: Xaa can be Phe or Tyr
<220> FEATURE:
<221> NAME/KEY: MISC_FEATURE
<222> LOCATION: (8)..(8)
<223> OTHER INFORMATION: Xaa can be Pro or Gln
<220> FEATURE:
<221> NAME/KEY: MISC_FEATURE
<222> LOCATION: (9)..(9)
<223> OTHER INFORMATION: Xaa can be Ser, Asn, Asp or Glu

<400> SEQUENCE: 7

Xaa Xaa Xaa Xaa Xaa Xaa Xaa Xaa Xaa Gly
1               5                   10

```
<210> SEQ ID NO 8
<211> LENGTH: 9
<212> TYPE: PRT
<213> ORGANISM: Artificial sequence
<220> FEATURE:
<223> OTHER INFORMATION: consensus sequence
<220> FEATURE:
<221> NAME/KEY: MISC_FEATURE
<222> LOCATION: (1)..(1)
<223> OTHER INFORMATION: Xaa can be Val or Ile
<220> FEATURE:
<221> NAME/KEY: MISC_FEATURE
<222> LOCATION: (5)..(5)
<223> OTHER INFORMATION: Xaa can be Thr, Asn or Val
<220> FEATURE:
<221> NAME/KEY: MISC_FEATURE
<222> LOCATION: (8)..(8)
<223> OTHER INFORMATION: Xaa can be Gly or Ser
<220> FEATURE:
<221> NAME/KEY: MISC_FEATURE
<222> LOCATION: (9)..(9)
<223> OTHER INFORMATION: Xaa can be Phe or Ile

<400> SEQUENCE: 8

Xaa His Ser His Xaa Gly Tyr Xaa Xaa
1               5

<210> SEQ ID NO 9
<211> LENGTH: 12
<212> TYPE: PRT
<213> ORGANISM: Artificial sequence
<220> FEATURE:
<223> OTHER INFORMATION: consensus sequence
<220> FEATURE:
<221> NAME/KEY: MISC_FEATURE
<222> LOCATION: (10)..(10)
<223> OTHER INFORMATION: Xaa can be Leu or Ser

<400> SEQUENCE: 9

Arg Pro Pro Leu Ser His Leu Pro Pro Xaa Lys Ser
1               5                   10

<210> SEQ ID NO 10
<211> LENGTH: 8
<212> TYPE: PRT
<213> ORGANISM: Artificial sequence
<220> FEATURE:
<223> OTHER INFORMATION: consensus sequence

<400> SEQUENCE: 10

Arg Arg Ile Ser Gly Trp Asn Phe
1               5

<210> SEQ ID NO 11
<211> LENGTH: 2772
<212> TYPE: DNA
<213> ORGANISM: Arabidopsis thaliana

<400> SEQUENCE: 11
cagacgacag aaaagctaac cacaagagga ggagagaaac tcgataacaa acaagagaaa      60
gagaaagcga gattctaaaa tctaatctcg tgcttccaat tcaaataatt ttgtctcctt     120
agcggatcga tcgtagatta taaagctccg ccgtcgcctc cgccgcaatc gacggcggtg     180
tctacgtcgc tttcgtttcg tgcgtaacag gaggagcagc agcaaaataa gtcagcttaa     240
gtaacgccgt ctttgatttg acttgagata agtattttgg tgatatggca ttgatgatgt     300
ttccgcattt gctcgacgtt gacgaaaagt aaaatgctgg cgaattggaa gaaaccacat     360
```

```
acagattgat gctctcttca gtcgacctct tttgtaaatt tgttgaaact tacggggtcg    420
aaggtgtgta gcatatatgc tataagaaga ttataaagta aaaattatgg aatcgggttc    480
agagaaaaag ttccctctca atgcaaaaga ctacaagtta tatgaagaaa ttggagatgg    540
tgtcagtgcg actgtgcata gagctttgtg tataccgctt aatgtggtag ttgctatcaa    600
ggttcttgat ctggaaaagt gcaacaacga tctggatggg atccggagag aggtgcaaac    660
aatgagtctg atcaaccatc caaatgtgtt gcaagctcat tgctcattta ccaccggaca    720
ccagctttgg gttgtgatgc cttacatggc tggaggatct tgtctccata taattaagtc    780
ttcctatcca gatggatttg aggaacctgt tatcgctact ttacttcgtg agactctgaa    840
agctcttgta tatcttcatg ctcatgggca tatccacagg gatgtgaagg ctggaaacat    900
tttattggat tccaatggtg ccgttaagtt agcagacttt ggagtatcag cttgcatgtt    960
tgatacggga gatagacaac gttccagaaa tacatttgtt gggactccat gctggatggc   1020
tcctgaagtc atgcagcaac tacatggata tgatttcaaa gcagatgtat ggtcatttgg   1080
aataacagca cttgaattgg cacatggtca tgccccattt tccaaatatc cgccaatgaa   1140
ggttttgctg atgaccttac aaaatgcacc tcctggactt gactacgaga gagacaaaag   1200
attctcgaaa gccttcaagg aaatggtggg tacatgcctg gtgaaggacc caagaagcg    1260 tccaacttca gaaaagcttt tgaaacaccc tttcttcaaa catgcacgtc cagctgatta   1320
cctggttaaa acaattctaa atggtcttcc tccattaggt gatcgctata gacaaataaa   1380
gtcgaaggaa gctgatctcc taatgcaaaa caaatctgaa tatgaagcgc acttatcaca   1440
gcaagagtat ataaggggaa taagcgcttg gaatttcaat ctcgaggacc taaaaactca   1500 agctgcccctt atttcagatg atgatacttc acatgctgaa gagcccgatt tcaaccaaaa   1560
gcaatgtgaa agacaggatg aatctgctct ttcccctgaa agggctagca gctcagcaac   1620
agctcctagt caagatgacg aactgaatga tattcatgat ttagagagtt ctttcgcctc   1680
atttccaatc aaacctcttc aagcactaaa aggctgcttt gatatcagtg aggacgagga   1740
taatgcaact actcctgatt ggaaagatgc taatgtaaat tctggacaac agctttttaac   1800 aaaggcttcc attggatctt tggccgaaac cacgaaagaa gaggacactg cagcacaaaa   1860
cacttcttta ccacgtcatg tcatttctga acagaaaaaa tatttgagcg gttcaattat   1920
accagagagt actttctctc caaaaagaat cacatctgat gctgataggg agtttccaaca   1980 gcgtagatat caaacagagc ggagctacag cggatcatta taccgcacca agagagattc   2040
cgtggacgag acgtcagaag tcccgcatgt ggagcacaag ggacggttta aggtcacatc   2100
agcagatctg agtcccaagg gatctacaaa ctctacattc acaccattta gtggtggtac   2160
aagcagccct agttgcctca atgctacaac cgcctcaatc ctcccatcaa ttcagtcgat   2220
tttgcagcaa aatgctatgc aacgggaaga gattttgaga ctaatcaaat acttggagca   2280
aacctctgcc aagcaacctg gatcgcctga cgaacgtc gatgacctat tgcagacgcc   2340
tcctgcaacc tcacgagaga gagaacttca gtctcaagtc atgctactac aacaaagctt   2400
ttccagccta acagaagaac taagaaaaca gaagcagaaa aatgggcagt ggagaatca   2460 gttgaacgca ttaacacaca gaaatgattg agtctcaaaa gccatcgaga caaggctgag   2520
agatacaact ggggatcttg agttaaaaaa acacaaaatt ccctttcaag gcaaaaagaa   2580
gaaatagaga agatttgtgt gctttatatt tctattgggt gtaatttgtt tgacaggttt   2640
atattatgtg acaactacta cagtgatttt cttattttg gggaagtttt ccccactttt   2700
cttttttact tatttgtgtt ttatgatatg ctatgtaaac aaaatactat tgtttaatta   2760
```
tgtttctgtg tg                                                         2772

<210> SEQ ID NO 12
<211> LENGTH: 674
<212> TYPE: PRT
<213> ORGANISM: Arabidopsis thaliana

<400> SEQUENCE: 12

Met Glu Ser Ser Glu Lys Lys Phe Pro Leu Asn Ala Lys Asp Tyr
1               5                   10                  15

Lys Leu Tyr Glu Glu Ile Gly Asp Gly Val Ser Ala Thr Val His Arg
            20                  25                  30

Ala Leu Cys Ile Pro Leu Asn Val Val Ala Ile Lys Val Leu Asp
        35                  40                  45

Leu Glu Lys Cys Asn Asn Asp Leu Asp Gly Ile Arg Arg Glu Val Gln
    50                  55                  60

Thr Met Ser Leu Ile Asn His Pro Asn Val Leu Gln Ala His Cys Ser
65                  70                  75                  80

Phe Thr Thr Gly His Gln Leu Trp Val Val Met Pro Tyr Met Ala Gly
                85                  90                  95

Gly Ser Cys Leu His Ile Ile Lys Ser Ser Tyr Pro Asp Gly Phe Glu
            100                 105                 110

Glu Pro Val Ile Ala Thr Leu Leu Arg Glu Thr Leu Lys Ala Leu Val
        115                 120                 125

Tyr Leu His Ala His Gly His Ile His Arg Asp Val Lys Ala Gly Asn
    130                 135                 140

Ile Leu Leu Asp Ser Asn Gly Ala Val Lys Leu Ala Asp Phe Gly Val
145                 150                 155                 160

Ser Ala Cys Met Phe Asp Thr Gly Asp Arg Gln Arg Ser Arg Asn Thr
                165                 170                 175

Phe Val Gly Thr Pro Cys Trp Met Ala Pro Glu Val Met Gln Gln Leu
            180                 185                 190

His Gly Tyr Asp Phe Lys Ala Asp Val Trp Ser Phe Gly Ile Thr Ala
        195                 200                 205

Leu Glu Leu Ala His Gly His Ala Pro Phe Ser Lys Tyr Pro Pro Met
    210                 215                 220

Lys Val Leu Leu Met Thr Leu Gln Asn Ala Pro Pro Gly Leu Asp Tyr
225                 230                 235                 240

Glu Arg Asp Lys Arg Phe Ser Lys Ala Phe Lys Glu Met Val Gly Thr
                245                 250                 255

Cys Leu Val Lys Asp Pro Lys Lys Arg Pro Thr Ser Glu Lys Leu Leu
            260                 265                 270

Lys His Pro Phe Phe Lys His Ala Arg Pro Ala Asp Tyr Leu Val Lys
        275                 280                 285

Thr Ile Leu Asn Gly Leu Pro Pro Leu Gly Asp Arg Tyr Arg Gln Ile
    290                 295                 300

Lys Ser Lys Glu Ala Asp Leu Leu Met Gln Asn Lys Ser Glu Tyr Glu
305                 310                 315                 320

Ala His Leu Ser Gln Gln Glu Tyr Ile Arg Gly Ile Ser Ala Trp Asn
                325                 330                 335

Phe Asn Leu Glu Asp Leu Lys Thr Gln Ala Ala Leu Ile Ser Asp Asp
            340                 345                 350

Asp Thr Ser His Ala Glu Glu Pro Asp Phe Asn Gln Lys Gln Cys Glu
        355                 360                 365

Arg Gln Asp Glu Ser Ala Leu Ser Pro Glu Arg Ala Ser Ser Ser Ala

```
                370             375             380
Thr Ala Pro Ser Gln Asp Asp Glu Leu Asn Asp Ile His Asp Leu Glu
385                 390                 395                 400

Ser Ser Phe Ala Ser Phe Pro Ile Lys Pro Leu Gln Ala Leu Lys Gly
                405                 410                 415

Cys Phe Asp Ile Ser Glu Asp Glu Asp Asn Ala Thr Thr Pro Asp Trp
                420                 425                 430

Lys Asp Ala Asn Val Asn Ser Gly Gln Gln Leu Leu Thr Lys Ala Ser
                435                 440                 445

Ile Gly Ser Leu Ala Glu Thr Thr Lys Glu Glu Asp Thr Ala Ala Gln
450                 455                 460

Asn Thr Ser Leu Pro Arg His Val Ile Ser Glu Gln Lys Lys Tyr Leu
465                 470                 475                 480

Ser Gly Ser Ile Ile Pro Glu Ser Thr Phe Ser Pro Lys Arg Ile Thr
                485                 490                 495

Ser Asp Ala Asp Arg Glu Phe Gln Gln Arg Arg Tyr Gln Thr Glu Arg
                500                 505                 510

Ser Tyr Ser Gly Ser Leu Tyr Arg Thr Lys Arg Asp Ser Val Asp Glu
                515                 520                 525

Thr Ser Glu Val Pro His Val Glu His Lys Gly Arg Phe Lys Val Thr
530                 535                 540

Ser Ala Asp Leu Ser Pro Lys Gly Ser Thr Asn Ser Thr Phe Thr Pro
545                 550                 555                 560

Phe Ser Gly Gly Thr Ser Ser Pro Ser Cys Leu Asn Ala Thr Ala
                565                 570                 575

Ser Ile Leu Pro Ser Ile Gln Ser Ile Leu Gln Gln Asn Ala Met Gln
                580                 585                 590

Arg Glu Glu Ile Leu Arg Leu Ile Lys Tyr Leu Glu Gln Thr Ser Ala
                595                 600                 605

Lys Gln Pro Gly Ser Pro Glu Thr Asn Val Asp Asp Leu Leu Gln Thr
610                 615                 620

Pro Pro Ala Thr Ser Arg Glu Arg Glu Leu Gln Ser Gln Val Met Leu
625                 630                 635                 640

Leu Gln Gln Ser Phe Ser Ser Leu Thr Glu Glu Leu Lys Lys Gln Lys
                645                 650                 655

Gln Lys Asn Gly Gln Leu Glu Asn Gln Leu Asn Ala Leu Thr His Arg
                660                 665                 670

Asn Asp

<210> SEQ ID NO 13
<211> LENGTH: 1785
<212> TYPE: DNA
<213> ORGANISM: Arabidopsis thaliana

<400> SEQUENCE: 13
atggctggtt catcaacgaa acgatttcct ctatatgcta aagattatga gctctttgaa     60
gaggtaggag aaggtgttag tgctactgtg tatagagctc gttgcattgc tcttaacgag    120
attgtcgctg ttaaaatctt ggatctcgaa aaatgcagga atgatttgga acaatacgc    180 aaggaagttc atataatgag tttgattgat catccgaatt tattgaaagc gcattgttcg    240
tttatcgaca gtagtagttt gtggattgta atgccttata tgtcgggtgg ttcttgtttt    300
catttaatga aatctgtata tccggaaggt cttgagcaac ctataattgc acttttgttg    360
agggaagtgc ttaaagctct tgtttatctt catagacaag gtcacatcca tagagatgtt    420
```

```
aaggctggga atatattgat tcactcaaaa ggcgtagtta aacttggaga ctttggagtt    480
tcagcatgta tgtttgatag tggagaaaga atgcaaacaa ggaatacatt cgttgggact    540
ccttgttgga tggcacctga ggttatgcag caactagatg gatatgattt caagtatctt    600
gctcatggtc atgccccatt ttccaaatat ccacctatga aggtgctact aatgacatta    660
caaaatgcac tcctcgtct agactatgac agagataaga aattctcaaa gtcatttaga     720
gagttaatcg cagcgtgctt agttaaagat ccgaaaaagc gtccaactgc agcaaaactt    780
ctgaaacatc ctttcttcaa acatgctcgg tctacagatt atttgtcccg taaaattctt    840
catggtcttt ctccacttgg tgaacgtttt aaaaagctca aggaggcaga ggctgagttg    900
ttcaaaggca taaatggtga caaagaacag ttgtctcagc atgagtatat gagaggaatt    960
agtgcttgga actttgatct tgaagcattg agaaggcagg catcacttgt aattattcca   1020
aatgaagaaa tctataattc agagatacag gaactgaaca gaaatggaga tgtaccaaaa   1080
ggaaaaccag tgatacaaag gtcacagact atgcctttgg aatatttctc agaaaaggca   1140
agtgatatgg tgagtgagag tagcagtcaa ttaaccggtt cattacttcc ttcgtttcat   1200
cgcaaattcc tcccggctct tggcaatgca tgtaactcga gcgatagagc agcagagaag   1260
ctcgcttttg aagagccacg tcaagtacta cacccattag cggatacaaa gaaaattaga   1320
aaagcaggaa gtgatcagca ggagaaacca aaaaatggtt acgcagatag tcctgtgaac   1380
cgtgaatctt ccacattatc aaaggaacca ttagcggata caaagcaagt tagaaaacca   1440
ggaaatgagc aggagaaacc aaaaaacggc tatatagtta gtcatgtgaa ccgtgaatct   1500
tccacatcag aggaaatcct cccactgttg cagagtctcc tggttcagaa tgacattcaa   1560
agggcgcaag taatcaggtt aattagatttt tttgatcgaa ctgcgaaaac ggaaaatcca   1620
atctcaaaaa ccgaaggagt gcaggagaaa gatctgcaat ctcaagttca gttttggag   1680
caaagtgttg agaagcttgt agaggaagtt cagagaagaa aagatataaa tagtcagcta   1740
gagcaacaga tcagctctct gattagcagc aacaacatct cttaa                   1785
```

<210> SEQ ID NO 14
<211> LENGTH: 594
<212> TYPE: PRT
<213> ORGANISM: Arabidopsis thaliana

<400> SEQUENCE: 14

```
Met Ala Gly Ser Ser Thr Lys Arg Phe Pro Leu Tyr Ala Lys Asp Tyr
1               5                   10                  15

Glu Leu Phe Glu Glu Val Gly Glu Gly Val Ser Ala Thr Val Tyr Arg
            20                  25                  30

Ala Arg Cys Ile Ala Leu Asn Glu Ile Val Ala Val Lys Ile Leu Asp
        35                  40                  45

Leu Glu Lys Cys Arg Asn Asp Leu Glu Thr Ile Arg Lys Glu Val His
    50                  55                  60

Ile Met Ser Leu Ile Asp His Pro Asn Leu Leu Lys Ala His Cys Ser
65                  70                  75                  80

Phe Ile Asp Ser Ser Leu Trp Ile Val Met Pro Tyr Met Ser Gly
                85                  90                  95

Gly Ser Cys Phe His Leu Met Lys Ser Val Tyr Pro Glu Gly Leu Glu
            100                 105                 110

Gln Pro Ile Ile Ala Thr Leu Arg Glu Val Leu Lys Ala Leu Val
        115                 120                 125

Tyr Leu His Arg Gln Gly His Ile His Arg Asp Val Lys Ala Gly Asn
    130                 135                 140
```

```
Ile Leu Ile His Ser Lys Gly Val Val Lys Leu Gly Asp Phe Gly Val
145                 150                 155                 160

Ser Ala Cys Met Phe Asp Ser Gly Glu Arg Met Gln Thr Arg Asn Thr
                165                 170                 175

Phe Val Gly Thr Pro Cys Trp Met Ala Pro Glu Val Met Gln Gln Leu
            180                 185                 190

Asp Gly Tyr Asp Phe Lys Tyr Leu Ala His Gly His Ala Pro Phe Ser
        195                 200                 205

Lys Tyr Pro Pro Met Lys Val Leu Leu Met Thr Leu Gln Asn Ala Pro
    210                 215                 220

Pro Arg Leu Asp Tyr Asp Arg Asp Lys Lys Phe Ser Lys Ser Phe Arg
225                 230                 235                 240

Glu Leu Ile Ala Ala Cys Leu Val Lys Asp Pro Lys Lys Arg Pro Thr
                245                 250                 255

Ala Ala Lys Leu Leu Lys His Pro Phe Phe Lys His Ala Arg Ser Thr
                260                 265                 270

Asp Tyr Leu Ser Arg Lys Ile Leu His Gly Leu Ser Pro Leu Gly Glu
        275                 280                 285

Arg Phe Lys Lys Leu Lys Glu Ala Glu Ala Glu Leu Phe Lys Gly Ile
290                 295                 300

Asn Gly Asp Lys Glu Gln Leu Ser Gln His Glu Tyr Met Arg Gly Ile
305                 310                 315                 320

Ser Ala Trp Asn Phe Asp Leu Glu Ala Leu Arg Arg Gln Ala Ser Leu
                325                 330                 335

Val Ile Ile Pro Asn Glu Glu Ile Tyr Asn Ser Glu Ile Gln Glu Leu
                340                 345                 350

Asn Arg Asn Gly Asp Val Pro Lys Gly Lys Pro Val Ile Gln Arg Ser
            355                 360                 365

Gln Thr Met Pro Leu Glu Tyr Phe Ser Glu Lys Ala Ser Asp Met Val
370                 375                 380

Ser Glu Ser Ser Ser Gln Leu Thr Gly Ser Leu Leu Pro Ser Phe His
385                 390                 395                 400

Arg Lys Phe Leu Pro Ala Leu Gly Asn Ala Cys Asn Ser Ser Asp Arg
                405                 410                 415

Ala Ala Glu Lys Leu Ala Phe Glu Pro Arg Gln Val Leu His Pro
                420                 425                 430

Leu Ala Asp Thr Lys Lys Ile Arg Lys Ala Gly Ser Asp Gln Gln Glu
            435                 440                 445

Lys Pro Lys Asn Gly Tyr Ala Asp Ser Pro Val Asn Arg Glu Ser Ser
    450                 455                 460

Thr Leu Ser Lys Glu Pro Leu Ala Asp Thr Lys Gln Val Arg Lys Pro
465                 470                 475                 480

Gly Asn Glu Gln Glu Lys Pro Lys Asn Gly Tyr Ile Val Ser His Val
                485                 490                 495

Asn Arg Glu Ser Ser Thr Ser Glu Glu Ile Leu Pro Leu Leu Gln Ser
            500                 505                 510

Leu Leu Val Gln Asn Asp Ile Gln Arg Ala Gln Val Ile Arg Leu Ile
            515                 520                 525

Arg Phe Phe Asp Arg Thr Ala Lys Thr Glu Asn Pro Ile Ser Lys Thr
            530                 535                 540

Glu Gly Val Gln Glu Lys Asp Leu Gln Ser Gln Val Gln Phe Leu Glu
545                 550                 555                 560

Gln Ser Val Glu Lys Leu Val Glu Glu Val Gln Arg Arg Lys Asp Ile
```

565                 570                 575
Asn Ser Gln Leu Glu Gln Gln Ile Ser Ser Leu Ile Ser Asn Asn
            580                 585                 590

Ile Ser

<210> SEQ ID NO 15
<211> LENGTH: 1422
<212> TYPE: DNA
<213> ORGANISM: Arabidopsis thaliana

<400> SEQUENCE: 15

| | | | | | |
|---|---|---|---|---|---|
| atgacgagtt | caccggaaac | gagatttcct | ctggttgcga | agattacga | gattttagaa | 60 |
| gagataggcg | atggtgttta | cagagctcga | tgcattctac | ttgatgaaat | tgtagccatc | 120 |
| aagatctgga | accttgaaaa | atgcaccaac | gatctggaaa | ccataaggaa | agaagttcat | 180 |
| agattgagct | taattgatca | tccaaatcta | ttgagggtgc | attgctcttt | catagatagt | 240 |
| agcagcttgt | ggattgtgat | gccttttatg | tcgtgcggct | cttccttgaa | cataatgaaa | 300 |
| tcagtctatc | caaatggtct | tgaggaacct | gtaattgcta | tattgttgcg | ggagattctt | 360 |
| aaagctcttg | tttaccttca | tggactagga | cacatccatc | gaatgttaa | ggctgggaat | 420 |
| gtactggttg | actcagaagg | aactgttaag | ctcggtgact | ttgaagtttc | agcatccatg | 480 |
| tttgatagtg | tggaaaggat | gcgtactagt | tctgagaata | cttttgttgg | aaatccacgc | 540 |
| cggatggcac | ctgagaagga | tatgcagcaa | gttgatggct | atgatttcaa | agtggatatc | 600 |
| tggtcgtttg | gcatgactgc | cctggaactt | gcccatggtc | attcacctac | acgggtgcta | 660 |
| ccattgaact | tacaaaattc | tcccttcct | aactatgaag | aagacacgaa | attctctaag | 720 |
| tcttttagag | agttggtcgc | agcttgcttg | atagaagatc | cagaaaaacg | tccgaccgct | 780 |
| tcacaactac | tggaatatcc | gttcttacag | caaactcttt | ctactgaata | cttggctagt | 840 |
| acatttcttg | atggcctctc | tccgcttggt | gagcgttata | gaaagctgaa | ggaggaaaag | 900 |
| gccaagttgg | ttaaaggtgt | agatggtaac | aaggagaaag | tatctcagga | aaatgttgaa | 960 |
| gcgctgctga | tggaacctgc | tagtcttgtg | aaccctgttt | cttgtgatac | tgctcaagtc | 1020 |
| ctcccaatct | tacagaatat | cctgatccaa | aatgatatcc | aaagggaaaa | tgttgaagcg | 1080 |
| ctgctgacgg | aacctgctat | tcttgtgaac | cctgtttctt | gtgatactgc | tcaagtcctc | 1140 |
| ccaatcgtac | agaatatcct | gatccagaat | gatatccaaa | ggaaaaggtt | aatcggttta | 1200 |
| atgcaactct | gtgatccaac | tgctggtaag | tttgctgttc | tatcactaga | atttgcatct | 1260 |
| tctctatgtt | acaagttcca | tgacctgatc | ttgattttg | tacagaaatc | agaattccga | 1320 |
| ttggcaatac | agaagttggg | cagatatcaa | caacagagac | agatctattg | tctgaggttc | 1380 |
| acgttttgca | gcagaggtaa | tgataaattc | cacaagcttt | aa | | 1422 |

<210> SEQ ID NO 16
<211> LENGTH: 473
<212> TYPE: PRT
<213> ORGANISM: Arabidopsis thaliana

<400> SEQUENCE: 16

Met Thr Ser Ser Pro Glu Thr Arg Phe Pro Leu Val Ala Lys Asp Tyr
1               5                   10                  15

Glu Ile Leu Glu Glu Ile Gly Asp Gly Val Tyr Arg Ala Arg Cys Ile
            20                  25                  30

Leu Leu Asp Glu Ile Val Ala Ile Lys Ile Trp Asn Leu Glu Lys Cys
        35                  40                  45

```
Thr Asn Asp Leu Glu Thr Ile Arg Lys Glu Val His Arg Leu Ser Leu
 50                  55                  60

Ile Asp His Pro Asn Leu Leu Arg Val His Cys Ser Phe Ile Asp Ser
 65                  70                  75                  80

Ser Ser Leu Trp Ile Val Met Pro Phe Met Ser Cys Gly Ser Ser Leu
                 85                  90                  95

Asn Ile Met Lys Ser Val Tyr Pro Asn Gly Leu Glu Glu Pro Val Ile
            100                 105                 110

Ala Ile Leu Leu Arg Glu Ile Leu Lys Ala Leu Val Tyr Leu His Gly
            115                 120                 125

Leu Gly His Ile His Arg Asn Val Lys Ala Gly Asn Val Leu Val Asp
        130                 135                 140

Ser Glu Gly Thr Val Lys Leu Gly Asp Phe Glu Val Ser Ala Ser Met
145                 150                 155                 160

Phe Asp Ser Val Glu Arg Met Arg Thr Ser Ser Glu Asn Thr Phe Val
                165                 170                 175

Gly Asn Pro Arg Arg Met Ala Pro Glu Lys Asp Met Gln Gln Val Asp
            180                 185                 190

Gly Tyr Asp Phe Lys Val Asp Ile Trp Ser Phe Gly Met Thr Ala Leu
        195                 200                 205

Glu Leu Ala His Gly His Ser Pro Thr Thr Val Leu Pro Leu Asn Leu
    210                 215                 220

Gln Asn Ser Pro Phe Pro Asn Tyr Glu Glu Asp Thr Lys Phe Ser Lys
225                 230                 235                 240

Ser Phe Arg Glu Leu Val Ala Ala Cys Leu Ile Glu Asp Pro Glu Lys
                245                 250                 255

Arg Pro Thr Ala Ser Gln Leu Leu Glu Tyr Pro Phe Leu Gln Gln Thr
            260                 265                 270

Leu Ser Thr Glu Tyr Leu Ala Ser Thr Phe Leu Asp Gly Leu Ser Pro
        275                 280                 285

Leu Gly Glu Arg Tyr Arg Lys Leu Lys Glu Glu Lys Ala Lys Leu Val
    290                 295                 300

Lys Gly Val Asp Gly Asn Lys Glu Lys Val Ser Gln Glu Asn Val Glu
305                 310                 315                 320

Ala Leu Leu Met Glu Pro Ala Ser Leu Val Asn Pro Val Ser Cys Asp
                325                 330                 335

Thr Ala Gln Val Leu Pro Ile Leu Gln Asn Ile Leu Ile Gln Asn Asp
            340                 345                 350

Ile Gln Arg Glu Asn Val Glu Ala Leu Leu Thr Glu Pro Ala Ile Leu
        355                 360                 365

Val Asn Pro Val Ser Cys Asp Thr Ala Gln Val Leu Pro Ile Val Gln
    370                 375                 380

Asn Ile Leu Ile Gln Asn Asp Ile Gln Arg Lys Arg Leu Ile Gly Leu
385                 390                 395                 400

Met Gln Leu Cys Asp Pro Thr Ala Gly Lys Phe Ala Val Leu Ser Leu
                405                 410                 415

Glu Phe Ala Ser Ser Leu Cys Tyr Lys Phe His Asp Leu Ile Leu Ile
            420                 425                 430

Phe Val Gln Lys Ser Glu Phe Arg Leu Ala Ile Gln Lys Leu Gly Arg
        435                 440                 445

Tyr Gln Gln Gln Arg Gln Ile Tyr Cys Leu Arg Phe Thr Phe Cys Ser
    450                 455                 460

Arg Gly Asn Asp Lys Phe His Lys Leu
465                 470
```

<210> SEQ ID NO 17
<211> LENGTH: 2085
<212> TYPE: DNA
<213> ORGANISM: Arabidopsis thaliana

<400> SEQUENCE: 17

| | | | | | |
|---|---|---|---|---|---|
| atggagaaga | agaagtatcc | aattggacca | gagcattata | ctctctacga | gtttattgga | 60 |
| caaggtgtta | gtgctctagt | gcatcgtgct | ttgtgcattc | cgtttgatga | agtcgttgct | 120 |
| attaagattc | ttgattttga | acgcgataac | tgcgatctga | acaacatctc | tcgtgaagcg | 180 |
| cagacgatga | tgcttgttga | tcatcccaat | gtgttgaagt | cacattgttc | ctttgttagt | 240 |
| gatcacaatt | tgtgggtcat | catgccatac | atgtctggtg | gttcttgtct | tcacattcta | 300 |
| aaagctgcat | atcctgatgg | ttttgaagaa | gctattatag | ctactatatt | gcgtgaagct | 360 |
| ttgaagggat | tagactatct | ccatcagcat | ggccacattc | atcgcgatgt | caaagctggg | 420 |
| aatatattgc | ttggtgctcg | aggtgcagtc | aagttgggag | actttggtgt | atctgcctgt | 480 |
| ctctttgatt | caggtgatag | gcaacggaca | aggaacacat | tgttggaaca | ccttgctgg  | 540 |
| atggcacctg | aagtcatgga | gcagctacat | ggttatgact | caaggctga  | tatttggtcg | 600 |
| tttggtataa | ctgggctaga | gcttgctcat | ggtcacgctc | ctttctctaa | atatccacca | 660 |
| atgaaggttc | tgcttatgac | gttgcaaaat | gcaccaccag | ggctggatta | cgaaagagat | 720 |
| aagaagtttt | ccaggtcttt | caagcagatg | atcgccagtt | gtctagttaa | agacccttcc | 780 |
| aaacgcccgt | ctgcaaaaaa | gttgttaaag | cactcctttt | tcaagcaagc | aagatcaagc | 840 |
| gattacattg | cacgaaaact | tctggatggg | ttaccagatc | ttgttaatcg | tgttcaggca | 900 |
| ataaagagaa | aggaagaaga | tatgcttgca | aagagaaaa  | tggcagatgg | agaaaaggaa | 960 |
| gaattgtccc | agcctttaaa | cgcttgtcat | agtaccatgc | agaatgaata | agagaggt   | 1020 |
| atcagcgggt | ggaatttcaa | tcttgatgat | atgaaagccc | aggcttcatt | gatccaggac | 1080 |
| atggactgtg | gcttttcgga | cagtttatcg | ggaagtgcaa | cttcgttgca | ggctctagat | 1140 |
| tcacaggata | cacaatcgga | gattcaggag | gatactggtc | aaataactaa | taagtatctc | 1200 |
| caacctctga | ttcaccgaag | tctaagtatc | gcgagggata | aatctgatga | tgattcaagt | 1260 |
| cttgccagcc | ccagttatga | tagctacgta | tattcctccc | ccgtcatga  | ggatttatct | 1320 |
| ttaaacaata | cacatgttgg | tagtacgcat | gcaaacaatg | ggaaaccaac | ggatgccaca | 1380 |
| tcaatcccaa | ccaatcaacc | aacagagatt | atagcaggga | gctctgtttt | ggcagatgga | 1440 |
| aatggtgctc | ccaataaagg | agagagtgat | aaaactcaag | aacagcttca | aaacgggtca | 1500 |
| aactgcaatg | ggacacatcc | tacagtggga | ggagatgacg | taccaacgga | gatggctgtt | 1560 |
| aaaccaccca | agcagcatc  | aagcctagat | gaatctgatg | acaaatcaaa | gccgccagtt | 1620 |
| gtgcagcaaa | gagggcgttt | taaagtaact | tctgaaaatc | tcgacatcga | aaggtggtg  | 1680 |
| gcgccttcgc | caatactgca | aaagagtcac | agcatgcagg | tgctctgcca | acattcctct | 1740 |
| gcttctctac | ctcactctga | tgtcacattg | ccaaacctaa | ccagctcata | tgtttacccg | 1800 |
| ctggtgtatc | cagttctgca | aactaatatt | ttggaaaggg | ataacatttt | gcatatgatg | 1860 |
| aaagtactca | ccaacagaga | gttgacagat | ggacgtgcag | ttgaacaagg | aagtatacaa | 1920 |
| caacctactg | tgcccccaac | tgagaaatcc | atgcttgaag | cagcacacga | aagagagaaa | 1980 |
| gaactgctcc | atgacataac | cgacctgcaa | tggaggctca | tttgtgcaga | agaagagctt | 2040 |
| cagaaataca | aaaccgaaca | cgcccaagta | agtatgagta | actaa      |            | 2085 |

<210> SEQ ID NO 18
<211> LENGTH: 694
<212> TYPE: PRT
<213> ORGANISM: Arabidopsis thaliana

<400> SEQUENCE: 18

```
Met Glu Lys Lys Lys Tyr Pro Ile Gly Pro Glu His Tyr Thr Leu Tyr
1               5                   10                  15

Glu Phe Ile Gly Gln Gly Val Ser Ala Leu Val His Arg Ala Leu Cys
            20                  25                  30

Ile Pro Phe Asp Glu Val Val Ala Ile Lys Ile Leu Asp Phe Glu Arg
        35                  40                  45

Asp Asn Cys Asp Leu Asn Asn Ile Ser Arg Glu Ala Gln Thr Met Met
    50                  55                  60

Leu Val Asp His Pro Asn Val Leu Lys Ser His Cys Ser Phe Val Ser
65                  70                  75                  80

Asp His Asn Leu Trp Val Ile Met Pro Tyr Met Ser Gly Gly Ser Cys
                85                  90                  95

Leu His Ile Leu Lys Ala Ala Tyr Pro Asp Gly Phe Glu Glu Ala Ile
            100                 105                 110

Ile Ala Thr Ile Leu Arg Glu Ala Leu Lys Gly Leu Asp Tyr Leu His
        115                 120                 125

Gln His Gly His Ile His Arg Asp Val Lys Ala Gly Asn Ile Leu Leu
    130                 135                 140

Gly Ala Arg Gly Ala Val Lys Leu Gly Asp Phe Gly Val Ser Ala Cys
145                 150                 155                 160

Leu Phe Asp Ser Gly Asp Arg Gln Arg Thr Arg Asn Thr Phe Val Gly
                165                 170                 175

Thr Pro Cys Trp Met Ala Pro Glu Val Met Glu Gln Leu His Gly Tyr
            180                 185                 190

Asp Phe Lys Ala Asp Ile Trp Ser Phe Gly Ile Thr Gly Leu Glu Leu
        195                 200                 205

Ala His Gly His Ala Pro Phe Ser Lys Tyr Pro Pro Met Lys Val Leu
    210                 215                 220

Leu Met Thr Leu Gln Asn Ala Pro Pro Gly Leu Asp Tyr Glu Arg Asp
225                 230                 235                 240

Lys Lys Phe Ser Arg Ser Phe Lys Gln Met Ile Ala Ser Cys Leu Val
                245                 250                 255

Lys Asp Pro Ser Lys Arg Pro Ser Ala Lys Lys Leu Leu Lys His Ser
            260                 265                 270

Phe Phe Lys Gln Ala Arg Ser Ser Asp Tyr Ile Ala Arg Lys Leu Leu
        275                 280                 285

Asp Gly Leu Pro Asp Leu Val Asn Arg Val Gln Ala Ile Lys Arg Lys
    290                 295                 300

Glu Glu Asp Met Leu Ala Gln Glu Lys Met Ala Asp Gly Glu Lys Glu
305                 310                 315                 320

Glu Leu Ser Gln Pro Leu Asn Ala Cys His Ser Thr Met Gln Asn Glu
                325                 330                 335

Tyr Lys Arg Gly Ile Ser Gly Trp Asn Phe Asn Leu Asp Asp Met Lys
            340                 345                 350

Ala Gln Ala Ser Leu Ile Gln Asp Met Asp Cys Gly Phe Ser Asp Ser
        355                 360                 365

Leu Ser Gly Ser Ala Thr Ser Leu Gln Ala Leu Asp Ser Gln Asp Thr
    370                 375                 380

Gln Ser Glu Ile Gln Glu Asp Thr Gly Gln Ile Thr Asn Lys Tyr Leu
```

```
                385                 390                 395                 400
Gln Pro Leu Ile His Arg Ser Leu Ser Ile Ala Arg Asp Lys Ser Asp
                    405                 410                 415

Asp Asp Ser Ser Leu Ala Ser Pro Ser Tyr Asp Ser Tyr Val Tyr Ser
                420                 425                 430

Ser Pro Arg His Glu Asp Leu Ser Leu Asn Asn Thr His Val Gly Ser
            435                 440                 445

Thr His Ala Asn Asn Gly Lys Pro Thr Asp Ala Thr Ser Ile Pro Thr
        450                 455                 460

Asn Gln Pro Thr Glu Ile Ile Ala Gly Ser Ser Val Leu Ala Asp Gly
465                 470                 475                 480

Asn Gly Ala Pro Asn Lys Gly Glu Ser Asp Lys Thr Gln Glu Gln Leu
                    485                 490                 495

Gln Asn Gly Ser Asn Cys Asn Gly Thr His Pro Thr Val Gly Gly Asp
                500                 505                 510

Asp Val Pro Thr Glu Met Ala Val Lys Pro Pro Lys Ala Ala Ser Ser
            515                 520                 525

Leu Asp Glu Ser Asp Asp Lys Ser Lys Pro Pro Val Val Gln Gln Arg
        530                 535                 540

Gly Arg Phe Lys Val Thr Ser Glu Asn Leu Asp Ile Glu Lys Val Val
545                 550                 555                 560

Ala Pro Ser Pro Ile Leu Gln Lys Ser His Ser Met Gln Val Leu Cys
                    565                 570                 575

Gln His Ser Ser Ala Ser Leu Pro His Ser Asp Val Thr Leu Pro Asn
                580                 585                 590

Leu Thr Ser Ser Tyr Val Tyr Pro Leu Val Tyr Pro Val Leu Gln Thr
            595                 600                 605

Asn Ile Leu Glu Arg Asp Asn Ile Leu His Met Met Lys Val Leu Thr
        610                 615                 620

Asn Arg Glu Leu Thr Asp Gly Arg Ala Val Glu Gln Gly Ser Ile Gln
625                 630                 635                 640

Gln Pro Thr Val Pro Pro Thr Glu Lys Ser Met Leu Glu Ala Ala His
                    645                 650                 655

Glu Arg Glu Lys Glu Leu Leu His Asp Ile Thr Asp Leu Gln Trp Arg
                660                 665                 670

Leu Ile Cys Ala Glu Glu Glu Leu Gln Lys Tyr Lys Thr Glu His Ala
            675                 680                 685

Gln Val Ser Met Ser Asn
        690

<210> SEQ ID NO 19
<211> LENGTH: 2591
<212> TYPE: DNA
<213> ORGANISM: Arabidopsis thaliana

<400> SEQUENCE: 19
gtcacacaag ccgaatccaa aaatgtaaca agaaaaacaa atcttcacaa ggcaaaaaat        60
ccaaaattga gtttttttt tcttcatttt ttacaatggt gtctcggttt cgtcttgctc       120
tagaggctgt tttgggttcg agacgacgta agaagatggc gagtactagt agtggtggtg       180
gtggtggtgg tgataagaag aagaagaaag gtttctctgt aaaccctaaa gattataaac       240
ttatggaaga agttggatat ggtgctagtg ctgttgttca tcgtgctatt tatcttccta       300
ctaatgaagt tgttgctatc aagtctttgg atctcgatcg ctgcaatagt aatctggatg       360
atataaggag ggaggctcag actatgactt tgatagacca tccgaatgtt ataaagtcgt       420
```

```
tttgttcgtt tgctgttgat catcatctat gggtcgttat gccatttatg gctcagggtt     480
cgtgtttgca tctaatgaaa gcagcgtatc cagatggatt tgaagaggcg gctatatgtt     540
ctatgctgaa agaaacactt aaagctcttg attatcttca tagacaaggg catatccatc     600
gagatgttaa ggctggaaac atacttcttg atgacactgg cgagattaag ttaggtgatt     660
ttggtgtctc tgcatgtttg tttgacaatg gcgataggca acgtgcaaga aatacatttg     720
ttggtactcc atgctggatg gcaccggaag tcttgcagcc agggagtgga tacaattcaa     780
aggctgatat atggtctttt ggaataacgg cgctggagtt ggctcacggt catgcacctt     840
tctcaaaata tccccctatg aaggtactct taatgactat ccaaaatgca ccacctggcc     900
ttgattatga ccgtgataag aagttttcaa agtcctttaa agaattggta gcattgtgtc     960
tggtgaaaga tcaaacaaaa aggccaactg ctgaaaaatt gttgaaacac tcatttttca    1020
agaatgtgaa gcctccagag atctgtgtaa aaaaattatt tgtcgattta ccacctcttt    1080
ggactcgcgt aaaagctctt caggccaagg atgctgcaca gcttgctttg aaaggaatgg    1140
cctctgctga ccaggatgct atatcacaga gtgaatacca agaggagta agtgcttgga    1200 acttcaatat cgaagatttg aaagaacaag catctttgct agatgatgat gacattctaa    1260
cagagagtag ggaagaagaa gaatctttg gcgaacagtt gcataataag gctaggcaag    1320
tatctggtag tcaattgcta tctgaaaaca tgaatgaaa ggaaaaagct tcagatactg    1380
aggtggtaga acctatctgt gaagagaaat ccactctcaa ttcaaccact tcttctgtgg    1440
aacaaccggc atcaagttca gaacaagacg ttccacaggc caagggtaag ccagtgagac    1500
tccagactca tagtggacca ctttcatccg gtgtcgtgtt aatcaattca gactcagaga    1560
aggttcatgg ttatgaaagg tctgagagtg aacggcaact gaaatcatca gtccggaggg    1620
cacccagctt tagtggtcct ttgaatcttc caaatcgtgc ttcagcaaac agtctttcag    1680
ctcctatcaa atcttctgga ggatttcgtg attctataga tgacaagtcg aaggctaatg    1740
tggttcaaat caaaggaaga ttttcagtaa catcagaaaa cttggatctt gcaagggcat    1800
cccctttgag aaaatctgcc agtgttggga attggatact tgattctaaa atgccaacgg    1860
gccaggccat caaggagtca agtagtcatc tctcattcat tatacctcag cttcaaaatc    1920
tgttccagca aaattcaatg cagcaggatc ttattatgaa tctagtgaat accttacaac    1980
aagctgctga acaacagat ggttctcaaa atggaaagtt gccgcctttg cctcgaggat    2040
ctgacagcaa tggaaccgtt gtagaactta cagcagctga gcgagagagg ttactactta    2100
ccaagataac cgagcttcga gctaggatga agagttgac ggaagaactt gaagtagaaa    2160
aatcaaaaca gacccaactg cagcagaaat tgaaatcagt caccggtcgc gagcaattgt    2220
aatcagagac cgggaacact gaccttacta cagagaagct ttttaggagg agagaaaagt    2280
atgttttgta cactaagaaa accagagagc tctctgatca tgaaagcaaa aaggacaggt    2340
ttggttctgt tctgtataag tgcagaagca gagtcaccat cggccatttg tttctgacag    2400
aagaagccgg aaacaaaaac agatagagag agataaatag agaagaaagc tctttggcca    2460
tggaaaattg tatttgttta tttaatctaa acactacaaa actttacatt ttttattatt    2520
gttagcaaca aatatagact cttcctttt tgtgtggatt gtaaatgaaa cattatttga    2580
tgtatttgtt t                                                         2591
```

<210> SEQ ID NO 20
<211> LENGTH: 708
<212> TYPE: PRT
<213> ORGANISM: Arabidopsis thaliana

<400> SEQUENCE: 20

```
Met Val Ser Arg Phe Arg Leu Ala Leu Glu Ala Val Leu Gly Ser Arg
1               5                   10                  15
Arg Arg Lys Lys Met Ala Ser Thr Ser Ser Gly Gly Gly Gly Gly Gly
            20                  25                  30
Asp Lys Lys Lys Lys Gly Phe Ser Val Asn Pro Lys Asp Tyr Lys
        35                  40                  45
Leu Met Glu Glu Val Gly Tyr Gly Ala Ser Ala Val Val His Arg Ala
    50                  55                  60
Ile Tyr Leu Pro Thr Asn Glu Val Val Ala Ile Lys Ser Leu Asp Leu
65                  70                  75                  80
Asp Arg Cys Asn Ser Asn Leu Asp Asp Ile Arg Arg Glu Ala Gln Thr
                85                  90                  95
Met Thr Leu Ile Asp His Pro Asn Val Ile Lys Ser Phe Cys Ser Phe
            100                 105                 110
Ala Val Asp His His Leu Trp Val Val Met Pro Phe Met Ala Gln Gly
        115                 120                 125
Ser Cys Leu His Leu Met Lys Ala Ala Tyr Pro Asp Gly Phe Glu Glu
    130                 135                 140
Ala Ala Ile Cys Ser Met Leu Lys Glu Thr Leu Lys Ala Leu Asp Tyr
145                 150                 155                 160
Leu His Arg Gln Gly His Ile His Arg Asp Val Lys Ala Gly Asn Ile
                165                 170                 175
Leu Leu Asp Asp Thr Gly Glu Ile Lys Leu Gly Asp Phe Gly Val Ser
            180                 185                 190
Ala Cys Leu Phe Asp Asn Gly Asp Arg Gln Arg Ala Arg Asn Thr Phe
        195                 200                 205
Val Gly Thr Pro Cys Trp Met Ala Pro Glu Val Leu Gln Pro Gly Ser
    210                 215                 220
Gly Tyr Asn Ser Lys Ala Asp Ile Trp Ser Phe Gly Ile Thr Ala Leu
225                 230                 235                 240
Glu Leu Ala His Gly His Ala Pro Phe Ser Lys Tyr Pro Pro Met Lys
                245                 250                 255
Val Leu Leu Met Thr Ile Gln Asn Ala Pro Pro Gly Leu Asp Tyr Asp
            260                 265                 270
Arg Asp Lys Lys Phe Ser Lys Ser Phe Lys Glu Leu Val Ala Leu Cys
        275                 280                 285
Leu Val Lys Asp Gln Thr Lys Arg Pro Thr Ala Glu Lys Leu Leu Lys
    290                 295                 300
His Ser Phe Phe Lys Asn Val Lys Pro Pro Glu Ile Cys Val Lys Lys
305                 310                 315                 320
Leu Phe Val Asp Leu Pro Pro Leu Trp Thr Arg Val Lys Ala Leu Gln
                325                 330                 335
Ala Lys Asp Ala Ala Gln Leu Ala Leu Lys Gly Met Ala Ser Ala Asp
            340                 345                 350
Gln Asp Ala Ile Ser Gln Ser Glu Tyr Gln Arg Gly Val Ser Ala Trp
        355                 360                 365
Asn Phe Asn Ile Glu Asp Leu Lys Glu Gln Ala Ser Leu Leu Asp Asp
    370                 375                 380
Asp Asp Ile Leu Thr Glu Ser Arg Glu Glu Glu Ser Phe Gly Glu
385                 390                 395                 400
Gln Leu His Asn Lys Ala Arg Gln Val Ser Gly Ser Gln Leu Leu Ser
                405                 410                 415
```

```
Glu Asn Met Asn Gly Lys Glu Lys Ala Ser Asp Thr Glu Val Val Glu
            420                 425                 430
Pro Ile Cys Glu Glu Lys Ser Thr Leu Asn Ser Thr Thr Ser Ser Val
        435                 440                 445
Glu Gln Pro Ala Ser Ser Glu Gln Asp Val Pro Gln Ala Lys Gly
    450                 455                 460
Lys Pro Val Arg Leu Gln Thr His Ser Gly Pro Leu Ser Ser Gly Val
465                 470                 475                 480
Val Leu Ile Asn Ser Asp Ser Glu Lys Val His Gly Tyr Glu Arg Ser
                485                 490                 495
Glu Ser Glu Arg Gln Leu Lys Ser Ser Val Arg Arg Ala Pro Ser Phe
            500                 505                 510
Ser Gly Pro Leu Asn Leu Pro Asn Arg Ala Ser Ala Asn Ser Leu Ser
        515                 520                 525
Ala Pro Ile Lys Ser Ser Gly Gly Phe Arg Asp Ser Ile Asp Asp Lys
    530                 535                 540
Ser Lys Ala Asn Val Val Gln Ile Lys Gly Arg Phe Ser Val Thr Ser
545                 550                 555                 560
Glu Asn Leu Asp Leu Ala Arg Ala Ser Pro Leu Arg Lys Ser Ala Ser
                565                 570                 575
Val Gly Asn Trp Ile Leu Asp Ser Lys Met Pro Thr Gly Gln Ala Ile
            580                 585                 590
Lys Glu Ser Ser Ser His Leu Ser Phe Ile Ile Pro Gln Leu Gln Asn
        595                 600                 605
Leu Phe Gln Gln Asn Ser Met Gln Gln Asp Leu Ile Met Asn Leu Val
    610                 615                 620
Asn Thr Leu Gln Gln Ala Ala Glu Thr Thr Asp Gly Ser Gln Asn Gly
625                 630                 635                 640
Lys Leu Pro Pro Leu Pro Arg Gly Ser Asp Ser Asn Gly Thr Val Val
                645                 650                 655
Glu Leu Thr Ala Ala Glu Arg Glu Arg Leu Leu Thr Lys Ile Thr
            660                 665                 670
Glu Leu Arg Ala Arg Met Lys Glu Leu Thr Glu Glu Leu Glu Val Glu
        675                 680                 685
Lys Ser Lys Gln Thr Gln Leu Gln Gln Lys Leu Lys Ser Val Thr Gly
    690                 695                 700
Arg Glu Gln Leu
705

<210> SEQ ID NO 21
<211> LENGTH: 2782
<212> TYPE: DNA
<213> ORGANISM: Arabidopsis thaliana

<400> SEQUENCE: 21
aaactactag tctctatctc tctcagctcc agattttgtt tcttcttctt ctgtgttaaa      60
ttcatttgat tgttgtatc tgaaggcgaa attactggtt tctgattttt ggtggtattc     120
agggcggttt taaagcgacg gaagaagatg gtggaggag gaggaggtag tagtggtcgt     180
ggtggtggta gtggtagtgg tagtagtaag cagcagagag gtttctctat gaatcctaaa     240
gactataagc taatggaaga aataggccat ggagctagcg ctgttgtcta tcgagcgatc     300
tatctcccta ctaatgaagt cgtcgccatc aagtgtttgg atctcgatcg ctgcaatagc     360
aatctggatg atattaggag ggaatctcag actatggagt tgatagacca tcccaacgtt     420
```

```
ataaagtcgt tttgttcatt ctctgtcgac catagtcttt gggttgttat gccattcatg   480
gctcaaggtt cgtgtttgca tcttatgaag actgcgtatt cagacggatt tgaagagtct   540
gctatatgtt gtgtattaaa agaaactctt aaagctcttg attatcttca tagacaaggc   600
catatccatc gggatgttaa ggctggaaac atacttcttg atgacaatgg tgagattaag   660
cttggcgatt tggtgtctc tgcttgcttg tttgataacg gtgataggca acgtgctaga   720
aacacatttg ttggtactcc ttgctggatg gcaccggaag ttttgcagcc gggaaatgga   780
tacaattcca aggctgatat ctggtcattt ggtataacag cacttgaatt ggcccatggt   840
catgcacctt tctcaaaata tcctcccatg aaggtgctcc taatgactat tcaaaacgca   900
cctcctggcc ttgattatga ccgtgataag aaatttctta agtcctttaa agaaatggtt   960
gcaatgtgtt tggtgaaaga tcaaacaaaa aggccaactg ctgaaaaact gctgaagcac  1020
tcctgtttca aacacacgaa gcctccagag caaactgtga aaattttatt ttccgattta  1080
ccacctcttt ggacacgtgt aaaatctctt caggataagg atgctcaaca gcttgcatta  1140
aagagaatgg ccactgctga cgaggaagct atatcacaga gcgaatacca agaggagtg   1200 agcgcttgga actttgacgt cagagacttg aaaacacaag catctttgtt aattgatgat  1260
gatgatctag aagagagtaa ggaagatgaa gaaatattat gtgcacagtt taataaggtg  1320
aatgacagag agcaagtatt tgatagtctg caactatatg aaaacatgaa cggaaaagaa  1380
aaggtttcca atactgaggt ggaagaacca acctgcaaag agaaattcac tttcgttaca  1440
actacttctt ctttagaacg aatgtcacca aattcagagc atgacattcc cgaggccaag  1500
gttaagccat taagacgcca aagtcagagt ggaccactta caagcaggac tgtattaagc  1560
cactcggctt cagagaaaag tcatatcttt gaaagatccg agagtgaacc gcagacggca  1620
ccaacagtcc gaagagcacc cagctttagt ggtccttga  atctttcaac ccgtgcttct  1680
tcaaacagtt tgtctgctcc catcaaatac tcaggaggat tccgtgattc tctggatgat  1740
aagtcaaagg ctaatctggt tcagaaagga cgattttcag taacatcagg aaatgtagat  1800
cttgcgaagg atgttccatt aagtatagtc cctcgtcgat ctccacaggc gaccccctg   1860 agaaaatctg caagtgtggg taactggata cttgagccca aatgccaac agctcagcct   1920 cagacgatca aggagcatag tagccatcct acgtcttcct cacccatcat gcctcaactt  1980
caacatctat tccagcaaaa ctcaatacaa caggatctta ttatgaattt actaaatagc  2040
ttacaacccg tggaggcaac agaaggttct caatctggga agttaccacc tttgcctcgc  2100
tcagacagta atgaaacgt tgaacctgtg cttcagaga gggagaggtt acttcttagc   2160
agtatctccg acctccgtgc taggctggac gacttaacgg aggaactcga tatagagaaa  2220
tcaaaataca gccaactgca acagaaattg aaagcattca cgggtcgcga acactaagtg  2280
taaccagagg gaaagcgaca ctggaaacac tgaactgcac agaacctgta ggagaaagag  2340
tgaagtctct tttggttata acagtaataa ccagacaaga gcttagagac agtgaggcat  2400
agagcatatc aatttctttta gttgggttca gtgtaggttc cagacgatga caatgacgac  2460
taaaacaaga tacgaccgat gtctgcttct gatgtaaact actagttgaa gacaacagaa  2520
acgaatacag aaataaaaga aaggagaag aaagttcctt tgggggggtct caaccccaca  2580 tatatttgct tatatattta ttatcacacg ttttgatcat ttttttgttt ttttttgttg   2640
gtgtatcata atttactagt gagataaagg agaaagctct tcttttgggt tctttgtgta  2700
ttgtaatttg taaatgcaaa ttgattgatg tacttttgtg ttttcatcac attcttaaac  2760
attatcttct ggttttacct ta                                          2782
```

<210> SEQ ID NO 22
<211> LENGTH: 709
<212> TYPE: PRT
<213> ORGANISM: Arabidopsis thaliana

<400> SEQUENCE: 22

Met Val Gly Gly Gly Gly Ser Gly Arg Gly Gly Ser Gly
1               5                   10                  15

Ser Gly Ser Ser Lys Gln Gln Arg Gly Phe Ser Met Asn Pro Lys Asp
            20                  25                  30

Tyr Lys Leu Met Glu Glu Ile Gly His Gly Ala Ser Ala Val Val Tyr
        35                  40                  45

Arg Ala Ile Tyr Leu Pro Thr Asn Glu Val Val Ala Ile Lys Cys Leu
    50                  55                  60

Asp Leu Asp Arg Cys Asn Ser Asn Leu Asp Asp Ile Arg Arg Glu Ser
65                  70                  75                  80

Gln Thr Met Ser Leu Ile Asp His Pro Asn Val Ile Lys Ser Phe Cys
                85                  90                  95

Ser Phe Ser Val Asp His Ser Leu Trp Val Val Met Pro Phe Met Ala
            100                 105                 110

Gln Gly Ser Cys Leu His Leu Met Lys Thr Ala Tyr Ser Asp Gly Phe
        115                 120                 125

Glu Glu Ser Ala Ile Cys Cys Val Leu Lys Glu Thr Leu Lys Ala Leu
    130                 135                 140

Asp Tyr Leu His Arg Gln Gly His Ile His Arg Asp Val Lys Ala Gly
145                 150                 155                 160

Asn Ile Leu Leu Asp Asp Asn Gly Glu Ile Lys Leu Gly Asp Phe Gly
                165                 170                 175

Val Ser Ala Cys Leu Phe Asp Asn Gly Asp Arg Gln Arg Ala Arg Asn
            180                 185                 190

Thr Phe Val Gly Thr Pro Cys Trp Met Ala Pro Glu Val Leu Gln Pro
        195                 200                 205

Gly Asn Gly Tyr Asn Ser Lys Ala Asp Ile Trp Ser Phe Gly Ile Thr
    210                 215                 220

Ala Leu Glu Leu Ala His Gly His Ala Pro Phe Ser Lys Tyr Pro Pro
225                 230                 235                 240

Met Lys Val Leu Leu Met Thr Ile Gln Asn Ala Pro Pro Gly Leu Asp
                245                 250                 255

Tyr Asp Arg Asp Lys Lys Phe Ser Lys Ser Phe Lys Glu Met Val Ala
            260                 265                 270

Met Cys Leu Val Lys Asp Gln Thr Lys Arg Pro Thr Ala Glu Lys Leu
        275                 280                 285

Leu Lys His Ser Cys Phe Lys His Thr Lys Pro Glu Gln Thr Val
    290                 295                 300

Lys Ile Leu Phe Ser Asp Leu Pro Pro Leu Trp Thr Arg Val Lys Ser
305                 310                 315                 320

Leu Gln Asp Lys Asp Ala Gln Leu Ala Leu Lys Arg Met Ala Thr
                325                 330                 335

Ala Asp Glu Glu Ala Ile Ser Gln Ser Glu Tyr Gln Arg Gly Val Ser
            340                 345                 350

Ala Trp Asn Phe Asp Val Arg Asp Leu Lys Thr Gln Ala Ser Leu Leu
        355                 360                 365

Ile Asp Asp Asp Leu Glu Glu Ser Lys Glu Asp Glu Glu Ile Leu
    370                 375                 380

```
Cys Ala Gln Phe Asn Lys Val Asn Asp Arg Glu Gln Val Phe Asp Ser
385                 390                 395                 400

Leu Gln Leu Tyr Glu Asn Met Asn Gly Lys Glu Lys Val Ser Asn Thr
            405                 410                 415

Glu Val Glu Glu Pro Thr Cys Lys Glu Lys Phe Thr Val Thr Thr
        420                 425                 430

Thr Ser Ser Leu Glu Arg Met Ser Pro Asn Ser Glu His Asp Ile Pro
    435                 440                 445

Glu Ala Lys Val Lys Pro Leu Arg Arg Gln Ser Gln Ser Gly Pro Leu
    450                 455                 460

Thr Ser Arg Thr Val Leu Ser His Ser Ala Ser Glu Lys Ser His Ile
465                 470                 475                 480

Phe Glu Arg Ser Glu Ser Glu Pro Gln Thr Ala Pro Thr Val Arg Arg
            485                 490                 495

Ala Pro Ser Phe Ser Gly Pro Leu Asn Leu Ser Thr Arg Ala Ser Ser
        500                 505                 510

Asn Ser Leu Ser Ala Pro Ile Lys Tyr Ser Gly Gly Phe Arg Asp Ser
    515                 520                 525

Leu Asp Asp Lys Ser Lys Ala Asn Leu Val Gln Lys Gly Arg Phe Ser
530                 535                 540

Val Thr Ser Gly Asn Val Asp Leu Ala Lys Asp Val Pro Leu Ser Ile
545                 550                 555                 560

Val Pro Arg Arg Ser Pro Gln Ala Thr Pro Leu Arg Lys Ser Ala Ser
            565                 570                 575

Val Gly Asn Trp Ile Leu Glu Pro Lys Met Pro Thr Ala Gln Pro Gln
        580                 585                 590

Thr Ile Lys Glu His Ser Ser His Pro Thr Ser Ser Pro Ile Met
    595                 600                 605

Pro Gln Leu Gln His Leu Phe Gln Gln Asn Ser Ile Gln Gln Asp Leu
    610                 615                 620

Ile Met Asn Leu Leu Asn Ser Leu Gln Pro Val Glu Ala Thr Glu Gly
625                 630                 635                 640

Ser Gln Ser Gly Lys Leu Pro Pro Leu Pro Arg Ser Asp Ser Asn Gly
            645                 650                 655

Asn Val Glu Pro Val Ala Ser Glu Arg Glu Arg Leu Leu Leu Ser Ser
        660                 665                 670

Ile Ser Asp Leu Arg Ala Arg Leu Asp Asp Leu Thr Glu Glu Leu Asp
    675                 680                 685

Ile Glu Lys Ser Lys Tyr Ser Gln Leu Gln Gln Lys Leu Lys Ala Phe
    690                 695                 700

Thr Gly Arg Glu His
705

<210> SEQ ID NO 23
<211> LENGTH: 2286
<212> TYPE: DNA
<213> ORGANISM: Oryza sativa

<400> SEQUENCE: 23
atggccaagg cgtgggagaa ggtggcgacg gcggcggggt tgggtgggtc gggggagagg     60
cgcaagtacc cgatccgcgt ggaggactac gagctgtacg aggagatcgg caggggggtc    120
agcgccatcg tgtaccgatc gctctgcaag cccctcgacg agatcgtcgc cgtcaaggtg    180
ctcgacttcg agcgcacaaa cagtgacctg tggttagttg taatgcaagt aggttatact    240
cggattgttg cgatttacgt accgccgctt gatctgtcta aaatgatagt aacacggata    300
```

```
tgcttgacgc agaacaacat catgcgtgaa gctcagacga tgattctcat agatcagcct    360
aacgtcatga aggcacattg ttcatttaca ataaccact cgttgtgggt ggtcatgcca    420
tacatggctg agggtcttg ccttcacata atgaagtcag tctatccaga tggttttgaa    480
gaagctgtca ttgcaactgt acttcgtgaa gtcctgaaag gtttggagta ccttcatcat    540
catgggcata tacatcgtga tgtgaaggca gggaatatac ttgttgattc acggggtgta    600
gtcaagcttg agatttttgg ggtttctgct tgccttttg attctggtga caggcaacgg    660
gctaggaata ctttcgtggg aactccttgc tggatggcac cagaggttat ggagcagcta    720
catggatacg atttcaaggc agacatatgg tccttcggaa ttactgcact tgaacttgcc    780
catggtcatg ctcctttctc gaagttccct cccatgaagg tcttacttat gacacttcag    840
aatgcccctc cgggccttga ctatgagaga gataagaaat tttcaaggca tttcaagcaa    900
atggttgcta tgtgtctggt aaaagaccct tcaaaaaggc ctacagcgaa aaaattgctg    960
aagcaaccct ttttcaagca agctcgctcc agtgatttca ttagtcgaaa gcttttggag   1020
ggattgcctg gccttggtgc cagatattta gctctgaagg aaaaggatga agttttactt   1080
tctcaaaaga aaatgcctga tggacagaag gaagaaatct cacaggatga atacaaaaga   1140
ggcatcagta gctggaactt tgatatggat gacctgaagt ctcaagcttc acttattaca   1200
gagtgtgatg acagtatatc gtgcaaagat tcagatgcat catgtttcta tgacttggac   1260
accattttac cagagcgagc aacaggacct catatgtcaa gagttttttc aattaagtat   1320
gatacggaca ccgaaaatga tgtgatgagc aatgataagt cagcagtttc atctcctgag   1380
caccccattt gtttagcaag gaatacatca atgctcagga ctacaaacgg ggtacatgca   1440
aatggccagg tcaggaaaca cagctccaca gaaagtagtg aactggactt gcaagagaaa   1500
gattcagatg ctattccaac cagttcattc agctcatttc atgaaaggaa gttttctttc   1560
agttcttgct catctgatgg atttctttca tccaaagaga gctcgaagca tcaaattaac   1620
attcataacc gtgacaagtg caacggagga cccttgcaag ttgcagatga accatcccct   1680
gaagctgttc caaaggtgcc taaatcatca gcagcaaatg ttgaggacca cgacgataga   1740
tcgaaacctc ctcttataca gcaaagaggc cgttttaaag ttacgcctgg gcatgttgag   1800
ttggataagg attttcaata tcgttcgatt caagaattga tgccatctgt tgggagcaat   1860
atacaggcaa tttcgcacct tccttcgtta agtataccat cctcaattga ggctgcatca   1920
accattattg gtgggtccct ttatatgcag ctgtacaatg ttctacagac aaatatgctt   1980
cagagggagc aaatacttca tgcgatgaaa cagttaagtg gttgcgatat ggcaatgacg   2040
tcacctgcct gcattgctcc tgcaagtcgc gcatcatctc catcatcagc attatcaatt   2100
gacagatcat tgttggaagc ggcacacgaa aaggagaagg agctggtcaa tgagatcact   2160
gagctgcaat ggcggttagt gtgttcgcag gacgagatac agaggctcaa agcaaaggca   2220
gcccaggtga ccatatctga tcttgtggag atgctgttag atatggaaca gcacgggaag   2280
gattga                                                               2286
```

<210> SEQ ID NO 24
<211> LENGTH: 534
<212> TYPE: PRT
<213> ORGANISM: Oryza sativa

<400> SEQUENCE: 24

```
Met Ala Ala Ala Ala Gly Ser Val Gly Gly Asp Asp His His His His
1               5                   10                  15
```

-continued

```
Gln Gln Ala Arg Tyr Pro Leu Asp Ala Gly Ser Tyr Arg Leu Leu Cys
        20                  25                  30

Lys Ile Gly Ser Gly Val Ser Ala Val Val Tyr Lys Ala Ala Cys Val
            35                  40                  45

Pro Leu Gly Ser Ala Val Val Ala Ile Lys Ala Ile Asp Leu Glu Arg
 50                  55                  60

Ser Arg Ala Asn Leu Asp Glu Val Trp Arg Glu Ala Lys Ala Met Ala
 65                  70                  75                  80

Leu Leu Ser His Arg Asn Val Leu Arg Ala His Cys Ser Phe Thr Val
                 85                  90                  95

Gly Ser His Leu Trp Val Val Met Pro Phe Met Ala Ala Gly Ser Leu
            100                 105                 110

His Ser Ile Leu Ser His Gly Phe Pro Asp Gly Leu Pro Glu Gln Cys
        115                 120                 125

Ile Ala Val Val Leu Arg Asp Thr Leu Arg Ala Leu Cys Tyr Leu His
    130                 135                 140

Glu Gln Gly Arg Ile His Arg Asp Ile Lys Ala Gly Asn Ile Leu Val
145                 150                 155                 160

Asp Ser Asp Gly Ser Val Lys Leu Ala Asp Phe Gly Val Ser Ala Ser
                165                 170                 175

Ile Tyr Glu Thr Ala Pro Ser Thr Ser Ser Ala Phe Ser Gly Pro Ile
            180                 185                 190

Asn His Ala Pro Pro Pro Ser Gly Ala Ala Leu Ser Ser Ser Cys Phe
        195                 200                 205

Asn Asp Met Ala Gly Thr Pro Tyr Trp Met Ala Pro Glu Val Ile His
    210                 215                 220

Ser His Val Gly Tyr Gly Ile Lys Ala Asp Ile Trp Ser Phe Gly Ile
225                 230                 235                 240

Thr Ala Leu Glu Leu Ala His Gly Arg Pro Pro Leu Ser His Leu Pro
                245                 250                 255

Pro Ser Lys Ser Met Leu Met Arg Ile Thr Ser Arg Val Arg Leu Glu
            260                 265                 270

Val Asp Ala Ser Ser Ser Ser Glu Gly Ser Ser Ala Ala Arg
        275                 280                 285

Lys Lys Lys Lys Phe Ser Lys Ala Phe Lys Asp Met Val Ser Ser Cys
    290                 295                 300

Leu Cys Gln Glu Pro Ala Lys Arg Pro Ser Ala Glu Lys Leu Leu Arg
305                 310                 315                 320

His Pro Phe Phe Lys Gly Cys Arg Ser Arg Asp Tyr Asp Tyr Leu Val
                325                 330                 335

Arg Asn Val Leu Asp Ala Val Pro Thr Val Glu Glu Arg Cys Arg Asp
            340                 345                 350

Ser Thr Gln Leu Cys Gly Cys Ala Arg Gly Ala Arg Cys Val Ser Pro
        355                 360                 365

Cys Arg His Ala Ser Ser Gly Ser Asn Val Val Ala Ala Lys Asn Arg
    370                 375                 380

Arg Ile Ser Gly Trp Asn Phe Asn Glu Glu Ser Phe Glu Leu Asp Pro
385                 390                 395                 400

Thr Asp Lys Pro Pro Glu Gln Gln Gln Gln Pro Cys Phe Pro Phe
                405                 410                 415

His His Asp Asn Asp Asp Met Val Glu His Glu Gln Glu Gln Arg
            420                 425                 430

Arg Arg Gln Asp Gly Asn Asp Gly Ser Ser Asp Val Ala Val Pro His
        435                 440                 445
```

```
Leu Val Thr Ile Leu Gly Ser Leu Glu Met Gln Arg Asp Met Val Met
    450                 455                 460
Gln Val Leu Glu Gly Asp Gly Gly Gly Gly Glu Thr Ala Gly Arg
465                 470                 475                 480
Glu Glu Met Leu Val Gly Tyr Val Arg Glu Leu Glu Lys Arg Val Gln
                485                 490                 495
Glu Leu Ser Thr Glu Val Glu Glu Met Ala Arg Asn Ala His Leu
            500                 505                 510
Gln Glu Leu Leu His Glu Arg Ala Cys Glu Asn His Thr Asp Ser Ser
        515                 520                 525
His Thr Ser Gly Ser Arg
    530

<210> SEQ ID NO 25
<211> LENGTH: 3038
<212> TYPE: DNA
<213> ORGANISM: Oryza sativa

<400> SEQUENCE: 25
gaccttctct tcctccctcg acacctctcc ccacgttacg ctgcctcctc ctcctcctcg      60
cctccctctc gtgggcgtcg tcccctccg ccaccgccgc cgcccgccgc agcagccgca     120 gaagggact ccacctcctc ccggatctgc tcgatcgccc ccgattctgt agcttctcct     180
ctgctcagat ccgcccctt gcttttcatc cagctcgtgg cacccgagat ccgctgccgc     240
cgccgccgtc tctgcggtcc tcctccccc tcgccggtgg ggaaccccgc cgccccgaag     300
cgcgttgcag cgtgtactac tgccggactg ccaaagtacg cttgctgcta gccatttcgg     360
tagcttttgt ggtttctact taactatcgt gtttggcaat acaacacctt ggaccaaagg     420
atgcttgaaa gatagactgg ataattaaga ctggatgcca agtacgcttt gctgctagcc     480
atttcggtag cttttgtggt ttctacttaa ctatcgtgtt tggcaataca acaccttgga     540
ccaaaggatg cttgaaagat agactggata ttaagaact atattggact gtacattcgc     600
ctatagactt agtcatgctg ctggttgttc tctgtcgctg ctacaaggtg ttcgtgctat     660
tgccttctgc ttctgtgtgc tatggtaatt gtaactctgt ggttattgcg catgatgctc     720
tttgaatttg agccatggag catgcaagga gatttccaac agatcccaaa gaatataaat     780
tatgtgagga agttggagat ggtgtagtgc tacggtgtac aaagctcttt gtatcccact     840
taatattgaa gttgccatta aagttcttga ccttgagaag tgcagtaatg acctggatgg     900
gataagacga gaagtacaaa ccatgagctt gattgatcat ccaaatcttc ttcgagcata     960
ttgctcgttt acaaatggtc atcagctttg ggttattatg ccttacatgg ccgctggatc    1020
tgctctgcac attatgaaaa cttcttttcc agatgggttt gaggagccag tcattgcaac    1080
tcttttgcgg gaggttctta agctcttgt ctacctacac tcccaagggc atattcacag    1140
agatgtaaag gctggaaata tcctaataga tacaaatgga gctgtcaagc taggagactt    1200
tggagtgtca gcctgcatgt tgatactgg aataggcaa agagcacgaa acactttttgt    1260 agggacccct tgctggatgg ctccagaagt tatgcaacaa ctgcatggtt atgattacaa    1320
agctgacatt tggtcctttg gtataacggc attggaacta gcatatggtc atgctccatt    1380
ttcaaagtac cctccaatga aggtattgct tatgaccttg caaatgcac accaggtct     1440 agactatgag agggacaagc gattttcaaa gtctttcaag gatttggttg caacttgctt    1500
agtcaaggat ccacgcaagc gtccatcttc agaaaagctc ttgaagcatt cttttttaa     1560 gcatgcacgt acagctgaat tcttgcacg aagtattctt gacggcctcc cccgctggg     1620
```

```
tgaacgcttt aggacattga agggaaaaga ggctgacttg cttcttagta ataagcttgg   1680
ttcagagagc aaggagcaac tatcacagaa agagtacata cgaggaatca gtggttggaa   1740
cttcaatctg gaggacttga aaaatgcagc cgcccttata gacaatacaa acggaacgtg   1800
ccatttagat ggtgttaaca gcaaattcaa ggatggttta caagaagcta atgaaccaga   1860
aaatatttac cagggacggg ctaaccttgt tgcttctgca aggcctgagg atgagataca   1920
agaggtcgaa gatctggatg gtgctctcgc ctcttctttc cccagccgcc cccttgaggc   1980
actaaaatct tgctttgatg tttgtgggga tgatgatccc cctactgcta ctgatttgag   2040
ggagcaacca aatatggaat ctacatcacc tatgcagcag ttccaacaaa ttgagaatca   2100
taaaagtgcc aactgtaatg gtgaaagttt ggaaagaagt gcctctgtac catcaaattt   2160
ggtcaatagt gggtcccaca agttcttaag tggttccctg atacctgaac atgttctttc   2220
tccttacagg aatgttggca atgacccagc aaggaatgag tgtcatcaga aaaatacatg   2280
caacaggaac cgcagtgggc ctttattccg ccaaatgaaa gatccacgcg cacatctgcc   2340
tgttgaacct gaggagcaat ccgaaggaaa agttatccag cgaaggggggc gttttcaggt   2400 tacatcagat agtattgctc aaaaggtagc ttcatccgca agcagcagta ggtgctcaaa   2460
tttaccaatc ggagtaacac gatcaactgt ccatccatcg acaattcttc caacactaca   2520
attcatgata cagcaaaata ctatgcaaaa ggaagtgata agtagactga tttcttcaat   2580
tgaggaaata tctgatgctg ctgatgcaag tacaactggt tcatctcagc catctggagt   2640
gcatttcaga gagaaggaac tgcagtcgta catcgccaac ttgcagcaaa gtgtcaccga   2700
acttgctgag gaagttcaga gattaaagct caaaaacact cagctcgagg agcagatcaa   2760
tgcattgccc aaaaaagatg aaaggttacg aagagaggat acccgacaac aatgatatgc   2820
acaatgcact tgtaaccccc gctgtaaaat cagttcccca attttgaatt tggttagcaa   2880 aattattgt atttgttcg aagtcaggcc tggtgtatct ttgtaatttg taattatttt   2940
agcaaggtga aattatagtt attttcattt gtacaggata tttcaatcta taccaaagtt   3000
aaaagcttgg tactagaaaa taccaaatca tctttcct                           3038
```

<210> SEQ ID NO 26
<211> LENGTH: 693
<212> TYPE: PRT
<213> ORGANISM: Oryza sativa

<400> SEQUENCE: 26

```
Met Glu His Ala Arg Arg Phe Pro Thr Asp Pro Lys Glu Tyr Lys Leu
1               5                   10                  15

Cys Glu Glu Val Gly Asp Gly Val Ser Ala Thr Val Tyr Lys Ala Leu
            20                  25                  30

Cys Ile Pro Leu Asn Ile Glu Val Ala Ile Lys Val Leu Asp Leu Glu
        35                  40                  45

Lys Cys Ser Asn Asp Leu Asp Gly Ile Arg Arg Glu Val Gln Thr Met
    50                  55                  60

Ser Leu Ile Asp His Pro Asn Leu Leu Arg Ala Tyr Cys Ser Phe Thr
65                  70                  75                  80

Asn Gly His Gln Leu Trp Val Ile Met Pro Tyr Met Ala Ala Gly Ser
                85                  90                  95

Ala Leu His Ile Met Lys Thr Ser Phe Pro Asp Gly Phe Glu Glu Pro
            100                 105                 110

Val Ile Ala Thr Leu Leu Arg Glu Val Leu Lys Ala Leu Val Tyr Leu
        115                 120                 125
```

-continued

His Ser Gln Gly His Ile His Arg Asp Val Lys Ala Gly Asn Ile Leu
    130                 135                 140

Ile Asp Thr Asn Gly Ala Val Lys Leu Gly Asp Phe Gly Val Ser Ala
145                 150                 155                 160

Cys Met Phe Asp Thr Gly Asn Arg Gln Arg Ala Arg Asn Thr Phe Val
                165                 170                 175

Gly Thr Pro Cys Trp Met Ala Pro Glu Val Met Gln Gln Leu His Gly
            180                 185                 190

Tyr Asp Tyr Lys Ala Asp Ile Trp Ser Phe Gly Ile Thr Ala Leu Glu
        195                 200                 205

Leu Ala His Gly His Ala Pro Phe Ser Lys Tyr Pro Pro Met Lys Val
    210                 215                 220

Leu Leu Met Thr Leu Gln Asn Ala Pro Pro Gly Leu Asp Tyr Glu Arg
225                 230                 235                 240

Asp Lys Arg Phe Ser Lys Ser Phe Lys Asp Leu Val Ala Thr Cys Leu
                245                 250                 255

Val Lys Asp Pro Arg Lys Arg Pro Ser Ser Glu Lys Leu Leu Lys His
            260                 265                 270

Ser Phe Phe Lys His Ala Arg Thr Ala Glu Phe Leu Ala Arg Ser Ile
        275                 280                 285

Leu Asp Gly Leu Pro Pro Leu Gly Glu Arg Phe Arg Thr Leu Lys Gly
    290                 295                 300

Lys Glu Ala Asp Leu Leu Leu Ser Asn Lys Leu Gly Ser Glu Ser Lys
305                 310                 315                 320

Glu Gln Leu Ser Gln Lys Glu Tyr Ile Arg Gly Ile Ser Gly Trp Asn
                325                 330                 335

Phe Asn Leu Glu Asp Leu Lys Asn Ala Ala Ala Leu Ile Asp Asn Thr
            340                 345                 350

Asn Gly Thr Cys His Leu Asp Gly Val Asn Ser Lys Phe Lys Asp Gly
        355                 360                 365

Leu Gln Glu Ala Asn Glu Pro Glu Asn Ile Tyr Gln Gly Arg Ala Asn
    370                 375                 380

Leu Val Ala Ser Ala Arg Pro Glu Asp Glu Ile Gln Glu Val Glu Asp
385                 390                 395                 400

Leu Asp Gly Ala Leu Ala Ser Ser Phe Pro Ser Arg Pro Leu Glu Ala
                405                 410                 415

Leu Lys Ser Cys Phe Asp Val Cys Gly Asp Asp Pro Thr Ala
            420                 425                 430

Thr Asp Leu Arg Glu Gln Pro Asn Met Glu Ser Thr Ser Pro Met Gln
        435                 440                 445

Gln Phe Gln Gln Ile Glu Asn His Lys Ser Ala Asn Cys Asn Gly Glu
    450                 455                 460

Ser Leu Glu Arg Ser Ala Ser Val Pro Ser Asn Leu Val Asn Ser Gly
465                 470                 475                 480

Ser His Lys Phe Leu Ser Gly Ser Leu Ile Pro Glu His Val Leu Ser
                485                 490                 495

Pro Tyr Arg Asn Val Gly Asn Asp Pro Ala Arg Asn Glu Cys His Gln
            500                 505                 510

Lys Asn Thr Cys Asn Arg Asn Arg Ser Gly Pro Leu Phe Arg Gln Met
        515                 520                 525

Lys Asp Pro Arg Ala His Leu Pro Val Glu Pro Glu Glu Gln Ser Glu
    530                 535                 540

Gly Lys Val Ile Gln Arg Arg Gly Arg Phe Gln Val Thr Ser Asp Ser

|  |  |  |  |  |  |  |  |  |  |  |  |
|--|--|--|--|--|--|--|--|--|--|--|--|
| | | 545 | | | 550 | | | 555 | | | 560 |

Ile Ala Gln Lys Val Ala Ser Ala Ser Ser Arg Cys Ser Asn
       565       570       575

Leu Pro Ile Gly Val Thr Arg Ser Thr Val His Pro Ser Thr Ile Leu
      580       585       590

Pro Thr Leu Gln Phe Met Ile Gln Gln Asn Thr Met Gln Lys Glu Val
     595       600       605

Ile Ser Arg Leu Ile Ser Ser Ile Glu Glu Ile Ser Asp Ala Ala Asp
   610       615       620

Ala Ser Thr Thr Gly Ser Ser Gln Pro Ser Gly Val His Phe Arg Glu
625       630       635       640

Lys Glu Leu Gln Ser Tyr Ile Ala Asn Leu Gln Ser Val Thr Glu
      645       650       655

Leu Ala Glu Glu Val Gln Arg Leu Lys Leu Lys Asn Thr Gln Leu Glu
     660       665       670

Glu Gln Ile Asn Ala Leu Pro Lys Lys Asp Glu Arg Leu Arg Arg Glu
   675       680       685

Asp Thr Arg Gln Gln
  690

<210> SEQ ID NO 27
<211> LENGTH: 2286
<212> TYPE: DNA
<213> ORGANISM: Oryza sativa

<400> SEQUENCE: 27

```
atggccaagg cgtgggagaa ggtggcgacg gcggcggggt tgggtgggtc gggggagagg      60
cgcaagtacc cgatccgcgt ggaggactac gagctgtacg aggagatcgg gcaggggtc     120
agcgccatcg tgtaccgatc gctctgcaag cccctcgacg agatcgtcgc cgtcaaggtg     180
ctcgacttcg agcgcacaaa cagtgacctg tggttagttg taatgcaagt aggttatact     240
cggattgttg cgatttacgt accgccgctt gatctgtcta aaatgatagt aacacggata     300
tgcttgacgc agaacaacat catgcgtgaa gctcagacga tgattctcat agatcagcct     360
aacgtcatga aggcacattg ttcatttaca ataaccact cgttgtgggt ggtcatgcca     420
tacatggctg agggtcttg ccttcacata atgaagtcag tctatccaga tggttttgaa     480
gaagctgtca ttgcaactgt acttcgtgaa gtcctgaaag gtttggagta ccttcatcat     540
catgggcata tacatcgtga tgtgaaggca gggaatatac ttgttgattc acggggtgta     600
gtcaagcttg gagattttgg ggtttctgct tgcctttttg attctggtga caggcaacgg     660
gctaggaata ctttcgtggg aactccttgc tggatggcac cagaggttat ggagcagcta     720
catggatacg atttcaaggc agacatatgg tccttcggaa ttactgcact tgaacttgcc     780
catggtcatg ctcctttctc gaagttccct cccatgaagg tcttacttat gacacttcag     840
aatgcccctc cgggccttga ctatgagaga gataagaaat tttcaaggca tttcaagcaa     900
atggttgcta tgtgtctggt aaaagaccct tcaaaaaggc ctacagcgaa aaaattgctg     960
aagcaaccct ttttcaagca agctcgctcc agtgatttca ttagtcgaaa gcttttggag    1020
ggattgcctg ccttggtgc cagatattta gctctgaagg aaaaggatga agttttactt    1080
tctcaaaaga aaatgcctga tggacagaag gaagaaatct cacaggatga atacaaaaga    1140
ggcatcagta gctggaactt tgatatggat gacctgaagt ctcaagcttc acttattaca    1200
gagtgtgatg acagtatatc gtgcaaagat tcagatgcat catgtttcta tgacttggac    1260
accattttac cagagcgagc aacaggacct catatgtcaa gagttttttc aattaagtat    1320
```

```
gatacggaca ccgaaaatga tgtgatgagc aatgataagt cagcagtttc atctcctgag   1380

caccccattt gtttagcaag gaatacatca atgctcagga ctacaaacgg ggtacatgca   1440
aatggccagg tcaggaaaca cagctccaca gaaagtagtg aactggactt gcaagagaaa   1500
gattcagatg ctattccaac cagttcattc agctcatttc atgaaaggaa gttttctttc   1560
agttcttgct catctgatgg atttctttca tccaaagaga gctcgaagca tcaaattaac   1620
attcataacc gtgacaagtg caacggagga cccttgcaag ttgcagatga accatcccct   1680
gaagctgttc caaaggtgcc taaatcatca gcagcaaatg ttgaggacca cgacgataga   1740
tcgaaacctc ctcttataca gcaaagaggc cgttttaaag ttacgcctgg gcatgttgag   1800
ttggataagg attttcaata tcgttcgatt caagaattga tgccatctgt tgggagcaat   1860
atacaggcaa tttcgcacct tccttcgtta agtataccat cctcaattga ggctgcatca   1920
accattattg gtgggtccct ttatatgcag ctgtacaatg ttctacagac aaatatgctt   1980
cagagggagc aaatacttca tgcgatgaaa cagttaagtg gttgcgatat ggcaatgacg   2040
tcacctgcct gcattgctcc tgcaagtcgc gcatcatctc catcatcagc attatcaatt   2100
gacagatcat tgttggaagc ggcacacgaa aaggagaagg agctggtcaa tgagatcact   2160
gagctgcaat ggcggttagt gtgttcgcag gacgagatac agaggctcaa agcaaaggca   2220
gcccaggtga ccatatctga tcttgtggag atgctgttag atatggaaca gcacgggaag   2280
gattga                                                              2286
```

<210> SEQ ID NO 28
<211> LENGTH: 761
<212> TYPE: PRT
<213> ORGANISM: Oryza sativa

<400> SEQUENCE: 28

```
Met Ala Lys Ala Trp Glu Lys Val Ala Thr Ala Ala Gly Leu Gly Gly
1               5                   10                  15

Ser Gly Glu Arg Arg Lys Tyr Pro Ile Arg Val Glu Asp Tyr Glu Leu
            20                  25                  30

Tyr Glu Glu Ile Gly Gln Gly Val Ser Ala Ile Val Tyr Arg Ser Leu
        35                  40                  45

Cys Lys Pro Leu Asp Glu Ile Val Ala Val Lys Val Leu Asp Phe Glu
    50                  55                  60

Arg Thr Asn Ser Asp Leu Trp Leu Val Val Met Gln Val Gly Tyr Thr
65                  70                  75                  80

Arg Ile Val Ala Ile Tyr Val Pro Pro Leu Asp Leu Ser Lys Met Ile
                85                  90                  95

Val Thr Arg Ile Cys Leu Thr Gln Asn Asn Ile Met Arg Glu Ala Gln
            100                 105                 110

Thr Met Ile Leu Ile Asp Gln Pro Asn Val Met Lys Ala His Cys Ser
        115                 120                 125

Phe Thr Asn Asn His Ser Leu Trp Val Val Met Pro Tyr Met Ala Gly
    130                 135                 140

Gly Ser Cys Leu His Ile Met Lys Ser Val Tyr Pro Asp Gly Phe Glu
145                 150                 155                 160

Glu Ala Val Ile Ala Thr Val Leu Arg Glu Val Leu Lys Gly Leu Glu
                165                 170                 175

Tyr Leu His His His Gly His Ile His Arg Asp Val Lys Ala Gly Asn
            180                 185                 190

Ile Leu Val Asp Ser Arg Gly Val Val Lys Leu Gly Asp Phe Gly Val
```

```
                195                 200                 205
Ser Ala Cys Leu Phe Asp Ser Gly Asp Arg Gln Arg Ala Arg Asn Thr
210                 215                 220

Phe Val Gly Thr Pro Cys Trp Met Ala Pro Glu Val Met Glu Gln Leu
225                 230                 235                 240

His Gly Tyr Asp Phe Lys Ala Asp Ile Trp Ser Phe Gly Ile Thr Ala
                245                 250                 255

Leu Glu Leu Ala His Gly His Ala Pro Phe Ser Lys Phe Pro Pro Met
                260                 265                 270

Lys Val Leu Leu Met Thr Leu Gln Asn Ala Pro Pro Gly Leu Asp Tyr
            275                 280                 285

Glu Arg Asp Lys Lys Phe Ser Arg His Phe Lys Gln Met Val Ala Met
            290                 295                 300

Cys Leu Val Lys Asp Pro Ser Lys Arg Pro Thr Ala Lys Lys Leu Leu
305                 310                 315                 320

Lys Gln Pro Phe Phe Lys Gln Ala Arg Ser Ser Asp Phe Ile Ser Arg
                325                 330                 335

Lys Leu Leu Glu Gly Leu Pro Gly Leu Gly Ala Arg Tyr Leu Ala Leu
                340                 345                 350

Lys Glu Lys Asp Glu Val Leu Leu Ser Gln Lys Lys Met Pro Asp Gly
            355                 360                 365

Gln Lys Glu Glu Ile Ser Gln Asp Glu Tyr Lys Arg Gly Ile Ser Ser
            370                 375                 380

Trp Asn Phe Asp Met Asp Asp Leu Lys Ser Gln Ala Ser Leu Ile Thr
385                 390                 395                 400

Glu Cys Asp Asp Ser Ile Ser Cys Lys Asp Ser Asp Ala Ser Cys Phe
                405                 410                 415

Tyr Asp Leu Asp Thr Ile Leu Pro Glu Arg Ala Thr Gly Pro His Met
                420                 425                 430

Ser Arg Val Phe Ser Ile Lys Tyr Asp Thr Thr Glu Asn Asp Val
            435                 440                 445

Met Ser Asn Asp Lys Ser Ala Val Ser Ser Pro Glu His Pro Ile Cys
450                 455                 460

Leu Ala Arg Asn Thr Ser Met Leu Arg Thr Thr Asn Gly Val His Ala
465                 470                 475                 480

Asn Gly Gln Val Arg Lys His Ser Ser Thr Glu Ser Ser Glu Leu Asp
                485                 490                 495

Leu Gln Glu Lys Asp Ser Asp Ala Ile Pro Thr Ser Ser Phe Ser Ser
            500                 505                 510

Phe His Glu Arg Lys Phe Ser Phe Ser Ser Cys Ser Ser Asp Gly Phe
            515                 520                 525

Leu Ser Ser Lys Glu Ser Ser Lys His Gln Ile Asn Ile His Asn Arg
530                 535                 540

Asp Lys Cys Asn Gly Gly Pro Leu Gln Val Ala Asp Glu Pro Ser Pro
545                 550                 555                 560

Glu Ala Val Pro Lys Val Pro Lys Ser Ser Ala Ala Asn Val Glu Asp
                565                 570                 575

His Asp Asp Arg Ser Lys Pro Leu Ile Gln Gln Arg Gly Arg Phe
                580                 585                 590

Lys Val Thr Pro Gly His Val Glu Leu Asp Lys Asp Phe Gln Tyr Arg
            595                 600                 605

Ser Ile Gln Glu Leu Met Pro Ser Val Gly Ser Asn Ile Gln Ala Ile
610                 615                 620
```

```
Ser His Leu Pro Ser Leu Ser Ile Pro Ser Ser Ile Glu Ala Ala Ser
625                 630                 635                 640

Thr Ile Ile Gly Gly Ser Leu Tyr Met Gln Leu Tyr Asn Val Leu Gln
            645                 650                 655

Thr Asn Met Leu Gln Arg Glu Gln Ile Leu His Ala Met Lys Gln Leu
            660                 665                 670

Ser Gly Cys Asp Met Ala Met Thr Ser Pro Ala Cys Ile Ala Pro Ala
            675                 680                 685

Ser Arg Ala Ser Ser Pro Ser Ser Ala Leu Ser Ile Asp Arg Ser Leu
            690                 695                 700

Leu Glu Ala Ala His Glu Lys Glu Lys Glu Leu Val Asn Glu Ile Thr
705                 710                 715                 720

Glu Leu Gln Trp Arg Leu Val Cys Ser Gln Asp Glu Ile Gln Arg Leu
            725                 730                 735

Lys Ala Lys Ala Ala Gln Val Thr Ile Ser Asp Leu Val Glu Met Leu
            740                 745                 750

Leu Asp Met Glu Gln His Gly Lys Asp
            755                 760
```

<210> SEQ ID NO 29
<211> LENGTH: 1623
<212> TYPE: DNA
<213> ORGANISM: Oryza sativa

<400> SEQUENCE: 29

| | | | | | |
|---|---|---|---|---|---|
| atgggagga | acgggagcgt | caagcgtacg | tcgtcgtcgg | gggcggcggc | ggcgttcacg | 60 |
| gcgaatcccc | gcgactacca | gctcatggag | gaggtcgggt | acggggcgca | cgccgtcgtg | 120 |
| taccgcgcgc | tgttcgtccc | caggaacgac | gtcgtggctg | tcaagtgcct | ggatctcgat | 180 |
| cagctcaaca | caacatcga | tgaaatccaa | cgggaggctc | aaatcatgag | cttgatagag | 240 |
| catcctaatg | tcatcagggc | ttactgctca | tttgttgttg | agcacagcct | ttgggtagta | 300 |
| atgccattta | tgactgaggg | ttcatgtctg | cacctaatga | agattgcata | tcctgatggt | 360 |
| ttcgaggaac | ctgttattgg | ctctattcta | aaggaaacac | ttaaggcttt | ggagtacctt | 420 |
| cacaggcaag | gacaaatcca | tcgtgatgtc | aaggccggca | atatccttgt | tgataatgct | 480 |
| ggtatagtga | agcttgggga | cttcggcgtg | tctgcttgta | tgtttgatag | aggtgatcga | 540 |
| caaagatcta | ggaacacatt | tgtgggaaca | ccgtgttgga | tggctccaga | agtgctccag | 600 |
| ccaggcactg | gatataactt | caaagctgac | atatggtcat | ttggaatcac | tgcacttgaa | 660 |
| cttgcccatg | ccatgcacc | gttttcaaag | tatcccccta | tgaaggttct | tctcatgacc | 720 |
| ctccagaatg | ctccacctgg | tctcgactat | gatcgagacc | gaagattctc | aaagtcattt | 780 |
| aaggagatgg | ttgcaatgtg | cttggtaaaa | gatcaaacaa | agagaccaac | agctgagaag | 840 |
| ttgctaaagc | attcattttt | caaaaatgca | aaacctccag | aattgacaat | gaagggtatc | 900 |
| ttaactgatt | tacctcctct | atgggaccgt | gtaaaggctc | tccagcttaa | agatgcagca | 960 |
| cagttggcct | tgaagaaaat | gccttcttct | gagcaggagg | cactctccat | gagtgaatac | 1020 |
| caacgaggtg | ttagtgcatg | gaacttcgat | gttgaagatc | tcaaggccca | agcatcacta | 1080 |
| attcgtgatg | atgaaccccc | tgaaataaaa | gaagacgatg | atactgcaag | aaccattgaa | 1140 |
| gttgaaaagg | attcattttc | taggaatcat | ttggggaagt | cgtcgagtac | aattgaaaat | 1200 |
| ttcttcagtg | gacggacctc | taccactgca | gcaaattcgg | atggaaaagg | cgattttca | 1260 |
| tttgaagctt | tgattttggg | tgaaaacaac | gttgatacta | aaattatgcc | caatgggtat | 1320 |
| gaaaacgcta | gatcagagaa | tagctcatca | ccctctacat | caaagcaaga | tccagagtca | 1380 |

-continued

```
aaatattgga gaagtacttc tggacagaaa caacaaactt ctggcactcc agctgtccat   1440
tctggtgggg ttaatagctc aacaactgaa aagggccatg gtgttgaaag ggatgcaact   1500
gttcaattgg catctgataa acttaggact gaaacgagaa gagcaacaaa tcttagtggt   1560
ccattgtcac tgccaactcg tgcttctgca aacagtctgt cagctcctat tcgatcttca   1620
gga                                                                 1623

<210> SEQ ID NO 30
<211> LENGTH: 541
<212> TYPE: PRT
<213> ORGANISM: Oryza sativa

<400> SEQUENCE: 30
```

Met Gly Arg Asn Gly Ser Val Lys Arg Thr Ser Ser Gly Ala Ala
1               5                   10                  15

Ala Ala Phe Thr Ala Asn Pro Arg Asp Tyr Gln Leu Met Glu Glu Val
            20                  25                  30

Gly Tyr Gly Ala His Ala Val Tyr Arg Ala Leu Phe Val Pro Arg
        35                  40                  45

Asn Asp Val Val Ala Val Lys Cys Leu Asp Leu Asp Gln Leu Asn Asn
50                  55                  60

Asn Ile Asp Glu Ile Gln Arg Glu Ala Gln Ile Met Ser Leu Ile Glu
65                  70                  75                  80

His Pro Asn Val Ile Arg Ala Tyr Cys Ser Phe Val Val Glu His Ser
                85                  90                  95

Leu Trp Val Val Met Pro Phe Met Thr Glu Gly Ser Cys Leu His Leu
            100                 105                 110

Met Lys Ile Ala Tyr Pro Asp Gly Phe Glu Glu Pro Val Ile Gly Ser
        115                 120                 125

Ile Leu Lys Glu Thr Leu Lys Ala Leu Glu Tyr Leu His Arg Gln Gly
    130                 135                 140

Gln Ile His Arg Asp Val Lys Ala Gly Asn Ile Leu Val Asp Asn Ala
145                 150                 155                 160

Gly Ile Val Lys Leu Gly Asp Phe Gly Val Ser Ala Cys Met Phe Asp
                165                 170                 175

Arg Gly Asp Arg Gln Arg Ser Arg Asn Thr Phe Val Gly Thr Pro Cys
            180                 185                 190

Trp Met Ala Pro Glu Val Leu Gln Pro Gly Thr Gly Tyr Asn Phe Lys
        195                 200                 205

Ala Asp Ile Trp Ser Phe Gly Ile Thr Ala Leu Glu Leu Ala His Gly
    210                 215                 220

His Ala Pro Phe Ser Lys Tyr Pro Pro Met Lys Val Leu Leu Met Thr
225                 230                 235                 240

Leu Gln Asn Ala Pro Pro Gly Leu Asp Tyr Asp Arg Asp Arg Arg Phe
                245                 250                 255

Ser Lys Ser Phe Lys Glu Met Val Ala Met Cys Leu Val Lys Asp Gln
            260                 265                 270

Thr Lys Arg Pro Thr Ala Glu Lys Leu Leu Lys His Ser Phe Phe Lys
        275                 280                 285

Asn Ala Lys Pro Pro Glu Leu Thr Met Lys Gly Ile Leu Thr Asp Leu
    290                 295                 300

Pro Pro Leu Trp Asp Arg Val Lys Ala Leu Gln Leu Lys Asp Ala Ala
305                 310                 315                 320

Gln Leu Ala Leu Lys Lys Met Pro Ser Ser Glu Gln Glu Ala Leu Ser

```
                           325                 330                 335
Met Ser Glu Tyr Gln Arg Gly Val Ser Ala Trp Asn Phe Asp Val Glu
            340                 345                 350

Asp Leu Lys Ala Gln Ala Ser Leu Ile Arg Asp Asp Glu Pro Pro Glu
            355                 360                 365

Ile Lys Glu Asp Asp Thr Ala Arg Thr Ile Glu Val Glu Lys Asp
            370                 375                 380

Ser Phe Ser Arg Asn His Leu Gly Lys Ser Ser Thr Ile Glu Asn
385                 390                 395                 400

Phe Phe Ser Gly Arg Thr Ser Thr Thr Ala Ala Asn Ser Asp Gly Lys
                405                 410                 415

Gly Asp Phe Ser Phe Glu Ala Phe Asp Phe Gly Glu Asn Asn Val Asp
                420                 425                 430

Thr Lys Ile Met Pro Asn Gly Tyr Glu Asn Ala Arg Ser Glu Asn Ser
                435                 440                 445

Ser Ser Pro Ser Thr Ser Lys Gln Asp Pro Ser Lys Tyr Trp Arg
            450                 455                 460

Ser Thr Ser Gly Gln Lys Gln Gln Thr Ser Gly Thr Pro Ala Val His
465                 470                 475                 480

Ser Gly Gly Val Asn Ser Ser Thr Thr Glu Lys Gly His Gly Val Glu
                485                 490                 495

Arg Asp Ala Thr Val Gln Leu Ala Ser Asp Lys Leu Arg Thr Glu Thr
            500                 505                 510

Arg Arg Ala Thr Asn Leu Ser Gly Pro Leu Ser Leu Pro Thr Arg Ala
            515                 520                 525

Ser Ala Asn Ser Leu Ser Ala Pro Ile Arg Ser Ser Gly
            530                 535                 540

<210> SEQ ID NO 31
<211> LENGTH: 1938
<212> TYPE: DNA
<213> ORGANISM: Oryza sativa

<400> SEQUENCE: 31
atggtgagga gcgggagtgt gcggcggacg gccgcgtcgt cgtcgcccgc cgcggcggcg        60
gtgccgacgg ccttcaccgc ctcgcccggc gactaccgcc ttctggagga ggtcggctac       120
ggcgcgaacg ccgtcgtgta ccgggcggtg ttcctgccat ccaaccggac cgtcgccgtc       180
aagtgcctgg atctcgatcg tgtcaacagt aacctcgatg atataagaaa agaggcacaa       240
acgatgagct tgatagatca ccctaatgtc atcagggctt actgctcatt tgttgtggat       300
cataacctct gggtgataat gccattcatg tcagagggtt catgtttaca cctgatgaag       360
gttgcatatc ctgatggttt tgaggagcct gttatcgcct ctatcctaaa ggaaacactt       420
aaggctctag agtacctcca tcggcaagga catatccata gggatgtcaa gcgtaatatt       480
atacaggcgg gtaatatcct tatggacagt cctggtatag tgaaacttgg ggactttggt       540
gtctctgctt gtatgtttga tagaggtgat agacaaagat ccaggaatac attcgtggga       600
acaccatgct ggatggctcc agaagttctc agcctggag caggatataa tttcaagaaa       660
tatgtttcaa accatttgtt taccaactta atttggttat ttaaaatttc cttaaggggt       720
aagaactcta actaccataa aaatactggg aataaggttc ttctcatgac ccttcaaaat       780
gcaccaccag gccttgacta tgaccgtgat aaaagattct caaagtcttt caaggaaatg       840
gttgcaatgt gcctggtcaa agatcaaaca aagaggccaa cggctgaaaa gttactaaag       900
cactcatttt tcaagaacgc aaaacctcca gagctgactg ttaagagtat tttaactgat       960
```

```
ttgcccctc tgtgggatcg tgtaaaagcg ctccagctaa aagatgcagc acaattagct    1020
ttgaagaaaa tgccttcttc tgaacaggag gcactttcta tgattcatga tgatgatcca    1080
cctgaaataa aggaagatgt tgacaatgat agaataaatg aagctgataa ggagccgttt    1140
tctggcaatc attttggaca accaaaaatt ttgagtggaa agcacttcag gttgaatcat    1200
gaacaaactt gtgtcactgc agtaagtcca ggggggaata tgcatgagac aagcaggaga    1260
ttggtttctg aacctggtga tgctgatagt gaaaggaaag ttgatggata tagaaaacaa    1320
ggggaagcgg cagttaagtt ggcatctgat aaacaaaaga gttgtacaaa agaaccaca    1380 aatctcagtg gtcctcttgc actccctact cgtgcttctg caaatagtct gtctgctcct    1440
attcggtctt ctggaggcta tgtgggctcc ttgggagata agtctaagcg tagtgtggtg    1500
gagataaaag gacgttttc agtgacatct gagaatgtgg atcttgcaaa ggttcaggaa    1560
gttccaacaa gcggcatttc acgcaaatta caggagggat cttcactgag aaaatcagcc    1620
agcgttggtc attggccggt ggatgctaag ccaatggatc tcatcacaaa cctcctaagt    1680
agcttgcaac agaatgagaa agctgacgca acacagtata gacttggtaa tatggatggt    1740
gatacagagg ttgaaacgtc tatttccgag ggagaacggt cattacttgt caaaatattt    1800
gaattgcaat ctagaatgat ttcattaacc gatgaactga tcacaacaaa actgcaacat    1860
gtccagctac aagaagagct aaaaatactg tactgtcacg aagaaataat cgacactagg    1920
gaggtggaca atgcttga                                                  1938

<210> SEQ ID NO 32
<211> LENGTH: 645
<212> TYPE: PRT
<213> ORGANISM: Oryza sativa

<400> SEQUENCE: 32

Met Val Arg Ser Gly Ser Val Arg Arg Thr Ala Ala Ser Ser Ser Pro
1               5                   10                  15

Ala Ala Ala Ala Val Pro Thr Ala Phe Thr Ala Ser Pro Gly Asp Tyr
                20                  25                  30

Arg Leu Leu Glu Glu Val Gly Tyr Gly Ala Asn Ala Val Val Tyr Arg
            35                  40                  45

Ala Val Phe Leu Pro Ser Asn Arg Thr Val Ala Lys Cys Leu Asp
        50                  55                  60

Leu Asp Arg Val Asn Ser Asn Leu Asp Asp Ile Arg Lys Glu Ala Gln
65                  70                  75                  80

Thr Met Ser Leu Ile Asp His Pro Asn Val Ile Arg Ala Tyr Cys Ser
                85                  90                  95

Phe Val Val Asp His Asn Leu Trp Val Ile Met Pro Phe Met Ser Glu
            100                 105                 110

Gly Ser Cys Leu His Leu Met Lys Val Ala Tyr Pro Asp Gly Phe Glu
        115                 120                 125

Glu Pro Val Ile Ala Ser Ile Leu Lys Glu Thr Leu Lys Ala Leu Glu
    130                 135                 140

Tyr Leu His Arg Gln Gly His Ile His Arg Asp Val Lys Arg Asn Ile
145                 150                 155                 160

Ile Gln Ala Gly Asn Ile Leu Met Asp Ser Pro Gly Ile Val Lys Leu
                165                 170                 175

Gly Asp Phe Gly Val Ser Ala Cys Met Phe Asp Arg Gly Asp Arg Gln
            180                 185                 190

Arg Ser Arg Asn Thr Phe Val Gly Thr Pro Cys Trp Met Ala Pro Glu
```

-continued

```
            195                 200                 205
Val Leu Gln Pro Gly Ala Gly Tyr Asn Phe Lys Lys Tyr Val Ser Asn
210                 215                 220

His Leu Phe Thr Asn Leu Ile Trp Leu Phe Lys Ile Ser Leu Arg Gly
225                 230                 235                 240

Lys Asn Ser Asn Tyr His Lys Asn Thr Gly Asn Lys Val Leu Leu Met
                245                 250                 255

Thr Leu Gln Asn Ala Pro Pro Gly Leu Asp Tyr Asp Arg Asp Lys Arg
            260                 265                 270

Phe Ser Lys Ser Phe Lys Glu Met Val Ala Met Cys Leu Val Lys Asp
        275                 280                 285

Gln Thr Lys Arg Pro Thr Ala Glu Lys Leu Leu Lys His Ser Phe Phe
290                 295                 300

Lys Asn Ala Lys Pro Pro Glu Leu Thr Val Lys Ser Ile Leu Thr Asp
305                 310                 315                 320

Leu Pro Pro Leu Trp Asp Arg Val Lys Ala Leu Gln Leu Lys Asp Ala
                325                 330                 335

Ala Gln Leu Ala Leu Lys Lys Met Pro Ser Ser Glu Gln Glu Ala Leu
            340                 345                 350

Ser Met Ile His Asp Asp Pro Glu Ile Lys Glu Asp Val Asp
        355                 360                 365

Asn Asp Arg Ile Asn Glu Ala Asp Lys Glu Pro Phe Ser Gly Asn His
        370                 375                 380

Phe Gly Gln Pro Lys Ile Leu Ser Gly Lys His Phe Arg Leu Asn His
385                 390                 395                 400

Glu Gln Thr Cys Val Thr Ala Val Ser Pro Gly Gly Asn Met His Glu
                405                 410                 415

Thr Ser Arg Gly Leu Val Ser Glu Pro Gly Asp Ala Asp Ser Glu Arg
            420                 425                 430

Lys Val Asp Gly Tyr Arg Lys Gln Gly Glu Ala Ala Val Lys Leu Ala
        435                 440                 445

Ser Asp Lys Gln Lys Ser Cys Thr Lys Arg Thr Thr Asn Leu Ser Gly
450                 455                 460

Pro Leu Ala Leu Pro Thr Arg Ala Ser Ala Asn Ser Leu Ser Ala Pro
465                 470                 475                 480

Ile Arg Ser Ser Gly Tyr Val Gly Ser Leu Gly Asp Lys Ser Lys
                485                 490                 495

Arg Ser Val Val Glu Ile Lys Gly Arg Phe Ser Val Thr Ser Glu Asn
                500                 505                 510

Val Asp Leu Ala Lys Val Gln Glu Val Pro Thr Ser Gly Ile Ser Arg
            515                 520                 525

Lys Leu Gln Glu Gly Ser Ser Leu Arg Lys Ser Ala Ser Val Gly His
        530                 535                 540

Trp Pro Val Asp Ala Lys Pro Met Asp Leu Ile Thr Asn Leu Leu Ser
545                 550                 555                 560

Ser Leu Gln Gln Asn Glu Lys Ala Asp Ala Thr Gln Tyr Arg Leu Gly
                565                 570                 575

Asn Met Asp Gly Asp Thr Glu Val Glu Thr Ser Ile Ser Glu Gly Glu
            580                 585                 590

Arg Ser Leu Leu Val Lys Ile Phe Glu Leu Gln Ser Arg Met Ile Ser
        595                 600                 605

Leu Thr Asp Glu Leu Ile Thr Thr Lys Leu Gln His Val Gln Leu Gln
610                 615                 620
```

```
Glu Glu Leu Lys Ile Leu Tyr Cys His Glu Glu Ile Ile Asp Thr Arg
625                 630                 635                 640

Glu Val Asp Asn Ala
            645

<210> SEQ ID NO 33
<211> LENGTH: 2040
<212> TYPE: DNA
<213> ORGANISM: Medicago sativa

<400> SEQUENCE: 33
atttattaaa attgatgtga cggtctctat agggccgttt catctaaatt tattaaaatt        60
tagatccaac tatcttataa tccgttgcac tgtgcaacag ttatagagaa tccaaattcc       120
gtaacaggag cttaaattct ctatgattgt tgcacatctc cggtagagta tctaaattta       180
agaaatacaa catatcagag atattatgta gaaacacata ttatcaagtt aattaactag       240
taggactatt agcagcagag gaaattaggt gaagcttgat attctccagc tgcatctcca       300
gctgcaagtt cttcttcttc tcattttcca attctgtcct caacttagag atctcttgca       360 ccatttctc atcactttca gccacatgaa tctcctctcc accaattaga ttcattagaa       420
acttaacttg tcccaactct tgttccaagc tctctttcaa cacattcaac gttgccaacg       480
tagcttcacg gttcttaaca acaccaccga cattttcatg atcaaccaca tcagaagtat       540
tggtctttgg ctccatcaca gttcctgatg ctgtaacaac agcatcctct tggatcactt       600
tttcttcttc gaaccgaact tgtttcacaa cttcatcatc tttgctttga tcctttggga       660
atacaggcac aagttccaat ccatcttcat tgaaattcca gccactgatt cttctctgtt       720
tcacattttt cactgactcg tcatcatcgt cgtctccatc atccttgcac tttgaatctg       780
gatccattat agctttgatc tctttatacc ttttctcaac actaggcaat ccattcaaca       840
cattcttcac caaaacatct gatcccttgc agttttttaaa gaatgaatgc ttaagtaact       900
tctcagcaga gggtcttttt gtaggatctt gattcaaaca taaagcaacc atatccttaa       960
aagccttaga gaatttgtta ctaccaccat gaccccttgta actatgttta tcaaaatcag      1020
aaaacttaaa cctctttgta atgtttagca tcaatgactt agaaggagga agatgagaaa      1080
gtggtggtct tccatgtgct aactccaaag ctgttatccc aaaagaccag atatcagctt      1140
tgaaactgta accattatga gagtgaataa cctcaggagc catccaataa ggtgttccag      1200
caaaatcagt aaatatatga gaagaagaag aattcgaaga cgaagatgaa taagaagaac      1260
atgctcctac agagttgttt gattcataaa tggaagcaga acaccaaaa tctgcaagtt       1320 tcactaatcc atttgagtca acaaggatgt taccagattt gatatctcta tgaagatgtc      1380
cttgtccatg aaggtaagaa agagcattga gagtgtcttt gagaataaca gctatggatt      1440
gttctgttaa gccgttttgg aaagagtgag agataatgga ttgtaatgaa cctccagcca      1500
tgaatggcat aaccacccaa agacggttgt caacggtgaa agaacagtga gctttgagga      1560
tgttggggtg ggaaagaagt gataatgtct ttgcttcacg tctaacatcg tcaaggtcgg      1620
ggcgcgaacg atccaagtct atggatttga tagctactgg tgtggagttt atagggatgc      1680
agattgcttt gtagacgacg gcgctgttac cggcgccaat ctcgtcgacg attttatagg      1740
aggaagagtc taatggatat tgcactcttt ctgctatgtt ggtagccatg aaataatgg       1800 aagttgagat ataagagtgt gtgtgtgtgt gtgtgttaga ggttgaaaat ggttgtttga      1860
aaatatataa gatgaatgaa ttgcatggat tggtgatgga tggatggatg gtgaaattaa      1920
ttgataaaga gagtggtagg ttgagtttga gcagttttct tgtgaaggtt gatgaaaaaa      1980
```
gaagaaaata tcattaggca gaggtgattt atttctcaat gatctatcag tggttgtgaa    2040

<210> SEQ ID NO 34
<211> LENGTH: 518
<212> TYPE: PRT
<213> ORGANISM: Medicago sativa

<400> SEQUENCE: 34

Met Ala Thr Asn Ile Ala Glu Arg Val Gln Tyr Pro Leu Asp Ser Ser
1               5                   10                  15

Ser Tyr Lys Ile Val Asp Glu Ile Gly Ala Gly Asn Ser Ala Val Val
            20                  25                  30

Tyr Lys Ala Ile Cys Ile Pro Ile Asn Ser Thr Pro Val Ala Ile Lys
        35                  40                  45

Ser Ile Asp Leu Asp Arg Ser Arg Pro Asp Leu Asp Asp Val Arg Arg
    50                  55                  60

Glu Ala Lys Thr Leu Ser Leu Leu Ser His Pro Asn Ile Leu Lys Ala
65                  70                  75                  80

His Cys Ser Phe Thr Val Asp Asn Arg Leu Trp Val Val Met Pro Phe
                85                  90                  95

Met Ala Gly Gly Ser Leu Gln Ser Ile Ile Ser His Ser Phe Gln Asn
            100                 105                 110

Gly Leu Thr Glu Gln Ser Ile Ala Val Ile Leu Lys Asp Thr Leu Asn
        115                 120                 125

Ala Leu Ser Tyr Leu His Gly Gln Gly His Leu His Arg Asp Ile Lys
    130                 135                 140

Ser Gly Asn Ile Leu Val Asp Ser Asn Gly Leu Val Lys Leu Ala Asp
145                 150                 155                 160

Phe Gly Val Ser Ala Ser Ile Tyr Glu Ser Asn Asn Ser Val Gly Ala
                165                 170                 175

Cys Ser Ser Tyr Ser Ser Ser Ser Asn Ser Ser Ser His Ile
            180                 185                 190

Phe Thr Asp Phe Ala Gly Thr Pro Tyr Trp Met Ala Pro Glu Val Ile
        195                 200                 205

His Ser His Asn Gly Tyr Ser Phe Lys Ala Asp Ile Trp Ser Phe Gly
    210                 215                 220

Ile Thr Ala Leu Glu Leu Ala His Gly Arg Pro Pro Leu Ser His Leu
225                 230                 235                 240

Pro Pro Ser Lys Ser Leu Met Leu Asn Ile Thr Lys Arg Phe Lys Phe
                245                 250                 255

Ser Asp Phe Asp Lys His Ser Tyr Lys Gly His Gly Gly Ser Asn Lys
            260                 265                 270

Phe Ser Lys Ala Phe Lys Asp Met Val Ala Leu Cys Leu Asn Gln Asp
        275                 280                 285

Pro Thr Lys Arg Pro Ser Ala Glu Lys Leu Leu Lys His Ser Phe Phe
    290                 295                 300

Lys Asn Cys Lys Gly Ser Asp Val Leu Val Asn Val Leu Asn Gly
305                 310                 315                 320

Leu Pro Ser Val Glu Lys Arg Tyr Lys Glu Ile Lys Ala Ile Met Asp
                325                 330                 335

Pro Asp Ser Lys Cys Lys Asp Asp Gly Asp Asp Asp Asp Glu Ser
            340                 345                 350

Val Lys Asn Val Lys Gln Arg Arg Ile Ser Gly Trp Asn Phe Asn Glu
        355                 360                 365

Asp Gly Leu Glu Leu Val Pro Val Phe Pro Lys Asp Gln Ser Lys Asp

-continued

```
            370                 375                 380
Asp Glu Val Val Lys Gln Val Arg Phe Glu Glu Glu Lys Val Ile Gln
385                 390                 395                 400

Glu Asp Ala Val Val Thr Ala Ser Gly Thr Val Met Glu Pro Lys Thr
                405                 410                 415

Asn Thr Ser Asp Val Val Asp His Glu Asn Val Gly Gly Val Val Lys
                420                 425                 430

Asn Arg Glu Ala Thr Leu Ala Thr Leu Asn Val Leu Lys Glu Ser Leu
            435                 440                 445

Glu Gln Glu Leu Gly Gln Val Lys Phe Leu Met Asn Leu Ile Gly Gly
        450                 455                 460

Glu Glu Ile His Val Ala Glu Ser Asp Glu Lys Met Val Gln Glu Ile
465                 470                 475                 480

Ser Lys Leu Arg Thr Glu Leu Glu Asn Glu Lys Lys Lys Asn Leu Gln
                485                 490                 495

Leu Glu Met Gln Leu Glu Asn Ile Lys Leu His Leu Ile Ser Ser Ala
            500                 505                 510

Ala Asn Ser Pro Thr Ser
            515
```

PLANT YIELD IMPROVEMENT BY STE20-LIKE GENE EXPRESSION

RELATED APPLICATIONS

This application is a national stage application (under 35 U.S.C. 371) of PCT/EP2006/063976 filed Jul. 6, 2006, which claims benefit of European application 05106135.6 filed Jul. 6, 2005 and U.S. Provisional application 60/697,338 filed Jul. 8, 2005.

SUBMISSION ON COMPACT DISC

The contents of the following submission on compact discs are incorporated herein by reference in its entirety: two copies of the Sequence Listing (COPY 1 and COPY 2) and a computer readable form copy of the Sequence Listing (CRF COPY), all on compact disc, each containing: file name: Sequence List-14546-00025-US, date recorded: Jan. 3, 2008, size: 112 KB.

The present invention relates generally to the field of molecular biology and concerns a method for increasing plant yield relative to control plants. More specifically, the present invention concerns a method for increasing plant yield comprising modulating expression in a plant of a nucleic acid encoding a Ste20-like polypeptide or a homologue thereof. The present invention also concerns plants having modulated expression of a nucleic acid encoding a Ste20-like polypeptide or a homologue thereof, which plants have increased yield relative to control plants. The invention also provides constructs useful in the methods of the invention.

The ever-increasing world population and the dwindling supply of arable land available for agriculture fuels research towards improving the efficiency of agriculture. Conventional means for crop and horticultural improvements utilise selective breeding techniques to identify plants having desirable characteristics. However, such selective breeding techniques have several drawbacks, namely that these techniques are typically labour intensive and result in plants that often contain heterogeneous genetic components that may not always result in the desirable trait being passed on from parent plants. Advances in molecular biology have allowed mankind to modify the germplasm of animals and plants. Genetic engineering of plants entails the isolation and manipulation of genetic material (typically in the form of DNA or RNA) and the subsequent introduction of that genetic material into a plant. Such technology has the capacity to deliver crops or plants having various improved economic, agronomic or horticultural traits. A trait of particular economic interest is yield, necessarily related to a specified crop, area and/or period of time. Yield is normally defined as the measurable produce of economic value from a crop. This may be defined in terms of quantity and/or quality. Yield is directly dependent on several factors, for example, the number and size of the organs, plant architecture (for example, the number of branches), seed production and more. Root development, nutrient uptake and stress tolerance may also be important factors in determining yield. Optimizing one of the above-mentioned factors may therefore contribute to increasing crop yield.

Plant biomass is yield for forage crops like alfalfa, silage corn and hay. Many proxies for yield have been used in grain crops. Chief amongst these are estimates of plant size. Plant size can be measured in many ways depending on species and developmental stage, but include total plant dry weight, above-ground dry weight, above-ground fresh weight, leaf area, stem volume, plant height, rosette diameter, leaf length, root length, root mass, tiller number and leaf number. Many species maintain a conservative ratio between the size of different parts of the plant at a given developmental stage. These allometric relationships are used to extrapolate from one of these measures of size to another (e.g. Tittonell et al 2005 Agric Ecosys & Environ 105: 213). Plant size at an early developmental stage will typically correlate with plant size later in development. A larger plant with a greater leaf area can typically absorb more light and carbon dioxide than a smaller plant and therefore will likely gain a greater weight during the same period (Fasoula & Tollenaar 2005 Maydica 50:39). This is in addition to the potential continuation of the micro-environmental or genetic advantage that the plant had to achieve the larger size initially. There is a strong genetic component to plant size and growth rate (e.g. ter Steege et al 2005 Plant Physiology 139:1078), and so for a range of diverse genotypes plant size under one environmental condition is likely to correlate with size under another (Hittalmani et al 2003 Theoretical Applied Genetics 107:679). In this way a standard environment is used as a proxy for the diverse and dynamic environments encountered at different locations and times by crops in the field.

Harvest index, the ratio of seed yield to above-ground dry weight, is relatively stable under many environmental conditions and so a robust correlation between plant size and grain yield can often be obtained (e.g. Rebetzke et al 2002 Crop Science 42:739). These processes are intrinsically linked because the majority of grain biomass is dependent on current or stored photosynthetic productivity by the leaves and stem of the plant (Gardener et al 1985 Physiology of Crop Plants. Iowa State University Press, pp 68-73) Therefore, selecting for plant size, even at early stages of development, has been used as an indicator for future potential yield (e.g. Tittonell et al 2005 Agric Ecosys & Environ 105: 213). When testing for the impact of genetic differences on stress tolerance, the ability to standardize soil properties, temperature, water and nutrient availability and light intensity is an intrinsic advantage of greenhouse or plant growth chamber environments compared to the field. However, artificial limitations on yield due to poor pollination due to the absence of wind or insects, or insufficient space for mature root or canopy growth, can restrict the use of these controlled environments for testing yield differences. Therefore, measurements of plant size in early development, under standardized conditions in a growth chamber or greenhouse, are standard practices to provide indication of potential genetic yield advantages.

Seed yield is a particularly important trait since the seeds of many plants are important for human and animal nutrition. Crops such as, corm, rice, wheat, canola and soybean account for over half the total human caloric intake, whether through direct consumption of the seeds themselves or through consumption of meat products raised on processed seeds. They are also a source of sugars, oils and many kinds of metabolites used in industrial processes. Seeds contain an embryo (the source of new shoots and roots) and an endosperm (the source of nutrients for embryo growth during germination and during early growth of seedlings). The development of a seed involves many genes, and requires the transfer of metabolites from the roots, leaves and stems into the growing seed. The endosperm, in particular, assimilates the metabolic precursors of carbohydrates, oils and proteins and synthesizes them into storage macromolecules to fill out the grain. The ability to increase plant seed yield, whether through seed number, seed biomass, seed development, seed filling, or any other seed-related trait would have many applications in agriculture, and even many non-agricultural uses such as in the biotechnological production of substances such as pharmaceuticals, antibodies or vaccines.

Ste20 is a Ser/Thr kinase belonging to the group of MAP4 kinases (MAP4Ks, MAP kinase kinase kinase kinases, or MAP3K kinases), and was for the first time isolated from yeast. MAP4K are kinases that activate MAP kinase cascades by directly phosphorylating MAP3Ks. A recent phylogenetic study discriminated 6 major groups of MAP4Ks, among which the STE20/PAK group of MAP4Ks (Champion et al., Trends Plant Sci. 9, 123-129, 2004). Most of the MAP4Ks have an N-terminal catalytic domain, although plant proteins homologous to Ste20 may have a different organisation. Members of the Ste20 group of kinases are believed to act as regulators of MAP kinase cascades (Dan et al., Trends Cell Biol. 11, 220-230, 2001), and are believed to act in particular upon MAP3 Kinases of the MEKK and Raf types, downstream of G-proteins (Champion et al., 2004). Yeast Ste20 plays a role in various signalling pathways, for example *Candida* Ste20 was shown to be involved in pheromone signalling, invasive growth, hypertonic stress response, cell wall integrity and in binding of CDC42, required for polarized morphogenesis (Calcagno et al., Yeast 21, 557-568, 2004). In *Drosophila*, the Ste20 homologue Hippo is reported to be involved in cell cycle progression (Udan et al., Nat. Cell Biol. 5, 853-855, 2003). In general, the effects of STE20/PAK directed signalling appear to be nuclear events that influence gene expression on the one hand, and cytoskeletal events that impact upon cellular dynamics (Bagrodia and Cerione, Trends Cell Biol. 9, 350-355, 1999). Although Ste20 and related proteins are relatively well studied in yeast, *Drosophila* and in mammalian cells, little or nothing is known about the plant homologues of yeast Ste20. Leprince et al. (Biochim. Biophys. Acta 1444, 1-13, 1999) have characterised a MAP4K from *Brassica napus*. Its expression seemed regulated by the cell cycle and transcripts were reported to most abundant in roots, siliques and flower buds. However, no mutants or transgenic plants were described.

Surprisingly, it has now been found that modulating expression in a plant of a nucleic acid encoding a Ste20-like polypeptide or a homologue thereof gives plants having increased yield relative to control plants. Preferably, the Ste20-like polypeptide or a homologue thereof is of plant origin.

Therefore, the invention provides a method for increasing plant yield, comprising modulating expression in a plant of a nucleic acid encoding a Ste20-like polypeptide or a homologue thereof.

Advantageously, performance of the methods according to the present invention results in plants having increased yield, particularly seed yield, relative to control plants.

The choice of control plants is a routine part of an experimental setup and may include corresponding wild type plants or corresponding plants without the gene of interest. The control plant is typically of the same plant species or even of the same variety as the plant to be compared. The control plant may also be a nullizygote of the plant to be compared. Nullizygotes are individuals missing the transgene by segregation. A "control plant" as used herein refers not only to whole plants, but also to plant parts, including seeds and seed parts.

A "reference", "reference plant", "control", "control plant", "wild type" or "wild type plant" is in particular a cell, a tissue, an organ, a plant, or a part thereof, which was not produced according to the method of the invention. Accordingly, the terms "wild type", "control" or "reference" are exchangeable and can be a cell or a part of the plant such as an organelle or tissue, or a plant, which was not modified or treated according to the herein described method according to the invention. Accordingly, the cell or a part of the plant such as an organelle or a plant used as wild type, control or reference corresponds to the cell, plant or part thereof as much as possible and is in any other property but in the result of the process of the invention as identical to the subject matter of the invention as possible. Thus, the wild type, control or reference is treated identically or as identical as possible, saying that only conditions or properties might be different which do not influence the quality of the tested property. That means in other words that the wild type denotes (1) a plant, which carries the unaltered or not modulated form of a gene or allele or (2) the starting material/plant from which the plants produced by the process or method of the invention are derived.

Preferably, any comparison between the wild type plants and the plants produced by the method of the invention is carried out under analogous conditions. The term "analogous conditions" means that all conditions such as, for example, culture or growing conditions, assay conditions (such as buffer composition, temperature, substrates, pathogen strain, concentrations and the like) are kept identical between the experiments to be compared.

The "reference", "control", or "wild type" is preferably a subject, e.g. an organelle, a cell, a tissue, a plant, which was not modulated, modified or treated according to the herein described process of the invention and is in any other property as similar to the subject matter of the invention as possible. The reference, control or wild type is in its genome, transcriptome, proteome or metabolome as similar as possible to the subject of the present invention. Preferably, the term "references-" "control-" or "wild type-"-organelle, -cell, -tissue or plant, relates to an organelle, cell, tissue or plant, which is nearly genetically identical to the organelle, cell, tissue or plant, of the present invention or a part thereof preferably 95%, more preferred are 98%, even more preferred are 99.00%, in particular 99.10%, 99.30%, 99.50%, 99.70%, 99.90%, 99.99%, 99, 999% or more. Most preferable the "reference", "control", or "wild type" is preferably a subject, e.g. an organelle, a cell, a tissue, a plant, which is genetically identical to the plant, cell organelle used according to the method of the invention except that nucleic acid molecules or the gene product encoded by them are changed, modulated or modified according to the inventive method.

In case, a control, reference or wild type differing from the subject of the present invention only by not being subject of the method of the invention can not be provided, a control, reference or wild type can be a plant in which the cause for the modulation of the activity conferring the increase of the metabolites as described under examples.

The term "yield" in general means a measurable produce of economic value, necessarily related to a specified crop, to an area, and to a period of time. Individual plant parts directly contribute to yield based on their number, size and/or weight. Whereas the actual yield is the yield per acre for a crop and year, which is determined by dividing total production (includes both harvested and appraised production) by planted acres.

The terms "increase", "improving" or "improve" are interchangeable and shall mean in the sense of the application at least a 5%, 6%, 7%, 8%, 9% or 10%, preferably at least 15% or 20%, more preferably 25%, 30%, 35% or 40% more yield and/or growth in comparison to the wild type plant as defined herein.

The increase referred to the activity of the polypeptide amounts in a cell, a tissue, a organelle, an organ or an organism or a part thereof preferably to at least 5%, preferably to at least 10% or at to least 15%, especially preferably to at least 20%, 25%, 30% or more, very especially preferably are to at least 40%, 50% or 60%, most preferably are to at least 70% or more in comparison to the control, reference or wild type.

The term "increased yield" as defined herein is taken to mean an increase in biomass (weight) of one or more parts of a plant, which may include aboveground (harvestable) parts and/or (harvestable) parts below ground.

In particular, such harvestable parts are seeds and leafy biomass, and performance of the methods of the invention results in plants having increased leafy biomass and increased seed yield relative to the seed yield of control plants.

Increased seed yield may manifest itself as one or more of the following: a) an increase in seed biomass (total seed weight) which may be on an individual seed basis and/or per plant and/or per hectare or acre; b) increased number of flowers per plant; c) increased number of (filled) seeds; d) increased seed filling rate (which is expressed as the ratio between the number of filled seeds divided by the total number of seeds; e) increased harvest index, which is expressed as a ratio of the yield of harvestable parts, such as seeds, divided by the total biomass; and f) increased thousand kernel weight (TKW), which is extrapolated from the number of filled seeds counted and their total weight. An increased TKW may result from an increased seed size and/or seed weight, and may also result from an increase in embryo and/or endosperm size.

The term "expression" or "gene expression" means the appearance of a phenotypic trait as a consequence of the transcription of a specific gene or specific genes. The term "expression" or "gene expression" in particular means the transcription of a gene or genes into structural RNA (rRNA, tRNA) or mRNA with subsequent translation of the latter into a protein. The process includes transcription of DNA, processing of the resulting mRNA product and its translation into an active protein.

The term "modulation" means in relation to expression or gene expression, a process in which the expression level is changed by said gene expression in comparison to the control plant, preferably the expression level is increased. The original, unmodulated expression may be of any kind of expression of a structural RNA (rRNA, tRNA) or mRNA with subsequent translation. The term "modulating the activity" shall mean any change of the expression of the inventive nucleic acid sequences or encoded proteins, which leads to increased yield and/or increased growth of the plants.

An increase in seed yield may also be manifested as an increase in seed size and/or seed volume, which may also influence the composition of seeds (including oil, protein and carbohydrate total content and composition). Furthermore, an increase in seed yield may also manifest itself as an increase in seed area and/or seed length and/or seed width and/or seed perimeter. Increased yield may also result in modified architecture, or may occur because of modified architecture.

Taking corn as an example, a yield increase may be manifested as one or more of the following: increase in the number of plants per hectare or acre, an increase in the number of ears per plant, an increase in the number of rows, number of kernels per row, kernel weight, thousand kernel weight, ear length/diameter, increase in the seed filling rate (which is the number of filled seeds divided by the total number of seeds and multiplied by 100), among others. Taking rice as an example, a yield increase may manifest itself as an increase in one or more of the following: number of plants per hectare or acre, number of panicles per plant, number of spikelets per panicle, number of flowers (florets) per panicle (which is expressed as a ratio of the number of filled seeds over the number of primary panicles), increase in the seed filling rate (which is the number of filled seeds divided by the total number of seeds and multiplied by 100), increase in thousand kernel weight, among others. An increase in yield may also result in modified architecture, or may occur as a result of modified architecture.

According to a preferred feature, performance of the methods of the invention result in plants having increased yield, particularly seed yield. Therefore, according to the present invention, there is provided a method for increasing plant yield, which method comprises modulating expression in a plant of a nucleic acid encoding a Ste20-like polypeptide or a homologue thereof.

Since the transgenic plants according to the present invention have increased yield, it is likely that these plants exhibit an increased growth rate (during at least part of their life cycle), relative to the growth rate of corresponding wild type plants at a corresponding stage in their life cycle. The increased growth rate may be specific to one or more parts of a plant (including seeds), or may be throughout substantially the whole plant. Plants having an increased growth rate may have a shorter life cycle. The life cycle of a plant may be taken to mean the time needed to grow from a dry mature seed up to the stage where the plant has produced dry mature seeds, similar to the starting material. This life cycle may be influenced by factors such as early vigour, growth rate, flowering time and speed of seed maturation. An increase in growth rate may take place at one or more stages in the life cycle of a plant or during substantially the whole plant life cycle. Increased growth rate during the early stages in the life cycle of a plant may reflect enhanced vigour. The increase in growth rate may alter the harvest cycle of a plant allowing plants to be sown later and/or harvested sooner than would otherwise be possible (a similar effect may be obtained with earlier flowering time). If the growth rate is sufficiently increased, it may allow for the further sowing of seeds of the same plant species (for example sowing and harvesting of rice plants followed by sowing and harvesting of further rice plants all within one conventional growing period). Similarly, if the growth rate is sufficiently increased, it may allow for the further sowing of seeds of different plants species (for example the sowing and harvesting of rice plants followed by, for example, the sowing and optional harvesting of soy bean, potato or any other plant). Harvesting additional times from the same rootstock in the case of some crop plants may also be possible. Altering the harvest cycle of a plant may lead to an increase in annual biomass production per acre (due to an increase in the number of times (say in a year) that any particular plant may be grown and harvested). An increase in growth rate may also allow for the cultivation of transgenic plants in a wider geographical area than their wild-type counterparts, since the territorial limitations for growing a crop are often determined by adverse environmental conditions either at the time of planting (early season) or at the time of harvesting (late season). Such adverse conditions may be avoided if the harvest cycle is shortened. The growth rate may be determined by deriving various parameters from growth curves, such parameters may be: T-Mid (the time taken for plants to reach 50% of their maximal size) and T-90 (time taken for plants to reach 90% of their maximal size), amongst others.

According to a preferred feature of the present invention, performance of the methods of the invention gives plants having an increased growth rate or increased yield in comparison to control plants. Therefore, according to the present invention, there is provided a method for increasing yield and/or the growth rate of plants, which method comprises modulating, preferably increasing, expression in a plant of a nucleic acid encoding a Ste20-like protein.

An increase in yield and/or growth rate occurs whether the plant is under non-stress conditions or whether the plant is exposed to various stresses compared to control plants. Plants typically respond to exposure to stress by growing more slowly. In conditions of severe stress, the plant may even stop growing altogether. Mild stress on the other hand is defined herein as being any stress to which a plant is exposed which does not result in the plant ceasing to grow altogether without the capacity to resume growth. Mild stress in the sense of the invention leads to a reduction in the growth of the stressed plants of less than 40%, 35% or 30%, preferably less than 25%, 20% or 15%, more preferably less than 14%, 13%, 12%, 11% or 10% or less in comparison to the control plant under non-stress conditions. Due to advances in agricultural practices (irrigation, fertilization, pesticide treatments) severe stresses are not often encountered in cultivated crop plants. As a consequence, the compromised growth induced by mild stress is often an undesirable feature for agriculture. Mild stresses are the typical stresses to which a plant may be exposed. These stresses may be the everyday biotic and/or abiotic (environmental) stresses to which a plant is exposed. Typical abiotic or environmental stresses include temperature stresses caused by atypical hot or cold/freezing temperatures; salt stress; water stress (drought or excess water). Chemicals may also cause abiotic stresses. Biotic stresses are typically those stresses caused by pathogens, such as bacteria, viruses, fungi and insects. In another preferred embodiment of the invention an increase in yield and/or growth rate occurs according to the method of invention under non-stress or mild abiotic or biotic stress conditions, preferably on non-stress or mild abiotic stress conditions.

The abovementioned growth characteristics may advantageously be modified in any plant.

The term "plant" as used herein encompasses whole plants, ancestors and progeny of the plants, plant cells and plant parts, including seeds, shoots, stems, leaves, roots (including tubers), flowers, and tissues and organs, wherein each of the aforementioned comprise the gene/nucleic acid of interest. The term "plant" also encompasses suspension cultures, callus tissue, embryos, meristematic regions, gametophytes, sporophytes, pollen and microspores, again wherein each of the aforementioned comprise the gene/nucleic acid of interest.

Plants that are particularly useful in the methods of the invention include all plants which belong to the superfamily Viridiplantae, in particular monocotyledonous and dicotyledonous plants including fodder or forage legumes, ornamental plants, food crops, trees or shrubs selected from the list comprising *Acer* spp., *Actinidia* spp., *Abelmoschus* spp., *Agropyron* spp., *Allium* spp., *Amaranthus* spp., *Ananas comosus*, *Annona* spp., *Apium graveolens*, *Arabidopsis thaliana*, *Archis* spp, *Artocarpus* spp., *Asparagus officinalis*, *Avena sativa*, *Averrhoa carambola*, *Benincasa hispida*, *Bertholletia excelsea*, *Beta vulgaris*, *Brassica* spp., *Cadaba farinosa*, *Camellia sinensis*, *Canna indica*, *Capsicum* spp., *Carex elata*, *Carica papaya*, *Carissa macrocarpa*, *Carya* spp., *Carthamus tinctorius*, *Castanea* spp., *Cichorium endivia*, *Cinnamomum* spp., *Citrullus lanatus*, *Citrus* spp., *Cocos* spp., *Coffea* spp., *Colocasia esculenta*, *Cola* spp., *Coriandrum sativum*, *Corylus* spp., *Crataegus* spp., *Crocus sativus*, *Cucurbita* spp., *Cucumis* spp., *Cynara* spp., *Daucus carota*, *Desmodium* spp., *Dimocarpus longan*, *Dioscorea* spp., *Diospyros* spp., *Echinochloa* spp., *Eleusine coracana*, *Eriobotrya japonica*, *Eugenia uniflora*, *Fagopyrum* spp., *Fagus* spp., *Ficus carica*, *Fortunelia* spp., *Fragaria* spp., *Ginkgo biloba*, *Glycine* spp., *Gossypium hirsutum*, *Helianthus* spp., *Hemerocallis fulva*, *Hibiscus* spp., *Hordeum* spp., *Ipomoea batatas*, *Juglans* spp., *Lactuca sativa*, *Lathyrus* spp., *Lens culinaris*, *Linum usitatissimum*, *Litchi chinensis*, *Lotus* spp., *Luffa acutangula*, *Lupinus* spp., *Luzula sylvatica*, *Macrotyloma* spp., *Malus* spp., *Malpighia emarginata*, *Mammea americana*, *Mangifera indica*, *Manihot* spp., *Manilkara zapota*, *Medicago sativa*, *Melilotus* spp., *Mentha* spp., *Momordica* spp., *Morus nigra*, *Musa* spp., *Nicotiana* spp., *Olea* spp., *Opuntia* spp., *Ornithopus* spp., *Oryza* spp., *Panicum miliaceum*, *Passiflora edulis*, *Pastinaca sativa*, *Persea* spp., *Petroselinum crispum*, *Phaseolus* spp., *Phoenix* spp., *Physalis* spp., *Pinus* spp., *Pistacia vera*, *Pisum* spp., *Poa* spp., *Populus* spp., *Prosopis* spp., *Prunus* spp., *Psidium* spp., *Punica granatum*, *Pyrus communis*, *Quercus* spp., *Raphanus sativus*, *Rheum rhabarbarum*, *Ribes* spp., *Rubus* spp., *Saccharum* spp., *Sambucus* spp., *Secale cereale*, *Sesamum* spp., *Sinapis* sp., *Solanum* spp., *Sorghum bicolor*, *Spinacia* spp., *Syzygium* spp., *Tamarindus indica*, *Theobroma cacao*, *Trifolium* spp., *Triticosecale rimpaui*, *Triticum* spp., *Tropaeolum minus*, *Tropaeolum majus*, *Vaccinium* spp., *Vicia* spp., *Vigna* spp., *Viola odorata*, *Vitis* spp., *Zea mays*, *Zizania palustris*, *Ziziphus* spp., amongst others. According to a preferred embodiment of the present invention, the plant is a crop plant such as soybean, sunflower, canola, alfalfa, rapeseed, cotton, tomato, potato or tobacco. Further preferably, the plant is a monocotyledonous plant, such as sugar cane. More preferably the plant is a cereal, such as rice, maize, wheat, barley, millet, rye, sorghum or oats.

Other advantageous plants are selected from the group consisting of Asteraceae such as the genera Helianthus, Tagetes e.g. the species Helianthus annus [sunflower], *Tagetes lucida*, *Tagetes erecta* or *Tagetes tenuifolia* [Marigold], Brassicaceae such as the genera *Brassica*, *Arabadopsis* e.g. the species *Brassica napus*, *Brassica rapa* ssp. [canola, oilseed rape, turnip rape] or *Arabidopsis thaliana*. Fabaceae such as the genera *Glycine* e.g. the species *Glycine max*, *Soja hispida* or *Soja max* [soybean]. Linaceae such as the genera *Linum* e.g. the species *Linum usitatissimum*, [flax, linseed]; Poaceae such as the genera *Hordeum*, *Secale*, *Avena*, *Sorghum*, *Oryza*, *Zea*, *Triticum* e.g. the species *Hordeum vulgare* [barley]; *Secale cereale* [rye], *Avena sativa*, *Avena fatua*, *Avena byzantina*, *Avena fatua* var. sativa, *Avena hybrida* [oat], *Sorghum bicolor* [Sorghum, millet], *Oryza sativa*, *Oryza latifolia* [rice], *Zea mays* [corn, maize] *Triticum aestivum*, *Triticum durum*, *Triticum turgidum*, *Triticum hybernum*, *Triticum macha*, *Triticum sativum* or *Triticum vulgare* [wheat, bread wheat, common wheat]; Solanaceae such as the genera *Solanum*, *Lycopersicon* e.g. the species *Solanum tuberosum* [potato], *Lycopersicon esculentum*, *Lycopersicon lycopersicum*, *Lycopersicon pyriforme*, *Solanum integrifolium* or *Solanum lycopersicum* [tomato].

The term "Ste20-like polypeptide or homologue thereof" as defined herein refers to a MAP4K polypeptide, preferably of plant origin, comprising an N-terminal Ser/Thr kinase domain (matching the SMART database entry SM00220, InterPro accession IPR002290). The kinase domain in SEQ ID NO: 2 starts at Y15 and ends at F293, and comprises the ProSite Ser/Thr protein kinase pattern PS00108:

[LIVMFYC]-x-[HY]-x-D-[LIVMFY]-K-x(2)-N-[LIVM-FYCT](3), wherein the first x is missing. Preferably, the Ste20-like polypeptide or homologue thereof comprises the Ste20 signature sequence:

(SEQ ID NO: 6; Dan et al., 2001)
G(T/N)P(Y/C/R)(W/R)MAPE(V/K), more preferably it comprises the sequence motif:

(S/H/N)(I/L)(V/I/L/M)(S/K)(S/H/T/A/I/V)(S/G/V/A)(F/Y)(P/Q)(S/N/D/E)G,  (SEQ ID NO: 7)

most preferably the Ste20-like polypeptide or homologue thereof comprises at least one of the following sequence motifs:

SEQ ID NO: 8,  (V/I)HSH(T/N/V)GY(G/S)(F/I)

SEQ ID NO: 9,  RPPLSHLPP(L/S)KS

SEQ ID NO: 10, RRISGWNF

At the C-terminal end of the protein, a coiled coil motif may be present (K450 to T477 in SEQ ID NO: 2).

The term "domain" refers to a set of amino acids conserved at specific positions along an alignment of sequences of evolutionarily related proteins. While amino acids at other positions can vary between homologues, amino acids that are highly conserved at specific positions indicate amino acids that are essential in the structure, the stability, or the activity of a protein. Identified by their high degree of conservation in aligned sequences of a family of protein homologues, they can be used as identifiers to determine if any polypeptide in question belongs to a previously identified polypeptide family (in this case, the family of Ste20-like proteins). The term "motif" refers to a short conserved region in a protein sequence. Motifs are frequently highly conserved parts of domains, but may also include only part of the domain, or be located outside of conserved domain (if all of the amino acids of the motif fall outside of a defined domain).

Specialist databases exist for the identification of domains. The kinase domain in a Ste20-like protein may be identified using, for example, SMART (Schultz et al. (1998) Proc. Natl. Acad. Sci. USA 95, 5857-5864; Letunic et al. (2002) Nudeic Acids Res 30, 242-244), Interpro (Mulder et al., (2003) Nud. Acids. Res. 31, 315-318), Prosite (Bucher and Bairoch (1994), A generalized profile syntax for biomolecular sequences motifs and its function in automatic sequence interpretation. (In) ISMB-94; Proceedings 2nd International Conference on Intelligent Systems for Molecular Biology. Altman R., Brutlag D., Karp P., Lathrop R., Searls D., Eds., pp 53-61, AAAIPress, Menlo Park; Hulo et al., Nucl. Acids. Res. 32:D134-D137, (2004)) or Pfam (Bateman et al., Nucleic Acids Research 30(1): 276-280 (2002)). A set of tools for in silico analysis of protein sequences is available on the ExPASY proteomics server (hosted by the Swiss Institute of Bioinformatics (Gasteiger et al., ExPASy: the proteomics server for in-depth protein knowledge and analysis, Nucleic Acids Res. 31:3784-3788 (2003)).

By aligning other protein sequences with SEQ ID NO: 2, the corresponding Ste20 signature sequence, the kinase domain and other sequence motifs detailed above may easily be identified. In this way, Ste20-like polypeptides or homologues thereof (encompassing orthologues and paralogues) may readily be identified, using routine techniques well known in the art, such as by sequence alignment. Methods for the alignment of sequences for comparison are well known in the art, such methods include GAP, BESTFIT, BLAST, FASTA and TFASTA. GAP uses the algorithm of Needleman and Wunsch ((1970) J Mol Biol 48: 443-453) to find the alignment of two complete sequences that maximizes the number of matches and minimizes the number of gaps. The BLAST algorithm (Altschul et al. (1990) J Mol Biol 215: 403-10) calculates percent sequence identity and performs a statistical analysis of the similarity between the two sequences. The software for performing BLAST analysis is publicly available through the National Centre for Biotechnology Information. Homologues may readily be identified using, for example, the ClustalW multiple sequence alignment algorithm (version 1.83), with the default pairwise alignment parameters, and a scoring method in percentage. Global percentages of similarity and identity may also be determined using one of the methods available in the MatGAT software package (Campanella et al., BMC Bioinformatics. 2003 Jul. 10; 4:29. MatGAT: an application that generates similarity/identity matrices using protein or DNA sequences.). Minor manual editing may be performed to optimise alignment between conserved motifs, as would be apparent to a person skilled in the art. Furthermore, instead of using full length sequences for the identification of homologues, specific domains (such as the kinase domain) may be used as well. The sequence identity values, which are indicated above as a percentage were determined over the entire conserved domain or nucleic acid or amino acid sequence using the programs mentioned above using the default parameters.

Examples of Ste20-like polypeptides or homologues thereof include the *Arabidopsis* sequences SEQ ID NO: 12 (corresponding to At5g14720, encoded by GenBank accession number AAL38867), SEQ ID NO: 14 (At1g70430, GenBank NP_177200), SEQ ID NO: 16 (At1g23700, GenBank NP_173782), SEQ ID NO: 18 (At1g79640, GenBank NP_178082), SEQ ID NO: 20 (At4g10730, GenBank NP_192811), SEQ ID NO: 22 (At4g24100, GenBank NP_194141); the rice sequences SEQ ID NO: 24 (GenBank XP_469286, the rice orthologue of SEQ ID NO: 2), SEQ ID NO: 26 (GenBank BAD37346), SEQ ID NO: 28 (GenBank XP_468215), SEQ ID NO: 30 (GenBank AAL54869), SEQ ID NO: 32 (GenBank NP_912431) and the Medicago sequence SEQ ID NO: 34 (orthologue of SEQ ID NO: 2).

It is to be understood that sequences falling under the definition of "Ste20-like polypeptide or homologue thereof" are not to be limited to the sequences represented by SEQ ID NO: 2, SEQ ID NO: 12, SEQ ID NO: 14, SEQ ID NO: 16, SEQ ID NO: 18, SEQ ID NO: 20, SEQ ID NO: 22, SEQ ID NO: 24, SEQ ID NO: 26, SEQ ID NO: 28, SEQ ID NO: 30, SEQ ID NO: 32 or SEQ ID NO: 34, but that any polypeptide comprising a N-terminal kinase domain as defined above, the Ste20 signature sequence and preferably also one or more of the sequence motifs detailed in SEQ ID NO: 7, 8, 9 and 10, may be suitable for use in the methods of the invention. In a preferred embodiment, the homologue used in the methods of the present invention is an othologue of SEQ ID NO: 2.

An assay may be carried out to determine Ste20-like activity. For example to determine the kinase activity, several assays are available and well known in the art (for example Current Protocols in Molecular Biology, Volumes 1 and 2, Ausubel et al. (1994), Current Protocols). The Ste20-like protein is a MAP4K kinase involved in signal transduction. For several organisms, the substrate of Ste20 was identified as Ste11p (Drogen et al., Current Biology 10, 630-639, 2000). Besides in vit phosphorylation of the Ste11 p protein, Ste20 was also shown to phosphorylate histone H2B (Ahn et al., Cell 120, 25-36, 2005). Buffer composition, ionic strength, and pH may be optimized starting from a standard kinase assay mixture. A standard 5× Kinase Buffer generally contains 5 mg/ml BSA (Bovine Serum Albumin preventing kinase adsorption to the assay tube), 150 mM Tris-Cl (pH 7.5), 100 mM $MgCl_2$. Divalent cations are required for most tyrosine kinases, although some tyrosine kinases (for example, insulin-, IGF-1-, and PDGF receptor kinases) require $MnCl_2$ instead of $MgCl_2$ (or in addition to $MgCl_2$). The optimal concentrations of divalent cations must be determined empirically for each protein kinase. A commonly used donor for the phophoryl group is radio-labelled [gamma-$^{32}$P] ATP (normally at 0.2 mM final concentration). The amount of $^{32}$P incorporated in the peptides may be determined by measuring activity on the nitrocellulose dry pads in a scintillation counter.

Furthermore, expression of the Ste20-like protein or of a homologue thereof in plants, and in particular in rice, has the effect of increasing yield of the transgenic plant when compared to control plants, wherein increased yield comprises at least one of: total weight of seeds, number of filled seeds and harvest index.

"Homologues" of a protein encompass peptides, oligopeptides, polypeptides, proteins and enzymes having amino acid substitutions, deletions and/or insertions relative to the unmodified protein in question and having similar biological and functional activity as the unmodified protein from which they are derived.

Encompassed by the term "homologues" are orthologous sequences and paralogous sequences, two special forms of homology which encompass evolutionary concepts used to describe ancestral relationships of genes. Paralogues are genes within the same species that have originated through duplication of an ancestral gene and orthologues are genes from different organisms that have originated through speciation.

Orthologues and paralogues may easily be found by performing a so-called reciprocal blast search. This may be done by a first BLAST involving BLASTing a query sequence (for example, SEQ ID NO: 1 or SEQ ID NO: 2) against any sequence database, such as the publicly available NCBI database. BLASTN or TBLASTX (using standard default values) may be used when starting from a nucleotide sequence and BLASTP or TBLASTN (using standard default values) may be used when starting from a protein sequence. The BLAST results may optionally be filtered. The full-length sequences of either the filtered results or non-filtered results are then BLASTed back (second BLAST) against sequences from the organism from which the query sequence is derived (where the query sequence is SEQ ID NO: 1 or SEQ ID NO: 2, the second BLAST would therefore be against *Arabidopsis* sequences). The results of the first and second BLASTs are then compared. A paralogue is identified if a high-ranking hit from the second BLAST is from the same species as from which the query sequence is derived; an orthologue is identified if a high-ranking hit is not from the same species as from which the query sequence is derived. Preferred orthologues are orthologues of SEQ ID NO: 1 or SEQ ID NO: 2. High-ranking hits are those having a low E-value. The lower the E-value, the more significant the score (or in other words the lower the chance that the hit was found by chance). Computation of the E-value is well known in the art. In addition to E-values, comparisons are also scored by percentage identity. Percentage identity refers to the number of identical nucleotides (or amino acids) between the two compared nucleic acid (or polypeptide) sequences over a particular length. Preferably the score is greater than 50, more preferably greater than 100; and preferably the E-value is less than e-5, more preferably less than e-6. In the case of large families, ClustalW may be used, followed by the generation of a neighbour joining tree, to help visualize clustering of related genes and to identify orthologues and paralogues. Examples of sequences orthologous to SEQ ID NO: 2 include SEQ ID NO: 24 and SEQ ID NO: 34. Examples of paralogues of SEQ ID NO: 2 include SEQ ID NO: 12 (At5g14720) and SEQ ID NO: 20 (At4g10730).

Preferably, the kinase domains of Ste20-like proteins useful in the methods of the present invention have, in increasing order of preference, at least 40%, 45%, 50%, 55%, 60%, 65%, 70%, 75%, 80%, 85%, 90%, 95%, 96%, 97%, 98% or 99% sequence identity to the kinase domain of the Ste20 protein of SEQ ID NO: 2. An example detailing the identification of homologues is given in Example 1. The matrix shown in Example 1 (Table 4) shows similarities and identities (in bold) over the full-length of the protein. In case only specific domains are compared, the identity or similarity may be higher among the different proteins (Table 5: comparison of the kinase domains only).

A Ste20-like polypeptide or homologue thereof is encoded by a Ste20-like nucleic acid/gene. Therefore the term "Ste20-like nucleic acid/gene" as defined herein is any nucleic acid/gene encoding a Ste20-like polypeptide or a homologue thereof as defined above.

Examples of Ste20-like nucleic acids include but are not limited to those represented by any one of SEQ ID NO: 3, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 or SEQ ID NO: 33.

Ste20-like nucleic acids/genes and variants thereof may be suitable in practising the methods of the invention. Variant Ste20-like nucleic acid/genes include portions of a Ste20-like nucleic acid/gene, splice variants, allelic variants and/or nucleic acids capable of hybridising with a Ste20-like nucleic acid/gene.

The term portion as defined herein refers to a piece of DNA encoding a polypeptide comprising the Ste20 signature sequence G(T/N)P(Y/C/R)(W/R)MAPE(V/K) (SEQ ID NO: 6) and a N-terminal Ser/Thr kinase domain as defined above. A portion may be prepared, for example, by making one or more deletions to a Ste20-like nucleic acid. The portions may be used in isolated form or they may be fused to other coding (or non-coding) sequences in order to, for example, produce a protein that combines several activities. When fused to other coding sequences, the resulting polypeptide produced upon translation may be bigger than that predicted for the Ste20-like fragment. The portion is typically at least 300, 400, 500, 600 or 700 nucleotides in length, preferably at least 750, 900, 850, 900 or 950 nucleotides in length, more preferably at least 1000, 1100, 1200 or 1300 nucleotides in length and most preferably at least 1350, 1400 or 1450 nucleotides in length. Preferably, the portion is a portion of a nucleic add as represented by any one of SEQ ID NO: 1, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 or SEQ ID NO: 33. Most preferably the portion of a nucleic add is as represented by SEQ ID NO: 1.

The terms "fragment", "fragment of a sequence" or "part of a sequence" "portion" or "portion thereof" mean a truncated sequence of the original sequence referred to. The truncated sequence (nucleic acid or protein sequence) can vary widely in length; the minimum size being a sequence of sufficient size to provide a sequence with at least a comparable function and/or activity of the original sequence referred to or hybridizing with the nucleic acid molecule of the invention or used in the process of the invention under stringend conditions, while the maximum size is not critical. In some applications, the maximum size usually is not substantially greater than that required to provide the desired activity and/or function(s) of the original sequence. A comparable function means at least 40%, 45% or 50%, preferably at least 60%, 70%, 80% or 90% or more of the original sequence.

Another variant of a Ste20-like nucleic acid/gene is a nucleic acid capable of hybridising under reduced stringency conditions, preferably under stringent conditions, with a Ste20-like nucleic acid/gene as hereinbefore defined or with a portion as defined hereinabove.

Hybridising sequences useful in the methods of the present invention encode a polypeptide having a Ste20 signature sequence G(T/N)P(Y/C/R)(W/R)MAPE(V/K) (SEQ ID NO: 6) and a N-terminal Ser/Thr kinase domain as defined above and having substantially the same biological activity as the Ste20-like protein represented by SEQ ID NO: 2 or homologues thereof. The hybridizing sequence is typically at least 800 nucleotides in length, preferably at least 1000 nucleotides in length, more preferably at least 1200 nucleotides in length and most preferably at least 1400 nucleotides in length.

Preferably, the hybridising sequence is one that is capable of hybridising to a nucleic acid as represented by (or to probes derived from) SEQ ID NO: 1, SEQ ID NO: 3, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 or SEQ ID NO: 33, or to a portion of any of the aforementioned sequences, a portion being as defined above. Most preferably the hybridising sequence is capable of hybridising to SEQ ID NO: 1, or to portions (or probes) thereof. Methods for designing probes are well known in the art. Probes are generally less than 1000 bp, 900 bp, 800 bp, 700 bp, 600 bp in length, preferably less than 500 bp, 400 bp, 300 bp 200 bp or 100 bp in length. Commonly, probe lengths for DNA-DNA hybridisations such as Southern blotting, vary between 100 and 500 bp, whereas the hybridising region in probes for DNA-DNA hybridisations such as in PCR amplification generally are shorter than 50 but longer than 10 nucleotides, preferably they are 15, 20, 25, 30, 35, 40, 45 or 50 bp in length.

The term "hybridisation" as defined herein is a process wherein substantially homologous complementary nucleotide sequences anneal to each other. The hybridisation process can occur entirely in solution, i.e. both complementary nucleic acids are in solution. The hybridisation process can also occur with one of the complementary nucleic acids immobilised to a matrix such as magnetic beads, Sepharose beads or any other resin. The hybridisation process can furthermore occur with one of the complementary nucleic acids immobilised to a solid support such as a nitro-cellulose or nylon membrane or immobilised by e.g. photolithography to, for example, a siliceous glass support (the latter known as nucleic acid arrays or micro-arrays or as nucleic acid chips). In order to allow hybridisation to occur, the nucleic acid molecules are generally thermally or chemically denatured to melt a double strand into two single strands and/or to remove hairpins or other secondary structures from single stranded nucleic acids.

The term "stringency" refers to the conditions under which a hybridisation takes place. The stringency of hybridisation is influenced by conditions such as temperature, salt concentration, ionic strength and hybridisation buffer composition. Generally, low stringency conditions are selected to be about 30° C. lower than the thermal melting point ($T_m$) for the specific sequence at a defined ionic strength and pH. Medium stringency conditions are when the temperature is 20° C. below $T_m$, and high stringency conditions are when the temperature is 10° C. below $T_m$. High stringency hybridisation conditions are typically used for isolating hybridising sequences that have high sequence similarity to the target nucleic acid sequence. However, nucleic acids may deviate in sequence and still encode a substantially identical polypeptide, due to the degeneracy of the genetic code. Therefore medium stringency hybridisation conditions may sometimes be needed to identify such nucleic acid molecules.

The $T_m$ is the temperature under defined ionic strength and pH, at which 50% of the target sequence hybridises to a perfectly matched probe. The $T_m$ is dependent upon the solution conditions and the base composition and length of the probe. For example, longer sequences hybridise specifically at higher temperatures. The maximum rate of hybridisation is obtained from about 16° C. up to 32° C. below $T_m$. The presence of monovalent cations in the hybridisation solution reduce the electrostatic repulsion between the two nucleic acid strands thereby promoting hybrid formation; this effect is visible for sodium concentrations of up to 0.4M (for higher concentrations, this effect may be ignored). Formamide reduces the melting temperature of DNA-DNA and DNA-RNA duplexes with 0.6 to 0.7° C. for each percent formamide, and addition of 50% formamide allows hybridisation to be performed at 30 to 45° C., though the rate of hybridisation will be lowered. Base pair mismatches reduce the hybridisation rate and the thermal stability of the duplexes. On average and for large probes, the $T_m$ decreases about 1° C. per % base mismatch. The $T_m$ may be calculated using the following equations, depending on the types of hybrids:

1). DNA-DNA hybrids (Meinkoth and Wahl, Anal. Biochem., 138: 267-284, 1984):

$$T_m = 81.5° C. + 16.6 \times \log_{10}[Na+]^a + 0.41 \times \%[G/C^b] - 500 \times [L^c]^{-1} - 0.61 \times \% \text{ formamide}$$

2). DNA-RNA or RNA-RNA hybrids:

$$Tm = 79.8 + 18.5(\log_{10}[Na+]^a) + 0.58 (\% G/C^b) + 11.8(\% G/C^b)^2 - 820/L^c$$

3). oligo-DNA or oligo-RNA$^d$ hybrids:
For <20 nucleotides: Tm=2 ($I_n$)
For 20-35 nucleotides: Tm=22+1.46 ($I_n$)

$^a$ or for other monovalent cation, but only accurate in the 0.01-0.4 M range.
$^b$ only accurate for % GC in the 30% to 75% range.
$^c$ L=length of duplex in base pairs.
$^d$ Oligo, oligonucleotide; $I_n$, effective length of primer=2× (no. of G/C)+(no. of A/T).

Non-specific binding may be controlled using any one of a number of known techniques such as, for example, blocking the membrane with protein containing solutions, additions of heterologous RNA, DNA, and SDS to the hybridisation buffer, and treatment with Rnase. For non-homologous probes, a series of hybridizations may be performed by varying one of (i) progressively lowering the annealing temperature (for example from 68° C. to 42° C.) or (ii) progressively lowering the formamide concentration (for example from 50% to 0%). The skilled artisan is aware of various parameters which may be altered during hybridisation and which will either maintain or change the stringency conditions.

Besides the hybridisation conditions, specificity of hybridisation typically also depends on the function of post-hybridisation washes. To remove background resulting from non-specific hybridisation, samples are washed with dilute salt solutions. Critical factors of such washes include the ionic strength and temperature of the final wash solution: the lower the salt concentration and the higher the wash temperature, the higher the stringency of the wash. Wash conditions are typically performed at or below hybridisation stringency.

A positive hybridisation gives a signal that is at least twice of that of the background. Generally, suitable stringent conditions for nucleic acid hybridisation assays or gene amplification detection procedures are as set forth above. More or less stringent conditions may also be selected. The skilled artisan is aware of various parameters which may be altered during washing and which will either maintain or change the stringency conditions.

For example, typical high stringency hybridisation conditions for DNA hybrids longer than 50 nucleotides encompass hybridisation at 65° C. in 1×SSC or at 42° C. in 1×SSC and 50% formamide, followed by washing at 65° C. in 0.3×SSC. Examples of medium stringency hybridisation conditions for DNA hybrids longer than 50 nucleotides encompass hybridisation at 50° C. in 4×SSC or at 40° C. in 6×SSC and 50% formamide, followed by washing at 50° C. in 2×SSC. The length of the hybrid is the anticipated length for the hybridising nucleic acid. When nucleic acids of known sequence are hybridised, the hybrid length may be determined by aligning the sequences and identifying the conserved regions described herein. 1×SSC is 0.15M NaCl and 15 mM sodium citrate; the hybridisations and washes may additionally include 5×Denhardt's reagent, 0.5-1.0% SDS, 100 µg/ml denatured, fragmented salmon sperm DNA, 0.5% sodium pyrophosphate.

For the purposes of defining the level of stringency, reference can conveniently be made to Sambrook et al. (2001) Molecular Cloning: a laboratory manual, 3rd Edition Cold Spring Harbor Laboratory Press, CSH, New York, or to Current Protocols in Molecular Biology, John Wiley & Sons, N.Y. (1989 and yearly updates).

Also useful in the methods of the invention are nucleic acids encoding homologues of the amino acid sequence represented by SEQ ID NO 2.

A homologue may be in the form of a "substitutional variant" of a protein, i.e. where at least one residue in an amino acid sequence has been removed and a different residue inserted in its place. Amino acid substitutions are typically of single residues, but may be clustered depending upon functional constraints placed upon the polypeptide; insertions will usually be of the order of about 1 to 10 amino acid residues. Preferably, amino acid substitutions comprise conservative amino acid substitutions. To produce such homologues, amino acids of the protein may be replaced by other amino acids having similar properties (such as similar hydrophobicity, hydrophilicity, antigenicity, propensity to form or break α-helical structures or β-sheet structures). Conservative substitution tables are well known in the art (see for example Creighton (1984) Proteins. W.H. Freeman and Company and Table 1 below).

TABLE 1

Examples of conserved amino acid substitutions

| Residue | Conservative Substitutions |
|---|---|
| Ala | Ser |
| Arg | Lys |
| Asn | Gln; His |
| Asp | Glu |
| Gln | Asn |
| Cys | Ser |
| Glu | Asp |
| Gly | Pro |
| His | Asn; Gln |
| Ile | Leu, Val |
| Leu | Ile; Val |
| Lys | Arg; Gln |

TABLE 1-continued

Examples of conserved amino acid substitutions

| Residue | Conservative Substitutions |
|---|---|
| Met | Leu; Ile |
| Phe | Met; Leu; Tyr |
| Ser | Thr; Gly |
| Thr | Ser; Val |
| Trp | Tyr |
| Tyr | Trp; Phe |
| Val | Ile; Leu |

A homologue may also be in the form of an "insertional variant" of a protein, i.e. where one or more amino acid residues are introduced into a predetermined site in a protein. Insertions may comprise N-terminal and/or C-terminal fusions as well as intra-sequence insertions of single or multiple amino acids. Generally, insertions within the amino acid sequence will be smaller than N- or C-terminal fusions, of the order of about 1 to 10 residues. Examples of N- or C-terminal fusion proteins or peptides include the binding domain or activation domain of a transcriptional activator as used in the yeast two-hybrid system, phage coat proteins, (histidine)-6-tag, glutathione S-transferase-tag, protein A, maltose-binding protein, dihydrofolate reductase, Tag-100 epitope, c-myc epitope, FLAG-epitope, lacZ, CMP (calmodulin-binding peptide), HA epitope, protein C epitope and VSV epitope.

Homologues in the form of "deletion variants" of a protein are characterised by the removal of one or more amino acids from a protein.

Amino acid variants of a protein (substitution-, deletion- and/or insertion-variants) may readily be made using peptide synthetic techniques well known in the art, such as solid phase peptide synthesis and the like, or by recombinant DNA manipulations. Methods for the manipulation of DNA sequences to produce substitution, insertion or deletion variants of a protein are well known in the art. For example, techniques for making substitution mutations at predetermined sites in DNA are well known to those skilled in the art and include M13 mutagenesis, T7-Gen in vito mutagenesis (USB, Cleveland, Ohio), QuickChange Site Directed mutagenesis (Stratagene, San Diego, Calif.), PCR-mediated site-directed mutagenesis or other site-directed mutagenesis protocols.

The Ste20-like polypeptide or homologue thereof may also be a derivative. "Derivatives" include peptides, oligopeptides, polypeptides, proteins and enzymes which may comprise substitutions, deletions or additions of naturally and non-naturally occurring amino acid residues compared to the amino acid sequence of a naturally-occurring form of the protein, for example, as presented in SEQ ID NO: 2. "Derivatives" include peptides, oligopeptides, polypeptides which may, compared to the amino acid sequence of the naturally-occurring form of the protein, such as the one presented in SEQ ID NO: 2, comprise substitutions of amino acids with non-naturally occurring amino acid residues, or additions of non-naturally occurring amino acid residues. "Derivatives" of a protein also encompass peptides, oligopeptides, polypeptides which may comprise naturally occurring altered (glycosylated, acylated, ubiquinated, prenylated, phosphorylated, myristoylated, sulphated etc) or non-naturally altered amino acid residues compared to the amino acid sequence of a naturally-occurring form of the polypeptide. A derivative may also comprise one or more non-amino acid substituents or additions compared to the amino acid sequence from which it is derived, for example a reporter molecule or other ligand, covalently or non-covalently bound to the amino acid sequence, such as a reporter molecule which is bound to facilitate its detection, and non-naturally occurring amino acid residues relative to the amino acid sequence of a naturally-occurring protein. Derivatives of orthologues or paralogues of SEQ ID NO: 2 are further examples which may be suitable for use in the methods of the invention.

The Ste20-like polypeptide or homologue thereof may be encoded by a splice variant of a Ste20-like nucleic acid/gene. The term "splice variant" as used herein encompasses variants of a nucleic acid sequence in which selected introns and/or exons have been excised, replaced, displaced or added, or in which introns have been shortened or lengthened. Such variants will be ones in which the biological activity of the protein is substantially retained, this may be achieved by selectively retaining functional segments of the protein. Such splice variants may be found in nature or may be manmade. Methods for making such splice variants are known in the art. Preferred splice variants are splice variants of the nucleic acid encoding a polypeptide comprising the Ste20 signature sequence (SEQ ID NO: 6) and a N-terminal Ser/Thr kinase domain as defined above. Preferably, the Ste20-like polypeptide or a homologue thereof additionally comprises SEQ ID NO: 7, more preferably the Ste20-like polypeptide or a homologue thereof comprises one or more of the following: SEQ ID NO: 8, SEQ ID NO: 9 and SEQ ID NO: 10. Further preferred are splice variants of nucleic acids represented by SEQ ID NO: 1, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33. Most preferred is a splice variant of the nucleic acid represented by SEQ ID NO: 1.

Another nucleic acid variant useful in the methods of the invention is an allelic variant of a nucleic acid encoding a Ste20-like polypeptide or a homologue thereof as defined above, preferably an allelic variant of a nucleic acid encoding a Ste20-like polypeptide comprising the Ste20 signature sequence (SEQ ID NO: 6) and a N-terminal Ser/Thr kinase domain. Preferably, the Ste20-like polypeptide or a homologue thereof additionally comprises SEQ ID NO: 7, more preferably the Ste20-like polypeptide or a homologue thereof comprises one or more of the following: SEQ ID NO: 8, SEQ ID NO: 9 and SEQ ID NO: 10. Further preferred are allelic variants of nucleic acids represented by SEQ ID NO: 1, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33. Most preferred is an allelic variant of a nucleic acid as represented by SEQ ID NO: 1. Allelic variants exist in nature, and encompassed within the methods of the present invention is the use of these natural alleles. Allelic variants encompass Single Nucleotide Polymorphisms (SNPs), as well as Small Insertion/Deletion Polymorphisms (INDELs). The size of INDELs is usually less than 100 bp. SNPs and INDELs form the largest set of sequence variants in naturally occurring polymorphic strains of most organisms.

A further nucleic acid variant useful in the methods of the invention is a nucleic acid variant obtained by gene shuffling. Gene shuffling or directed evolution may also be used to generate variants of Ste20-like nucleic acids. This consists of iterations of DNA shuffling followed by appropriate screening and/or selection to generate variants of Ste20-like nucleic acids or portions thereof having a modified biological activity (Castle et al., (2004) Science 304(5674): 1151-4; U.S. Pat. Nos. 5,811,238 and 6,395,547).

Furthermore, site-directed mutagenesis may be used to generate variants of Ste20-like nucleic acids. Several methods are available to achieve site-directed mutagenesis; the most common being PCR based methods (Current Protocols in Molecular Biology. Wiley Eds.).

The Ste20-like nucleic acid or variant thereof may be derived from any natural or artificial source. The nucleic acid/gene or variant thereof may be isolated from a microbial source, such as yeast or fungi, or from a plant, algae or animal (including human) source. This nucleic acid may be modified from its native form in composition and/or genomic environment through deliberate human manipulation. The nucleic acid is preferably of plant origin, whether from the same plant species (for example to the one in which it is to be introduced) or whether from a different plant species. The nucleic acid may be isolated from a dicotyledonous species, preferably from the family Brassicaceae, further preferably from *Arabidopsis thaliana*. More preferably, the Ste20-like nucleic acid is isolated from *Arabidopsis thaliana* and is represented by SEQ ID NO: 1, and the Ste20-like amino acid sequences is as represented by SEQ ID NO: 2.

According to a preferred aspect of the present invention, modulated, preferably increased expression of the Ste20-like nucleic acid or variant thereof is envisaged. Methods for increasing expression of genes or gene products are well documented in the art and include, for example, overexpression driven by appropriate promoters, the use of transcription enhancers or translation enhancers. Isolated nucleic acids which serve as promoter or enhancer elements may be introduced in an appropriate position (typically upstream) of a non-heterologous form of a polynucleotide so as to upregulate expression of a Ste20-like nucleic acid or variant thereof. For example, endogenous promoters may be altered in vivo by mutation, deletion, and/or substitution (see, Kmiec, U.S. Pat. No. 5,565,350; Zarling et al., PCT/US93/03868), or isolated promoters may be introduced into a plant cell in the proper orientation and distance from a gene of the present invention so as to control the expression of the gene. Methods for reducing the expression of genes or gene products are well documented in the art.

The expression of a nucleic acid encoding a Ste20-like polypeptide or a homologue thereof may be modulated by introducing a genetic modification (preferably in the locus of a Ste20-like gene). The locus of a gene as defined herein is taken to mean a genomic region, which includes the gene of interest and 10 kb up- or down stream of the coding region.

The genetic modification may be introduced by, for example, T-DNA activation, TILLING, or homologous recombination. Following introduction of the genetic modification, there follows a step of selecting for modified expression of a nucleic acid encoding a Ste20-like polypeptide or a homologue thereof, which modification in expression gives plants having increased yield.

T-DNA activation tagging (Hayashi et al. Science (1992) 1350-1353) involves insertion of T-DNA, usually containing a promoter (may also be a translation enhancer or an intron), in the genomic region of the gene of interest or 10 kb up- or down stream of the coding region of a gene in a configuration such that the promoter directs expression of the targeted gene. Typically, regulation of expression of the targeted gene by its natural promoter is disrupted and the gene falls under the control of the newly introduced promoter. The promoter is typically embedded in a T-DNA. This T-DNA is randomly inserted into the plant genome, for example, through *Agrobactedum* infection and leads to overexpression of genes near the inserted T-DNA. The resulting transgenic plants show dominant phenotypes due to overexpression of genes close to the introduced promoter. The promoter to be introduced may be any promoter capable of directing expression of a gene in the desired organism, in this case a plant. For example, constitutive, tissue-preferred, cell type-preferred and inducible promoters are all suitable for use in T-DNA activation.

A genetic modification may also be introduced in the locus of a Ste20-like gene using the technique of TILLING (Targeted Induced Local Lesions In Genomes). This is a mutagenesis technology useful to generate and/or identify (and to eventually isolate) mutagenised variants of a Ste20-like nucleic acid with modulated expression and/or activity. TILLING also allows selection of plants carrying such mutant variants. These mutant variants may exhibit modified expression, either in strength or in location or in timing (if the mutations affect the promoter for example). These mutant variants may even exhibit higher Ste20-like activity than that exhibited by the gene in its natural form. TILLING combines high-density mutagenesis with high-throughput screening methods. The steps typically followed in TILLING are: (a) EMS mutagenesis (Redei G P and Koncz C (1992) In Methods in *Arabidopsis* Research, Koncz C, Chua N H, Schell J, eds. Singapore, World Scientific Publishing Co, pp. 1682; Feldmann et al., (1994) In Meyerowitz E M, Somerville C R, eds, *Arabidopsis*. Cold Spring Harbor Laboratory Press, Cold Spring Harbor, N.Y., pp 137-172; Lightner J and Caspar T (1998) In J Martinez-Zapater, J Salinas, eds, Methods on Molecular Biology, Vol. 82. Humana Press, Totowa, N.J., pp 91-104); (b) DNA preparation and pooling of individuals; (c) PCR amplification of a region of interest; (d) denaturation and annealing to allow formation of heteroduplexes; (a) DHPLC, where the presence of a heteroduplex in a pool is detected as an extra peak in the chromatogram; (f) identification of the mutant individual; and (g) sequencing of the mutant PCR product. Methods for TILLING are well known in the art (McCallum et al., (2000) Nat Biotechnol 18: 455-457; reviewed by Stemple (2004) Nat Rev Genet 5(2): 145-50).

T-DNA activation and TILLING are examples of technologies that enable the generation of novel alleles and Ste20-like variants.

The effects of the invention may also be reproduced using homologous recombination, which allows introduction in a genome of a selected nucleic acid at a defined selected position. Homologous recombination is a standard technology used routinely in biological sciences for lower organisms such as yeast or the moss *Physcomitrella*. Methods for performing homologous recombination in plants have been described not only for model plants (Offring a et al. (1990) EMBO J 9(10): 3077-84) but also for crop plants, for example rice (Terada et al. (2002) Nat Biotech 20(10): 1030-4; Iida and Terada (2004) Curr Opin Biotech 15(2):132-8). The nucleic acid to be targeted (which may be a Ste20-like nucleic acid or variant thereof as hereinbefore defined) need not be targeted to the locus of a Ste20-like gene, but may be introduced in, for example, regions of high expression. The nucleic acid to be targeted may be an improved allele used to replace the endogenous gene or may be introduced in addition to the endogenous gene.

A preferred method for introducing a genetic modification (which in this case need not be in the locus of a Ste20-like gene) is to introduce and express in a plant a nucleic acid encoding a Ste20-like polypeptide or a homologue thereof, as defined above. The nucleic acid to be introduced into a plant may be a full-length nucleic acid or may be a portion or a hybridising sequence as hereinbefore defined.

The invention also provides genetic constructs and vectors to facilitate introduction and/or expression of the nucleotide sequences useful in the methods according to the invention.

Therefore, there is provided a gene construct comprising:
(i) a Ste20-like nucleic acid or variant thereof, as defined hereinabove;
(ii) one or more control sequences capable of driving expression of the nucleic acid sequence of (i); and optionally
(iii) a transcription termination sequence.

Constructs useful in the methods according to the present invention may be constructed using recombinant DNA technology well known to persons skilled in the art. The gene constructs may be inserted into vectors, which may be commercially available, suitable for transforming into plants and suitable for expression of the gene of interest in the transformed cells.

Plants are transformed with a vector comprising the sequence of interest (i.e., a nucleic acid encoding a Ste20-like polypeptide or homologue thereof). The skilled artisan is well aware of the genetic elements that must be present on the vector in order to successfully transform, select and propagate host cells containing the sequence of interest. The sequence of interest is operably linked to one or more control sequences (at least to a promoter). The terms "regulatory element", "control sequence" and "promoter" are all used interchangeably herein and are to be taken in a broad context to refer to regulatory nucleic acid sequences capable of effecting expression of the sequences to which they are ligated. The term "promoter" typically refers to a nucleic acid control sequence located upstream from the transcriptional start of a gene and which is involved in recognising and binding of RNA polymerase and other proteins, thereby directing transcription of an operably linked nucleic add. Encompassed by the aforementioned terms are transcriptional regulatory sequences derived from a classical eukaryotic genomic gene (including the TATA box which is required for accurate transcription initiation, with or without a CCAAT box sequence) and additional regulatory elements (i.e. upstream activating sequences, enhancers and silencers) which alter gene expression in response to developmental and/or external stimuli, or in a tissue-specific manner. Also included within the term is a transcriptional regulatory sequence of a classical prokaryotic gene, in which case it may include a −35 box sequence and/or −10 box transcriptional regulatory sequences. The term "regulatory element" also encompasses a synthetic fusion molecule or derivative that confers, activates or enhances expression of a nucleic acid molecule in a cell, tissue or organ. The term "operably linked" as used herein refers to a functional linkage between the promoter sequence and the gene of interest, such that the promoter sequence is able to initiate transcription of the gene of interest.

Suitable promoters, which are functional in plants, are generally known. They may take the form of constitutive or inducible promoters. Suitable promoters can enable the development- and/or tissue-specific expression in multicelled eukaryotes; thus, leaf-, root-, flower-, seed-, stomata-, tuber- or fruit-specific promoters may advantageously be used in plants.

Different plant promoters usable in plants are promoters such as, for example, the USP, the LegB4-, the DC3 promoter or the ubiquitin promoter from parsley.

A "plant" promoter comprises regulatory elements, which mediate the expression of a coding sequence segment in plant cells. Accordingly, a plant promoter need not be of plant origin, but may originate from viruses or microorganisms, in particular for example from viruses which attack plant cells.

The "plant" promoter can also originates from a plant cell, e.g. from the plant, which is transformed with the nucleic acid sequence to be expressed in the inventive process and described herein. This also applies to other "plant" regulatory signals, for example in "plant" terminators.

For expression in plants, the nucleic acid molecule must, as described above, be linked operably to or comprise a suitable promoter which expresses the gene at the right point in time and in a cell- or tissue-specific manner. Usable promoters are constitutive promoters (Benfey et al., EMBO J. 8 (1989) 2195-2202), such as those which originate from plant viruses, such as 35S CAMV (Franck et al., Cell 21 (1980) 285-294), 19S CaMV (see also U.S. Pat. No. 5,352,605 and WO 84/02913), 34S FMV (Sanger et al., Plant. Mol. Biol., 14, 1990: 433%), the parsley ubiquitin promoter, or plant promoters such as the Rubisco small subunit promoter described in U.S. Pat. No. 4,962,028 or the plant promoters PRP1 [Ward et al., Plant. Mol. Biol. 22 (1993)], SSU, PGEL1, OCS [Leisner (1988) Proc Natl Acad Sci USA 85(5): 2553-2557], lib4, usp, mas [Comai (1990) Plant Mol Biol 15 (3):373-381], STLS1, ScBV (Schenk (1999) Plant Mol Biol 39(6):1221-1230), B33, SAD1 or SAD2 (flax promoters, Jain et al., Crop Science, 39 (6), 1999: 1696-1701) or nos [Shaw et al. (1984) Nucleic Acids Res. 12(20):7831-7846]. Further examples of constitutive plant promoters are the sugarbeet V-ATPase promoters (WO 01/14572). Examples of synthetic constitutive promoters are the Super promoter (WO 95/14098) and promoters derived from G-boxes (WO 94/12015). If appropriate, chemical inducible promoters may furthermore also be used, compare EP-A 388186, EP-A 335528, WO 97/06268. Stable, constitutive expression of the proteins according to the invention a plant can be advantageous. However, inducible expression of the polypeptide of the invention is advantageous, if a late expression before the harvest is of advantage, as metabolic manipulation may lead to plant growth retardation.

The expression of plant genes can also be facilitated via a chemical inducible promoter (for a review, see Gatz 1997, Annu. Rev. Plant Physiol. Plant Mol. Biol., 48:89-108). Chemically inducible promoters are particularly suitable when it is desired to express the gene in a time-specific manner. Examples of such promoters are a salicylic acid inducible promoter (WO 95/19443), and abscisic acid-inducible promoter (EP 335 528), a tetracydin-inducible promoter (Gatz et al. (1992) Plant J. 2, 397-404), a cyclohexanol- or ethanol-inducible promoter (WO 93/21334) or others as described herein.

Other suitable promoters are those which react to biotic or abiotic stress conditions, for example the pathogen-induced PRP1 gene promoter (Ward et al., Plant. Mol. Biol. 22 (1993) 361-366), the tomato heat-inducible hsp80 promoter (U.S. Pat. No. 5,187,267), the potato chill-inducible alpha-amylase promoter (WO 96/12814) or the wound-inducible pinII promoter (EP-A0 375 091) or others as described herein.

Preferred promoters are in particular those which bring gene expression in tissues and organs, in seed cells, such as endosperm cells and cells of the developing embryo. Suitable promoters are the oilseed rape napin gene promoter (U.S. Pat. No. 5,608,152), the *Vicia faba* USP promoter (Baeumlein et al., Mol Gen Genet, 1991, 225 (3): 459-67), the *Arabidopsis* oleosin promoter (WO 98/45461), the Phaseolus vulgaris phaseolin promoter (U.S. Pat. No. 5,504,200), the Brassica Bce4 promoter (WO 91/13980), the bean arc5 promoter, the carrot DcG3 promoter, or the Legumin B4 promoter (LeB4; Baeumlein et al., 1992, Plant Journal, 2 (2): 233-9), and promoters which bring about the seed-specific expression in monocotyledonous plants such as maize, barley, wheat, rye, rice and the like. Advantageous seed-specific promoters are the sucrose binding protein promoter (WO 00/26388), the phaseolin promoter and the napin promoter. Suitable promoters which must be considered are the barley Ipt2 or Ipt1 gene promoter (WO 95/15389 and WO 95/23230), and the promoters described in WO 99/16890 (promoters from the barley hordein gene, the rice glutelin gene, the rice oryzin gene, the rice prolamin gene, the wheat gliadin gene, the wheat glutelin gene, the maize zein gene, the oat glutelin gene, the sorghum kasirin gene and the rye secalin gene). Further suitable promoters are Amy32b, Amy 6-6 and Aleurain [U.S. Pat. No. 5,677,474], Bce4 (oilseed rape) [U.S. Pat. No. 5,530,149], glycinin (soya) [EP 571 741], phosphoenolpyruvate carboxylase (soya) [JP 06/62870], ADR12-2 (soya) [WO 98/08962], isocitrate lyase (oilseed rape) [U.S. Pat. No. 5,689,040] or α-amylase (barley) [EP 781 849]. Other promoters which are available for the expression of genes in plants are leaf-specific promoters such as those described in DE-A 19644478 or light-regulated promoters such as, for example, the pea petE promoter.

Further suitable plant promoters are the cytosolic FBPase promoter or the potato ST-LSI promoter (Stockhaus et al., EMBO J. 8, 1989, 2445), the *Glycine max* phosphoribosylpyrophosphate amidotransferase promoter (GenBank Accession No. U87999) or the node-specific promoter described in EP-A-0 249 676.

Advantageously, any type of promoter may be used to drive expression of the nucleic acid sequence. The promoter may be an inducible promoter, i.e. having induced or increased transcription initiation in response to a chemical, environmental or physical stimulus. An example of an inducible promoter is a stress-inducible promoter, i.e. a promoter activated when a plant is exposed to various stress conditions, or a pathogen-induced promoter. Additionally or alternatively, the promoter may be a tissue-preferred promoter, i.e. one that is capable of preferentially initiating transcription in certain tissues, such as the leaves, roots, seed tissue etc; or may be a ubiquitous promoter, which is active in substantially all tissues or cells of an organism, or the promoter may be developmentally regulated, thereby being active during certain developmental stages or in parts of the plant that undergo developmental changes. Promoters able to initiate transcription in certain tissues only are referred to herein as "tissue-specific", similarly, promoters able to initiate transcription in certain cells only are referred to herein as "cell-specific".

Preferably, the Ste20-like nucleic acid or variant thereof is operably linked to a constitutive promoter. A constitutive promoter is transcriptionally active during most, but not necessarily all, phases of its growth and development and under most environmental conditions in at least one cell, tissue or organ. A preferred constitutive promoter is a constitutive promoter that is also substantially ubiquitously expressed. Further preferably the promoter is derived from a plant, more preferably a monocotyledonous plant. Most preferred is use of a GOS2 promoter (from rice) (as used in the expression cassette of SEQ ID NO: 5). It should be clear that the applicability of the present invention is not restricted to the Ste20-like nucleic acid represented by SEQ ID NO: 1, nor is the applicability of the invention restricted to expression of a nucleic acid encoding a Ste20-like protein when driven by a GOS2 promoter. Examples of other constitutive promoters which may also be used to drive expression of a nucleic acid encoding a Ste20-like protein are shown in Table 2 below.

TABLE 2

Examples of constitutive promoters

| Gene Source | Expression Pattern | Reference |
|---|---|---|
| Actin | Constitutive | McElroy et al, Plant Cell, 2: 163-171, 1990 |
| CAMV 35S | Constitutive | Odell et al, Nature, 313: 810-812, 1985 |
| CaMV 19S | Constitutive | Nilsson et al., Physiol. Plant 100: 456-462, 1997 |
| GOS2 | Constitutive | de Pater et al, Plant J Nov; 2(6): 837-44, 1992 |
| Ubiquitin | Constitutive | Christensen et al, Plant Mol. Biol. 18: 675-689, 1992 |
| Rice cyclophilin | Constitutive | Buchholz et al, Plant Mol Biol. 25(5): 837-43, 1994 |
| Maize H3 histone | Constitutive | Lepetit et al, Mol. Gen. Genet. 231: 276-285, 1992 |
| Actin 2 | Constitutive | An et al, Plant J. 10(1); 107-121, 1996 |

Optionally, one or more terminator sequences (also a control sequence) may be used in the construct introduced into a plant. The term "terminator" encompasses a control sequence which is a DNA sequence at the end of a transcriptional unit which signals 3' processing and polyadenylation of a primary transcript and termination of transcription. The terminator can be derived from the natural gene, from a variety of other plant genes, or from T-DNA. The terminator to be added may be derived from, for example, the nopaline synthase or octopine synthase genes, or alternatively from another plant gene, less preferably from any other eukaryotic gene. Additional regulatory elements may include transcriptional as well as translational enhancers. Those skilled in the art will be aware of terminator and enhancer sequences that may be suitable for use in performing the invention. Such sequences would be known or may readily be obtained by a person skilled in the art.

An intron sequence may also be added to the 5' untranslated region or the coding sequence of the partial coding sequence to increase the amount of the mature message that accumulates in the cytosol. Inclusion of a spliceable intron in the transcription unit in both plant and animal expression constructs has been shown to increase gene expression at both the mRNA and protein levels up to 1000-fold, Buchman and Berg, Mol. Cell biol. 8:4395-4405 (1988); Callis et al., Genes Dev. 1:1183-1200 (1987). Such intron enhancement of gene expression is typically greatest when placed near the 5' end of the transcription unit. Use of the maize introns Adh1-S intron 1, 2, and 6, the Bronze-1 intron are known in the art. See generally, The Maize Handbook, Chapter 116, Freeling and Walbot, Eds., Springer, N.Y. (1994).

Other control sequences (besides promoter, enhancer, silencer, intron sequences, 3'UTR and/or 5'UTR regions) may be protein and/or RNA stabilizing elements. Such sequences would be known or may readily be obtained by a person skilled in the art.

The genetic constructs of the invention may further include an origin of replication sequence that is required for maintenance and/or replication in a specific cell type. One example is when a genetic construct is required to be maintained in a bacterial cell as an episomal genetic element (e.g. plasmid or cosmid molecule). Preferred origins of replication include, but are not limited to, the f1-ori and colE1.

For the detection and/or selection of the successful transfer of the nucleic acid sequences as depicted in the sequence protocol and used in the process of the invention, it is advantageous to use marker genes (=reporter genes). These marker genes enable the identification of a successful transfer of the nucleic acid molecules via a series of different principles, for example via visual identification with the aid of fluorescence, luminescence or in the wavelength range of light which is discernible for the human eye, by a resistance to herbicides or antibiotics, via what are known as nutritive markers (auxotrophism markers) or antinutritive markers, via enzyme assays or via phytohormones. Examples of such markers which may be mentioned are GFP (=green fluorescent protein); the luciferin/luceferase system, the β-galactosidase with its colored substrates, for example X-Gal, the herbicide resistances to, for example, imidazolinone, glyphosate, phosphinothricin or sulfonylurea, the antibiotic resistances to, for example, bleomycin, hygromycin, streptomycin, kanamycin, tetracyclin, chloramphenicol, ampicillin, gentamycin, geneticin (G418), spectinomycin or blasticidin, to mention only a few, nutritive markers such as the utilization of mannose or xylose, or antinutritive markers such as the resistance to 2-deoxyglucose. This list is a small number of possible markers. The skilled worker is very familiar with such markers. Different markers are preferred, depending on the organism and the selection method.

Therefore the genetic construct may optionally comprise a selectable marker gene. As used herein, the term "selectable marker" or "selectable marker gene" includes any gene that confers a phenotype on a cell in which it is expressed to facilitate the identification and/or selection of cells that are transfected or transformed with a nucleic add construct of the invention. Suitable markers may be selected from markers that confer antibiotic or herbicide resistance, that introduce a new metabolic trait or that allow visual selection. Examples of selectable marker genes include genes conferring resistance to antibiotics (such as nptII that phosphorylates neomycin and kanamycin, or hpt, phosphorylating hygromycin), to herbicides (for example bar which provides resistance to Basta; aroA or gox providing resistance against glyphosate), or genes that provide a metabolic trait (such as mana that allows plants to use mannose as sole carbon source). Visual marker genes result in the formation of colour (for example β-glucuronidase, GUS), luminescence (such as luciferase) or fluorescence (Green Fluorescent Protein, GFP, and derivatives thereof).

It is known of the stable or transient integration of nucleic acids into plant cells that only a minority of the cells takes up the foreign DNA and, if desired, integrates it into its genome, depending on the expression vector used and the transfection technique used. To identify and select these integrants, a gene encoding for a selectable marker (as described above, for example resistance to antibiotics) is usually introduced into the host cells together with the gene of interest. Preferred selectable markers in plants comprise those, which confer resistance to an herbicide such as glyphosate or gluphosinate. Other suitable markers are, for example, markers, which encode genes involved in biosynthetic pathways of, for example, sugars or amino acids, such as β-galactosidase, ura3 or ilv2. Markers, which encode genes such as luciferase, gfp or other fluorescence genes, are likewise suitable. These markers and the aforementioned markers can be used in mutants in whom these genes are not functional since, for example, they have been deleted by conventional methods. Furthermore, nucleic acid molecules, which encode a selectable marker, can be introduced into a host cell on the same vector as those, which encode the polypeptides of the invention or used in the process or else in a separate vector. Cells which have been transfected stably with the nucleic acid introduced can be identified for example by selection (for example, cells which have integrated the selectable marker survive whereas the other cells die).

Since the marker genes, as a rule specifically the gene for resistance to antibiotics and herbicides, are no longer required or are undesired in the transgenic host cell once the nucleic acids have been introduced successfully, the process according to the invention for introducing the nucleic acids advantageously employs techniques which enable the removal, or excision, of these marker genes. One such a method is what is known as cotransformation. The cotransformation method employs two vectors simultaneously for the transformation, one vector bearing the nucleic acid according to the invention and a second bearing the marker gene(s). A large proportion of transformants receives or, in the case of plants, comprises (up to 40% of the transformants and above), both vectors. In case of transformation with *Agrobacteria*, the transformants usually receive only a part of the vector, the sequence flanked by the T-DNA, which usually represents the expression cassette. The marker genes can subsequently be removed from the transformed plant by performing crosses. In another method, marker genes integrated into a transposon are used for the transformation together with desired nucleic acid (known as the Ac/Ds technology). The transformants can be crossed with a transposase resource or the transformants are transformed with a nucleic acid construct conferring expression of a transposase, transiently or stable. In some cases (approx. 10%), the transposon jumps out of the genome of the host cell once transformation has taken place successfully and is lost. In a further number of cases, the transposon jumps to a different location. In these cases, the marker gene must be eliminated by performing crosses. In microbiology, techniques were developed which make possible, or facilitate, the detection of such events. A further advantageous method relies on what are known as recombination systems; whose advantage is that elimination by crossing can be dispensed with. The best-known system of this type is what is known as the Cre/lox system. Cre1 is a recombinase, which removes the sequences located between the loxP sequences. If the marker gene is integrated between the loxP sequences, it is removed, once transformation has taken place successfully, by expression of the recombinase. Further recombination systems are the HIN/HIX, FLP/FRT and REP/STB system (Tribble et al., J. Biol. Chem., 275, 2000: 22255-22267; Velmurugan et al., J. Cell Biol., 149, 2000: 553-566). A site-specific integration into the plant genome of the nucleic acid sequences according to the invention is possible. Naturally, these methods can also be applied to microorganisms such as yeast, fungi or bacteria.

The present invention also encompasses plants obtainable by the methods according to the present invention. The present invention therefore provides plants obtainable by the method according to the present invention, which plants have introduced therein a Ste20-like nucleic acid or variant thereof.

The invention also provides a method for the production of transgenic plants having increased yield, comprising introduction and expression in a plant of a Ste20-like nucleic acid or a variant thereof as defined above.

For the purposes of the invention, "transgenic", "transgene" or "recombinant" means with regard to, for example, a nucleic acid sequence, an expression cassette (=gene construct) or a vector comprising the nucleic acid sequence or an organism transformed with the nucleic acid sequences, expression cassettes or vectors according to the invention, all those constructions brought about by recombinant methods in which either
a) the nucleic acid sequences according to the invention, or
b) genetic control sequences which is operably linked with the nucleic acid sequence according to the invention, for example a promoter, or
c) a) and b)

are not located in their natural genetic environment or have been modified by recombinant methods, it being possible for the modification to take the form of, for example, a substitution, addition, deletion, inversion or insertion of one or more nucleotide residues. The natural genetic environment is understood as meaning the natural genomic or chromosomal locus in the original plant or the presence in a genomic library. In the case of a genomic library, the natural genetic environment of the nucleic acid sequence is preferably retained, at least in part. The environment flanks the nucleic acid sequence at least on one side and has a sequence length of at least 50 bp, preferably at least 500 bp, especially preferably at least 1000 bp, most preferably at least 5000 bp. A naturally occurring expression cassette—for example the naturally occurring combination of the natural promoter. of the nucleic acid sequences with the corresponding nucleic acid sequence encoding a polypeptide having kinase domains or a homologue of such polypeptide—becomes a transgenic expression cassette when this expression cassette is modified by non-natural, synthetic ("artificial") methods such as, for example, mutagenic treatment. Suitable methods are described, for example, in U.S. Pat. No. 5,565,350 or WO 00/15815.

A transgenic plant for the purposes of the invention is therefore understood as meaning, as above, that the nucleic acids used in the method of the invention are not at their natural locus in the genome of said plant, it being possible for the nucleic acids to be expressed homologously or heterologously. However, as mentioned, transgenic also means that, while the nucleic adds according to the invention or used in the inventive method are at their natural position in the genome of a plant, the sequence has been modified with regard to the natural sequence, and/or that the regulatory sequences of the natural sequences have been modified. Transgenic is preferably understood as meaning the expression of the nucleic acids according to the invention at an unnatural locus in the genome, i.e. homologous or, preferably, heterologous expression of the nucleic acids takes place. Preferred transgenic plants are mentioned herein.

Host plants for the nucleic acids or the vector used in the method according to the invention, the expression cassette or construct or vector are, in principle, advantageously all plants, which are capable of synthesizing the polypeptides used in the inventive method.

More specifically, the present invention provides a method for the production of transgenic plants having increased yield, which method comprises:
(i) introducing and expressing in a plant cell a Ste20-like nucleic acid or variant thereof; and
(ii) cultivating the plant cell under conditions promoting plant growth and development.

The nucleic acid may be introduced directly into a plant cell or into the plant itself (including introduction into a tissue, organ or any other part of a plant). According to a preferred feature of the present invention, the nucleic acid is preferably introduced into a plant by transformation.

The term "introduction" or "transformation" as referred to herein encompasses the transfer of an exogenous polynucleotide into a host cell, irrespective of the method used for transfer. Plant tissue capable of subsequent clonal propagation, whether by organogenesis or embryogenesis, may be transformed with a genetic construct of the present invention and a whole plant regenerated there from. The particular tissue chosen will vary depending on the clonal propagation systems available for, and best suited to, the particular species being transformed. Exemplary tissue targets include leaf disks, pollen, embryos, cotyledons, hypocotyls, megagametophytes, callus tissue, existing meristematic tissue (e.g., apical meristem, axillary buds, and root meristems), and induced meristem tissue (e.g., cotyledon meristem and hypocotyl meristem). The polynucleotide may be transiently or stably introduced into a host cell and may be maintained non-integrated, for example, as a plasmid. Alternatively, it may be integrated into the host genome. The resulting transformed plant cell may then be used to regenerate a transformed plant in a manner known to persons skilled in the art.

The transfer of foreign genes into the genome of a plant is called transformation. In doing this the methods described for the transformation and regeneration of plants from plant tissues or plant cells are utilized for transient or stable transformation. An advantageous transformation method is the transformation in planta. To this end, it is possible, for example, to allow the agrobacteria to act on plant seeds or to inoculate the plant meristem with agrobacteria. It has proved particularly expedient in accordance with the invention to allow a suspension of transformed agrobacteria to act on the intact plant or at least the flower primordia. The plant is subsequently grown on until the seeds of the treated plant are obtained (Clough and Bent, Plant J. (1998) 16, 735-743). To select transformed plants, the plant material obtained in the transformation is, as a rule, subjected to selective conditions so that transformed plants can be distinguished from untransformed plants. For example, the seeds obtained in the above-described manner can be planted and, after an initial growing period, subjected to a suitable selection by spraying. A further possibility consists in growing the seeds, if appropriate after sterilization, on agar plates using a suitable selection agent so that only the transformed seeds can grow into plants. Further advantageous transformation methods, in particular for plants, are known to the skilled worker and are described herein below.

Transformation of plant species is now a fairly routine technique. Advantageously, any of several transformation methods may be used to introduce the gene of interest into a suitable ancestor cell. Transformation methods include the use of liposomes, electroporation, chemicals that increase free DNA uptake, injection of the DNA directly into the plant, particle gun bombardment, transformation using viruses or pollen and microprojection. Methods may be selected from the calcium/polyethylene glycol method for protoplasts (Krens, F. A. et al., (1982) Nature 296, 72-74; Negrutiu I et al. (1987) Plant Mol Biol 8: 363-373); electroporation of protoplasts (Shillito R. D. et al. (1985) Bio/Technol 3, 1099-1102); microinjection into plant material (Crossway A et al., (1986) Mol. Gen Genet 202: 179-185); DNA or RNA-coated particle bombardment (Klein T M et al., (1987) Nature 327: 70) infection with (non-integrative) viruses and the like. Transgenic rice plants expressing a Ste20-like nucleic acid/gene are preferably produced via *Agrobacterium*-mediated transformation using any of the well known methods for rice transformation, such as described in any of the following: published European patent application EP 1198985 A1, Aldemita and Hodges (Planta 199: 612-617, 1996); Chan et al. (Plant Mol Biol 22 (3): 491-506, 1993), Hiei et al. (Plant J 6 (2): 271-282, 1994), which disclosures are incorporated by reference herein as if fully set forth. In the case of corn transformation, the preferred method is as described in either Ishida et al. (Nat. Biotechnol 14(6): 745-50, 1996) or Frame et al. (Plant Physiol 129(1): 13-22, 2002), which disclosures are incorporated by reference herein as if fully set forth. Said methods are further described by way of example in B. Jenes et al., Techniques for Gene Transfer, in: Transgenic Plants, Vol. 1, Engineering and Utilization, eds. S. D. Kung and R. Wu, Academic Press (1993) 128-143 and in Potrykus Annu. Rev. Plant Physiol. Plant Molec. Biol. 42 (1991) 205-225). The nucleic acids or the construct to be expressed is preferably cloned into a vector, which is suitable for transforming *Agrobacterium tumefaciens*, for example pBin19 (Bevan et al., Nucl. Acids Res. 12 (1984) 8711). *Agrobacteria* transformed by such a vector can then be used in known manner for the transformation of plants, in particular of crop plants such as by way of example tobacco plants, for example by bathing bruised leaves or chopped leaves in an agrobacterial solution and then culturing them in suitable media. The transformation of plants by means of *Agrobacterium* tumefaciens is described, for example, by Höfgen and Willmitzer in Nucl. Acid Res. (1988) 16, 9877 or is known inter alia from F. F. White, Vectors for Gene Transfer in Higher Plants; in Transgenic Plants, Vol. 1, Engineering and Utilization, eds. S. D. Kung and R. Wu, Academic Press, 1993, pp. 15-38.

Generally after transformation, plant cells or cell groupings are selected for the presence of one or more markers which are encoded by plant-expressible genes co-transferred with the gene of interest, following which the transformed material is regenerated into a whole plant.

As mentioned *Agrobacteria* transformed with an expression vector according to the invention may also be used in the manner known per se for the transformation of plants such as experimental plants like *Arabidopsis* or crop plants, such as, for example, cereals, maize, oats, rye, barley, wheat, soya, rice, cotton, sugarbeet, canola, sunflower, flax, hemp, potato, tobacco, tomato, carrot, bell peppers, oilseed rape, tapioca, cassava, arrow root, tagetes, alfalfa, lettuce and the various tree, nut, and grapevine species, in particular oil-containing crop plants such as soya, peanut, castor-oil plant, sunflower, maize, cotton, flax, oilseed rape, coconut, oil palm, safflower (*Carthamus tinctorius*) or cocoa beans, for example by bathing scarified leaves or leaf segments in an agrobacterial solution and subsequently growing them in suitable media.

In addition to the transformation of somatic cells, which then has to be regenerated into intact plants, it is also possible to transform the cells of plant meristems and in particular those cells which develop into gametes. In this case, the transformed gametes follow the natural plant development, giving rise to transgenic plants. Thus, for example, seeds of *Arabidopsis* are treated with agrobacteria and seeds are obtained from the developing plants of which a certain proportion is transformed and thus transgenic [Feldman, K A and Marks M D (1987). Mol Gen Genet 208:274-289; Feldmann K (1992). In: C Koncz, N-H Chua and J Shell, eds, Methods in *Arabidopsis* Research. Word Scientific, Singapore, pp. 274-289]. Alternative methods are based on the repeated removal of the influorescences and incubation of the excision site in the center of the rosette with transformed agrobacteria, whereby transformed seeds can likewise be obtained at a later point in time (Chang (1994). Plant J. 5: 551-558; Katavic (1994). Mol Gen Genet, 245: 363-370). However, an especially effective method is the vacuum infiltration method with its modifications such as the "floral dip" method. In the case of vacuum infiltration of *Arabidopsis*, intact plants under reduced pressure are treated with an agrobacterial suspension [Bechthold, N (1993). C R Acad Sci Paris Life Sci, 316: 1194-1199], while in the case of the "floral dip" method the developing floral tissue is incubated briefly with a surfactant-treated agrobacterial suspension [Clough, S J und Bent, A F (1998). The Plant J. 16, 735-743]. A certain proportion of transgenic seeds are harvested in both cases, and these seeds can be distinguished from nontransgenic seeds by growing under the above-described selective conditions. In addition the stable transformation of plastids is of advantages because plastids are inherited maternally is most crops reducing or eliminating the risk of transgene flow through pollen. The transformation of the chloroplast genome is generally achieved by a process, which has been schematically displayed in Klaus et al., 2004 [Nature Biotechnology 22 (2), 225-229]. Briefly the sequences to be transformed are cloned together with a selectable marker gene between flanking sequences homologous to the chloroplast genome. These homologous flanking sequences direct site specific integration into the plastome. Plastidal transformation has been described for many different plant species and an overview can be taken from Bock (2001) Transgenic plastids in basic research and plant biotechnology. J Mol Biol. 2001 Sep. 21; 312 (3):425-38 or Maliga, P (2003) Progress towards commercialization of plastid transformation technology. Trends Biotechnol. 21, 20-28. Further biotechnological progress has recently been reported in form of marker free plastid transformants, which can be produced by a transient cointegrated maker gene (Klaus et al., 2004, Nature Biotechnology 22(2), 225-229).

The genetically modified plant cells can be regenerated via all methods with which the skilled worker is familiar. Suitable methods can be found in the abovementioned publications by S. D. Kung and R. Wu, Potrykus or Höfgen and Willmitzer.

Following DNA transfer and regeneration, putatively transformed plants may be evaluated, for instance using Southern analysis, for the presence of the gene of interest, copy number and/or genomic organisation. Alternatively or additionally, expression levels of the newly introduced DNA may be monitored using Northern and/or Western analysis, or quantitiative PCR, all techniques being well known to persons having ordinary skill in the art.

The generated transformed plants may be propagated by a variety of means, such as by clonal propagation or classical breeding techniques. For example, a first generation (or T1) transformed plant may be selfed and homozygous second-generation (or T2) transformants selected, and the T2 plants may then further be propagated through classical breeding techniques.

The generated transformed organisms may take a variety of forms. For example, they may be chimeras of transformed cells and non-transformed cells; clonal transformants (e.g., all cells transformed to contain the expression cassette); grafts of transformed and untransformed tissues (e.g., in plants, a transformed rootstock grafted to an untransformed scion).

The present invention clearly extends to any plant cell or plant produced by any of the methods described herein, and to all plant parts and propagules thereof. The present invention extends further to encompass the progeny of a primary transformed or transfected cell, tissue, organ or whole plant that has been produced by any of the aforementioned methods, the only requirement being that progeny exhibit the same genotypic and/or phenotypic characteristic(s) as those produced by the parent in the methods according to the invention. The invention also includes host cells containing an isolated Ste20-like nucleic acid or variant thereof. Preferred host cells according to the invention are plant cells. The invention also extends to harvestable parts of a plant such as, but not limited to seeds, leaves, fruits, flowers, stems, rhizomes, tubers and bulbs. The invention furthermore relates to products directly derived from a harvestable part of such a plant, such as dry pellets or powders, oil, fat and fatty acids, starch or proteins.

The present invention also encompasses use of Ste20-like nucleic acids or variants thereof and use of Ste20-like polypeptides or homologues thereof.

One such use relates to improving the growth characteristics of plants, in particular in improving yield, especially seed yield. The seed yield may include one or more of the following: increased total weight of seeds, increased number of filled seeds and increased Harvest Index.

Ste20-like nucleic acids or variants thereof, or Ste20-like polypeptides or homologues thereof may find use in breeding programmes in which a DNA marker is identified which may be genetically linked to a Ste20-like gene or variant thereof. The Ste20-like nucleic acids/genes or variants thereof, or Ste20-like polypeptides or homologues thereof may be used to define a molecular marker. This DNA or protein marker may then be used in breeding programmes to select plants having increased yield. The Ste20-like gene or variant thereof may, for example, be a nucleic acid as represented by any one of SEQ ID NO: 1, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33.

Allelic variants of a Ste20-like nucleic acid/gene may also find use in marker-assisted breeding programmes. Such breeding programmes sometimes require introduction of allelic variation by mutagenic treatment of the plants, using for example EMS mutagenesis; alternatively, the programme may start with a collection of allelic variants of so called "natural" origin caused unintentionally. Identification of allelic variants then takes place, for example, by PCR. This is followed by a step for selection of superior allelic variants of the sequence in question and which give increased yield. Selection is typically carried out by monitoring growth performance of plants containing different allelic variants of the sequence in question, for example, different allelic variants of any one of SEQ ID NO: 1, SEQ ID NO: 11, SEQ ID NO: 13, SEQ ID NO: 15, SEQ ID NO: 17, SEQ ID NO: 19, SEQ ID NO: 21, SEQ ID NO: 23, SEQ ID NO: 25, SEQ ID NO: 27, SEQ ID NO: 29, SEQ ID NO: 31 and SEQ ID NO: 33. Growth performance may be monitored in a greenhouse or in the field. Further optional steps include crossing plants, in which the superior allelic variant was identified, with another plant. This could be used, for example, to make a combination of interesting phenotypic features.

A Ste20-like nucleic acid or variant thereof may also be used as probes for genetically and physically mapping the genes that they are a part of, and as markers for traits linked to those genes. Such information may be useful in plant breeding in order to develop lines with desired phenotypes. Such use of Ste20-like nucleic acids or variants thereof requires only a nucleic acid sequence of at least 15 nucleotides in length. The Ste20-like nucleic acids or variants thereof may be used as restriction fragment length polymorphism (RFLP) markers. Southern blots (Sambrook J, Fritsch E F and Maniatis T (1989) Molecular Cloning, A Laboratory Manual) of restriction-digested plant genomic DNA may be probed with the Ste20-like nucleic acids or variants thereof. The resulting banding patterns may then be subjected to genetic analyses using computer programs such as MapMaker (Lander et al. (1987) Genomics 1: 174-181) in order to construct a genetic map. In addition, the nucleic acids may be used to probe Southern blots containing restriction endonuclease-treated genomic DNAs of a set of individuals representing parent and progeny of a defined genetic cross. Segregation of the DNA polymorphisms is noted and used to calculate the position of the Ste20-like nucleic acid or variant thereof in the genetic map previously obtained using this population (Botstein et al. (1980) Am. J. Hum. Genet. 32:314-331).

The production and use of plant gene-derived probes for use in genetic mapping is described in Bernatzky and Tanksley (1986) Plant Mol. Biol. Reporter 4: 37-41. Numerous publications describe genetic mapping of specific cDNA clones using the methodology outlined above or variations thereof. For example, F2 intercross populations, backcross populations, randomly mated populations, near isogenic lines, and other sets of individuals may be used for mapping. Such methodologies are well known to those skilled in the art.

The nucleic acid probes may also be used for physical mapping (i.e., placement of sequences on physical maps; see Hoheisel et al. In: Non-mammalian Genomic Analysis: A Practical Guide, Academic press 1996, pp. 319-346, and references cited therein).

In another embodiment, the nucleic acid probes may be used in direct fluorescence in situ hybridization (FISH) mapping (Trask (1991) Trends Genet 7:149-154). Although current methods of FISH mapping favour use of large clones (several kb to several hundred kb; see Laan et al. (1995) Genome Res. 5:13-20), improvements in sensitivity may allow performance of FISH mapping using shorter probes.

A variety of nucleic acid amplification-based methods for genetic and physical mapping may be carried out using the nucleic acids. Examples include allele-specific amplification (Kazazian (1989) J. Lab. Clin. Med 11:95-96), polymorphism of PCR-amplified fragments (CAPS; Sheffield et al. (1993) Genomics 16:325-332), allele-specific ligation (Landegren et al. (1988) Science 241:1077-1080), nucleotide extension reactions (Sokolov (1990) Nucleic Acid Res. 18:3671), Radiation Hybrid Mapping (Walter et al. (1997) Nat. Genet. 7:22-28) and Happy Mapping (Dear and Cook (1989) Nucleic Acid Res. 17:6795-6807). For these methods, the sequence of a nucleic acid is used to design and produce primer pairs for use in the amplification reaction or in primer extension reactions. The design of such primers is well known to those skilled in the art. In methods employing PCR-based genetic mapping, it may be necessary to identify DNA sequence differences between the parents of the mapping cross in the region corresponding to the instant nucleic acid sequence. This, however, is generally not necessary for mapping methods.

The methods according to the present invention result in plants having increased yield, as described hereinbefore. These advantageous growth characteristics may also be combined with other economically advantageous traits, such as further yield-enhancing traits, tolerance to various stresses, traits modifying various architectural features and/or biochemical and/or physiological features.

DESCRIPTION OF FIGURES

The present invention will now be described with reference to the following figures in which:

FIG. 3 details examples of sequences useful in performing the methods according to the present invention.

EXAMPLES

Figure 1:
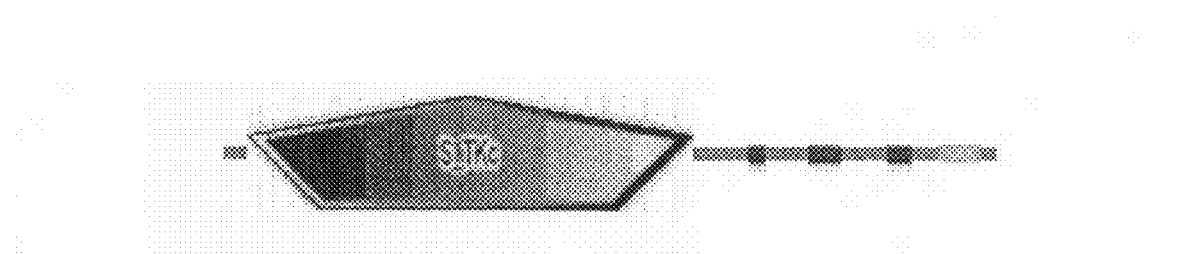
FIG. 1 shows the typical domain structure of Ste20-like polypeptides. The N-terminal end of the protein comprises a Ser/Thr kinase domain. The most C-terminal domain (in light grey) has a coiled coil structure, which is usually but not always present.

The present invention will now be described with reference to the following examples, which are by way of illustration alone. Unless otherwise stated, recombinant DNA techniques are performed according to standard protocols described in (Sambrook (2001) Molecular Cloning: a laboratory manual, 3rd Edition Cold Spring Harbor Laboratory Press, CSH, New York) or in Volumes 1 and 2 of Ausubel et al. (1994), Current Protocols in Molecular Biology, Current Protocols. Standard materials and methods for plant molecular work are described in Plant Molecular Biology Labfax (1993) by R. D. D. Croy, published by BIOS Scientific Publications Ltd (UK) and Blackwell Scientific Publications (UK).

Example 1

Identification of Homologues of the Ste20-Like Protein of SEQ ID NO: 2 and Determination of their Similarity/Identity Sequences (full length cDNA, ESTs or genomic) related to the nucleic acid sequence used in the methods of the present invention were identified amongst those maintained in the Entrez Nucleotides database at the National Center for Biotechnology Information using database sequence search tools, such as the Basic Local Alignment Tool (BLAST) (Altschul et al. (1990) J. Mol. Biol. 215:403-410; and Altschul et al. (1997) Nucleic Acids Res. 25:3389-3402). This program is typically used to find regions of local similarity between sequences by comparing nucleic acid or polypeptide sequences to sequence databases and by calculating the statistical significance of matches. The polypeptide encoded by the nucleic acid of the present invention was used with the TBLASTN algorithm, with default settings and the filter for ignoring low complexity sequences was set off. The output of the analysis was viewed by pairwise comparison, and ranked according to the probability score (E-value), where the score reflect the probability that a particular alignment occurs by chance (the lower the E-value, the more significant the hit). In addition to E-values, comparisons were also scored by percentage identity. Percentage identity refers to the number of identical nucleotides (or amino acids) between the two compared nucleic acid (or polypeptide) sequences over a particular length. In some instances, the default parameters may be adjusted to modify the stringency of the search.

Rice sequences and EST sequences from various plant species may also be obtained from other databases, such as KOME (Knowledge-based Oryza Molecular biological Encyclopedia; Kikuchi et al., Science 301, 376-379, 2003), Sputnik (Rudd, S., Nucleic Acids Res., 33: D622-D627, 2005) or the Eukaryotic Gene Orthologs database (EGO, hosted by The Institute for Genomic Research). These databases are searchable with the BLAST tool. SEQ ID NO: 11 to SEQ ID NO: 34 are nucleic acid and protein sequences of homologues of SEQ ID NO: 2 and were obtained from the above-mentioned databases using SEQ ID NO: 2 as a query sequence.

Percentages of similarity and identity between the full-length sequences and the sequences of the kinase domains of Ste20-like proteins were determined using MatGAT (Matrix Global Alignment Tool) software (BMC Bioinformatics. 2003 4:29. MatGAT: an application that generates similarity/identity matrices using protein or DNA sequences. Campanella J J, Bitincka L, Smalley J; software hosted by Ledion Bitincka). MatGAT software generates similarity/identity matrices for DNA or protein sequences without needing pre-alignment of the data. The program performs a series of pair-wise alignments using the Myers and Miller global alignment algorithm (with a gap opening penalty of 11, and a gap extension penalty of 1), calculates similarity and identity using for example Blosum 62 (for polypeptides), and then places the results in a distance matrix. Sequence similarity is shown in the bottom half of the dividing line and sequence identity is shown in the top half of the diagonal dividing line. The sequence of SEQ ID NO: 2 is indicated as number 1 in the matrix.

The kinase domains of the Ste20-like proteins were delineated using the SMART tool and the obtained sequences are listed in Table 3.

TABLE 3 list of the kinase domains in the various SEQ ID Nos:

SEQ ID NO: 2  YEIICKIGVGVSASVYKAICIPMNSMVVAIKAIDLDQ
SRADFDSLRRETKTMSLLSHPNILNAYCSFTVDRCLW
VVMPFMSCGSLHSIVSSSFPSGLPENCISVFLKETLN
AISYLHDQGHLHRDIKAGNILVDSDGSVKLADFGVSA
SIYEPVTSSSGTTSSSLRLTDIAGTPYWMAPEVVHSH
TGYGFKADIWSFGITALELAHGRPPLSHLPPLKSLLM
KITKRFHFSDYEINTSGSSKKGNKKFSKAFREHVGLC
LEQDPTKRPSAEKLLKHPFF

SEQ ID NO: 12  YKLYEEIGDGVSATVYHRALCIPLNVVVAIKVLDLEKC
NNDLDGIRREVQTMSLINHPNVLQAHCSFTTGHQLWV
VMPYMAGGSCLHIIKSSYPDGFEEPVIATLLRETLKA
LVYLHAHGHIHRDVKAGNILLDSNGAVKLADFGVSAC
MFDTGDRQRSRNTFVGTPCWMAPEVMQQLHGYDFKAD
VWSFGITALELAHGHAPFSKYFPMKVLLMTLQNAPPG
LDYERDKRFSKAFKEMVGTCLVKDPKKRPTSEKLLKH
PFF

SEQ ID NO: 14  YELFEEVGEGVSATVYRARCIALNEIVAVKILDLEKC
RNDLETIRKEVHIMSLIDHPNLLKAHCSFIDSSSLWI
VMPYMSGGSCFHLMKSVYPEGLEQPIIATLLREVLKA
LVYLHRQGHIHRDVKAGNILIHSKGVVKLGDFGVSAC
MFDSGERMQTRNTFVGTPCWMAPEVMQQLDGYDFKYL
AHGHAPFSKYPPMKVLLMTLQNAPPRLDYDRDKKFSK
SFRELIAACLVKDPKKRPTAAKLLKHPFF

SEQ ID NO: 16  YEILEEIGDGVYRARCILLDEIVAIKIWNLEKCTNDL
ETIRKEVHRLSLIDHPNLLRVHCSFIDSSSLWIVMPF
MSCGSSLNIMKSVYPNGLEEPVIAILLREILKALVYL
HGLGHIHRNVKAGNVLVDSEGTVKLGDFEVSASMFDS
VERMRTSSENTFVGNPRRMAPEKDMQQVDGYDFKVDI
WSFGMTALELAHGHSPTTVLPLNLQNSPFPNYEEDTK
FSKSFRELVAACLIEDPEKRPTASQLLEYPFL

SEQ ID NO: 18  YTLYEFIGQGVSALVHRALCIPFDEVVAIKILDFERD
NCDLNNISREAQTMMLVDHPNVLKSHCSFVSDHNLWV
IMPYMSGGSCLHILKAAYPDGFEEAIIATILREALKG
LDYLHQHGHIHRDVKAGNILLGARGAVKLGDFGVSAC
LFDSGDRQRTRNTFVGTPCWMAPEVMEQHGYDFKAD
IWSFGITGLELAHGHAPFSKYPPMKVLLMTLQNAPPG
LDYERDKKFSRSFKQMIASCLVKDPSKRPSAKKLLKH
SFF

SEQ ID NO: 20  YKLMEEVGYGASAVVHRAIYLPTNEVVAIKSLDLRC
NSNLDDIRREAQTMTLIDHPNVIKSFCSFAVDHHLWV
VMPFMAQGSCLHLMKAAYPDGFEEAAICSMLKETLKA
LDYLHRQGHIHRDVKAGNILLDDTGEIKLGDFGVSAC
LFDNGDRQRARNTFVGTPCWMAPEVLQPGSGYNSKAD
IWSFGITALELAHGHAPFSKYPPMKVLLMTIQNAPPG
LDYDRDKKFSKSFKELVALCLVKDQTKRPTAEKLLKH
SFF

SEQ ID NO: 22  YKLMEEIGHGASAVVYRAIYLPTNEVVAIKCLDLRC
NSNLDDIRRESQTMSLIDHPNVIKSFCSFSVDHSLWV
VMPFMAQGSCLHLMKTAYSDGFEESAICCVLKETLKA
LDYLHRQGHIHRDVKAGNILLDDNGEIKLGDFGVSAC
LFDNGDRQRARNTFVGTPCWMAPEVLQPGNGYNSKAD
IWSFGITALELAHGHAPFSKYPPMKVLLMTIQNAPPG
LDYDRDKKFSKSFKEMVAMCLVKDQTKRPTAEKLLKH
SCF

SEQ ID NO: 24  YRLLCKIGSGVSAVVYKAACVPLGSAVVAIKAIDLER
SRANLDEVWREAKAMALLSHRNVLRAHCSFTVGSHLW
VVMPFMAAGSLHSILSHGFPDGLPEQCIAVVLRDTLR
ALCYLHEQGRIHRDIKAGNILVDSDGSVKLADFGVSA
SIYETAPSTSSAFSGPINHAPPPSGAALSSSCFNDMA

TABLE 3-continued list of the kinase domains in the various SEQ ID Nos:

GTPYWMAPEVIHSHVGYGIKADIWSFGITALELAHGR
PPLSHLPPSKSMLMRITSRVRLEVDASSSSSEGSSSA
ARKKKKFSKAFKDMVSSCLCQEPAKRPSAEKLLRHPF
F

SEQ ID NO: 26  YKLCEEVGDGVSATVYKALCIPLNIEVAIKVLDLEKC
SNDLDGIRREVQTMSLIDHPNLLRAYCSFTNGHQLWV
IMPYMAAGSALHIMKTSFPDGFEEPVIATLLREVLKA
LVYLHSQGHIHRDVKAGNILIDTNGAVKLGDFGVSAC
MFDTGNRQRARNTFVGTPCWMAPEVMQQLHGYDYKAD
IWSFGITALELAHGHAPFSKYPPMKVLLMTLQNAPPG
LDYERDKRFSKSFKDLVATCLVKDPRKRPSSEKLLKH
SFF

SEQ ID NO: 28  YELYEEIGQGVSAIVYRSLCKPLDEIVAVKVLDFERT
NSDLWLVVMQVGYTRIVAIYVPPLDLSKMIVTRICLT
QNNIMREAQTMILIDQPNVMKAHCSFTNNHSLWVVMP
YMAGGSCLHIMKSVYPDGFEEAVIATVLREVLKGLEY
LHHHGHIHRDVKAGNILVDSRGVVKLGDFGVSACLFD
SGDRQRARNTFVGTPCWMAPEVMEQLHGYDFKADIWS
FGITALELAHGHAPFSKFPPMKVLLMTLQNAPPGLDY
ERDKKFSRHFKQMVAMCLVKDPSKRPTAKKLLKQPFF

SEQ ID NO: 30  YQLMEEVGYGAHAVVYRALFVPRNDVVAVKCLDLDQL
NNNIDEIQREAQIMSLIEHPNVIRAYCSFVVEHSLWV
VMPFMTEGSCLHLMKIAYPDGFEEPVIGSILKETLKA
LEYLHRQGQIHRDVKAGNILVDNAGIVKLGDFGVSAC
MFDRGDRQRSRNTFVGTPCWMAPEVLQPGTGYNFKAD
IWSFGITALELAHGHAPFSKYPPMKVLLMTLQNAPPG
LDYDRDRRFSKSFKEMVAMCLVKDQTKRPTAEKLLKH
SFF

SEQ ID NO: 32  YRLLEEVGYGANAVVYRAVFLPSNRTVAVKCLDLDRV
NSNLDDIRKEAQTMSLIDHPNVIRAYCSFVVDHNLWV
IMPFMSEGSCLHLMKVAYPDGFEEPVIASILKETLKA
LEYLHRQGHIHRDVKRNIIQAGNILMDSPGIVKLGDF
GVSACMFDRGDRQRSRNTFVGTPCWMAPEVLQPGAGY
NFKKYVSNHLFTNLIWLFKISLRGKNSNYHKNTGNKV
LLMTLQNAPPGLDYDRDKRFSKSFKEMVAMCLVKDQT
KRPTAEKLLKHSFF

SEQ ID NO: 34  YKIVDEIGAGNSAVVYKAICIPINSTPVAIKSIDLDR
SRPDLDDVRREAKTLSLLSHPNILKAHCSFTVDNRLW
VVMPFMAGGSLQSIISHSFQNGLTEQSIAVILKDTLN
ALSYLHGQGHLHRDIKSGNILVDSNGLVKLADFGVSA
SIYESNNSVGACSSYSSSSSSSNSSSHIFTDFAGTPYW
MAPEVIHSHNGYSFKADIWSFGITALELAHGRPPLSH
LPPSKSLMLNITKRFKFSDFDKHSYKGHGGSNKFSKA
FKDMVALCLNQDPTKRPSAEKLLKHSFF

Results of the MATGAT analysis are shown in Table 4 for the full-length sequences and in Table 5 for the kinase domains of the Ste20-like polypeptides. Percentage identity is given above the diagonal (in bold) and percentage similarity is given below the diagonal (normal font). Percentage identity between kinase domains of Ste20-like paralogues and orthologues of SEQ ID NO: 2 ranges between 44% (for SEQ ID NO: 28) and 71% (for SEQ ID NO: 34).

TABLE 4

Sequence similarity\identity for the full-length sequences

| | 1 | 2 | 3 | 4 | 5 | 6 | 7 | 8 | 9 | 10 | 11 | 12 | 13 |
|---|---|---|---|---|---|---|---|---|---|---|---|---|---|
| 1. SEQIDNO2 | | 30.7 | 30.2 | 32.6 | 29.3 | 28.8 | 28.9 | 46.5 | 29.0 | 26.8 | 35.5 | 28.9 | 53.5 |
| 2. SEQIDNO12 | 45.8 | | 45.3 | 33.9 | 45.2 | 42.8 | 43.1 | 28.6 | 55.1 | 42.7 | 41.5 | 38.3 | 32.3 |
| 3. SEQIDNO14 | 48.3 | 62.3 | | 41.2 | 39.6 | 37.9 | 38.7 | 28.1 | 44.3 | 37.2 | 40.3 | 35.7 | 30.1 |
| 4. SEQIDNO16 | 55.2 | 48.1 | 56.4 | | 28.9 | 27.4 | 27.8 | 30.7 | 33.7 | 29.2 | 35.8 | 30.1 | 32.8 |
| 5. SEQIDNO18 | 43.9 | 63.4 | 56.8 | 43.7 | | 41.5 | 40.5 | 27.1 | 42.3 | 48.9 | 37.9 | 36.4 | 28.7 |
| 6. SEQIDNO20 | 42.1 | 61.2 | 53.8 | 41.9 | 61.4 | | 73.9 | 26.8 | 41.2 | 40.2 | 45.2 | 47.7 | 29.8 |
| 7. SEQIDNO22 | 42.3 | 60.8 | 53.2 | 41.9 | 60.8 | 84.9 | | 25.7 | 41.2 | 39.7 | 44.1 | 48.5 | 29.2 |
| 8. SEQIDNO24 | 59.9 | 43.9 | 48.1 | 47.8 | 41.6 | 42.7 | 41.9 | | 28.3 | 26.3 | 32.2 | 26.9 | 47.1 |
| 9. SEQIDNO26 | 44.2 | 72.4 | 58.2 | 47.5 | 62.8 | 61.0 | 60.4 | 44.3 | | 41.1 | 39.8 | 35.9 | 29.2 |
| 10. SEQIDNO28 | 39.3 | 57.7 | 51.5 | 41.7 | 64.9 | 58.6 | 56.4 | 39.3 | 58.6 | | 36.8 | 34.2 | 25.9 |
| 11. SEQIDNO30 | 51.6 | 54.5 | 58.1 | 52.5 | 52.2 | 57.5 | 56.4 | 50.8 | 52.4 | 49.4 | | 48.0 | 33.0 |
| 12. SEQIDNO32 | 42.8 | 54.9 | 51.8 | 42.9 | 53.9 | 64.1 | 63.0 | 43.9 | 54.5 | 51.1 | 60.9 | | 29.3 |
| 13. SEQIDNO34 | 69.3 | 48.2 | 50.5 | 53.9 | 44.8 | 44.6 | 45.3 | 63.5 | 45.0 | 41.5 | 53.4 | 48.2 | |

TABLE 5

Sequence similarity\identity for the kinase domain sequences of Table 3

| | 1 | 2 | 3 | 4 | 5 | 6 | 7 | 8 | 9 | 10 | 11 | 12 | 13 |
|---|---|---|---|---|---|---|---|---|---|---|---|---|---|
| 1. SEQIDNO2 | | 54.5 | 46.6 | 46.5 | 48.7 | 50.9 | 51.3 | 66.0 | 52.3 | 44.1 | 51.3 | 43.4 | 70.8 |
| 2. SEQIDNO12 | 69.9 | | 72.5 | 60.5 | 77.5 | 74.0 | 74.4 | 50.2 | 86.6 | 70.3 | 74.4 | 64.5 | 52.3 |
| 3. SEQIDNO14 | 62.4 | 84.7 | | 65.8 | 67.6 | 64.9 | 64.5 | 41.9 | 72.1 | 61.8 | 65.3 | 60.1 | 43.2 |
| 4. SEQIDNO16 | 65.2 | 77.9 | 82.3 | | 54.5 | 52.3 | 52.6 | 40.9 | 59.8 | 51.3 | 53.8 | 49.1 | 44.8 |
| 5. SEQIDNO18 | 65.2 | 89.3 | 81.7 | 73.3 | | 73.7 | 72.1 | 45.8 | 74.4 | 73.3 | 69.1 | 61.6 | 47.7 |
| 6. SEQIDNO20 | 67.4 | 86.3 | 78.2 | 72.9 | 87.0 | | 93.1 | 47.0 | 73.3 | 63.9 | 81.3 | 72.5 | 51.9 |
| 7. SEQIDNO22 | 67.4 | 86.3 | 77.9 | 72.9 | 85.9 | 97.3 | | 47.0 | 73.3 | 64.5 | 81.3 | 72.1 | 52.6 |
| 8. SEQIDNO24 | 77.1 | 64.6 | 59.3 | 58.9 | 60.9 | 62.3 | 62.0 | | 49.2 | 43.2 | 47.0 | 39.9 | 64.4 |
| 9. SEQIDNO26 | 68.5 | 96.2 | 84.0 | 78.6 | 87.0 | 86.6 | 87.0 | 64.0 | | 67.2 | 73.3 | 64.1 | 51.6 |
| 10. SEQIDNO28 | 62.8 | 79.1 | 73.0 | 66.2 | 81.8 | 76.7 | 76.7 | 61.3 | 78.0 | | 63.2 | 55.5 | 43.0 |
| 11. SEQIDNO30 | 66.3 | 85.5 | 80.2 | 74.0 | 86.3 | 93.5 | 92.7 | 62.0 | 85.9 | 75.7 | | 77.2 | 49.1 |
| 12. SEQIDNO32 | 62.0 | 78.0 | 72.9 | 66.7 | 78.8 | 85.0 | 83.9 | 57.9 | 78.8 | 71.6 | 87.2 | | 44.4 |
| 13. SEQIDNO34 | 80.5 | 69.0 | 61.3 | 64.5 | 65.9 | 69.3 | 69.3 | 76.4 | 68.6 | 64.9 | 67.9 | 66.2 | |

Example 2

Gene Cloning of Ste20-Like

The *Arabidopsis thaliana* Ste20-like gene was amplified by PCR using as template an *Arabidopsis thaliana* seedling cDNA library (Invtrogen, Paisley, UK). After reverse transcription of RNA extracted from seedlings, the cDNAs were cloned into pCMV Sport 6.0. Average insert size of the bank was 1.5 kb and the original number of clones was of the order of $1.59 \times 10^7$ cfu. Original titer was determined to be $9.6 \times 10^5$ cfu/ml after first amplification of $6 \times 10^{11}$ cfu/ml. After plasmid extraction, 200 ng of template was used in a 50 µl PCR mix. Primers prm03186 (SEQ ID NO: 3; sense, start codon in bold, AttB1 site in italic: 5'-ggggacaagtttgtacaaaaaagcag-gcttcacaatggctcggaacaagctc 3') and prm03187 (SEQ ID NO: 4; reverse, complementary, AttB2 site in italic: 5' ggggac-cactttgtacaagaaagctgggtaatagttaacccaaaacactatcttta 3'), which include the AttB sites for Gateway recombination, were used for PCR amplification. PCR was performed using Hifi Taq DNA polymerase in standard conditions. A PCR fragment of 1532 bp (including attB sites) was amplified and purified also using standard methods. The first step of the Gateway procedure, the BP reaction, was then performed, during which the PCR fragment recombines in vivo with the pDONR201 plasmid to produce, according to the Gateway terminology, an "entry done", p068. Plasmid pDONR201 was purchased from Invitrogen, as part of the Gateway® technology.

Example 3

Vector Construction

The entry done p068 were subsequently used in an LR reaction with p00640, a destination vector used for *Oryza sativa* transformation. This vector contains as functional elements within the T-DNA borders: a plant selectable marker; a screenable marker expression cassette; and a Gateway cassette intended for LR in vivo recombination with the sequence of interest already doned in the entry done. A rice GOS2 promoter (nucleotides 1 to 2193 of SEQ ID NO: 5) for constitutive expression (PRO0129) was located upstream of this Gateway cassette.

Figure 2:
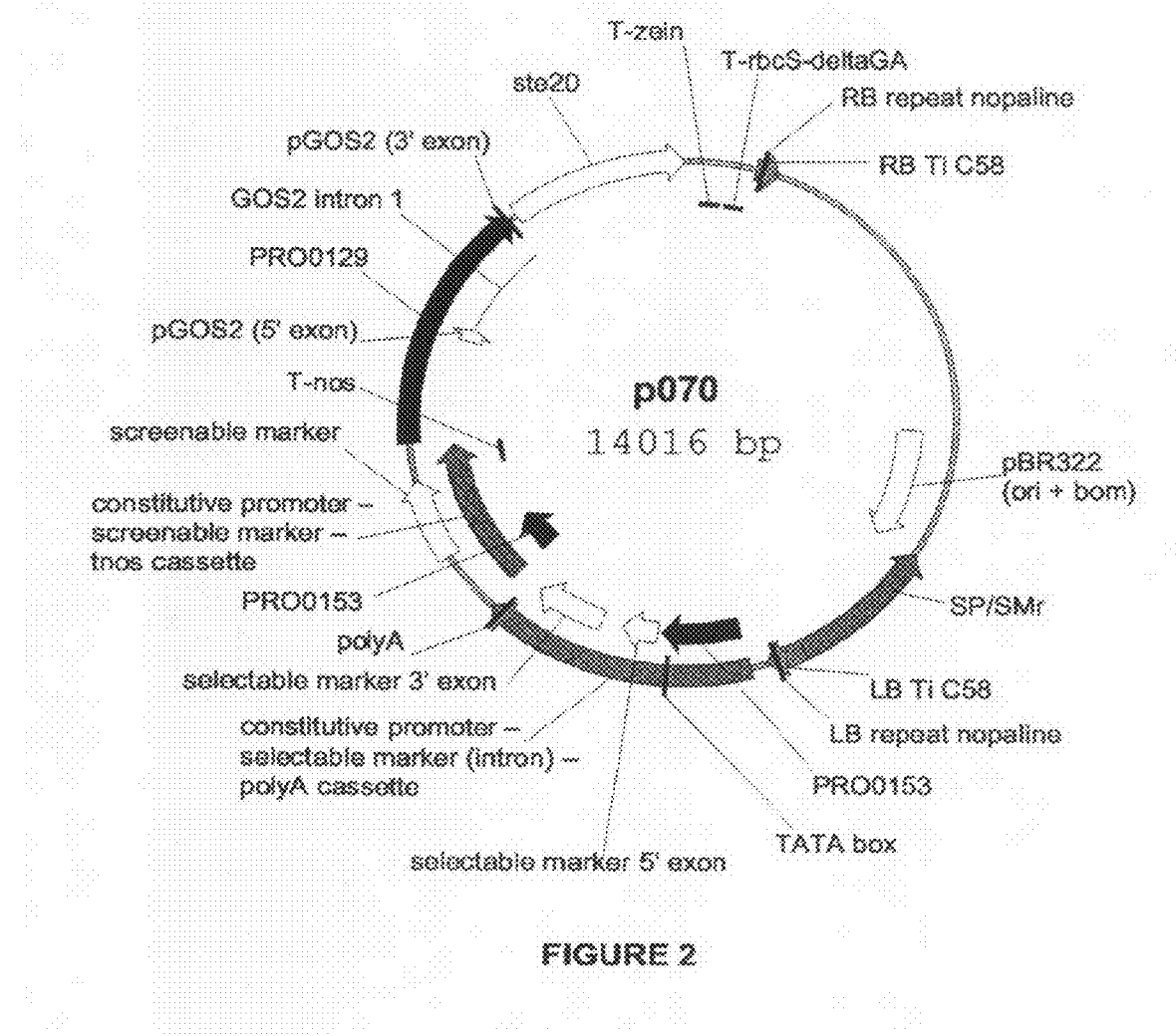
FIG. 2 shows a binary vector p070, for expression in *Oryza sativa* of an *Arabidopsis thaliana* Ste20-like coding sequence under the control of a GOS2 promoter (internal reference PRO0129).

After the LR recombination step, the resulting expression vector, p070 for Ste20-like (FIG. 2) was transformed into *Agrobacterium* strain LBA4044 and subsequently to *Oryza sativa* plants. Transformed rice plants were allowed to grow and were then examined for the parameters described in Example 4.

Example 4

Evaluation and Results of Step 20-Like Under the Control of the Rice GOS2 Promoter Approximately 15 to 20 independent T0 rice transformants were generated. The primary transformants were transferred from a tissue culture chamber to a greenhouse for growing and harvest of T1 seed. Five events, of which the T1 progeny segregated 3:1 for presence/absence of the transgene, were retained. For each of these events, approximately 10 T1 seedlings containing the transgene (hetero- and homo-zygotes) and approximately 10 T1 seedlings lacking the transgene (nullizygotes) were selected by monitoring visual marker expression. The selected T1 plants were transferred to a greenhouse. Each plant received a unique barcode label to link unambiguously the phenotyping data to the corresponding plant. The selected T1 plants were grown on soil in 10 cm diameter pots under the following environmental settings: photoperiod=11.5 h, daylight intensity=30,000 lux or more, daytime temperature=28° C., night time temperature=22° C., relative humidity=60-70%. Transgenic plants and the corresponding nullizygotes were grown side-by-side at random positions. From the stage of sowing until the stage of maturity the plants were passed several times through a digital imaging cabinet. At each time point digital images (2048×1536 pixels, 16 million colours) were taken of each plant from at least 6 different angles.

The mature primary panicles were harvested, bagged, barcode-labelled and then dried for three days in the oven at 37° C. The panicles were then threshed and all the seeds collected. The filled husks were separated from the empty ones using an air-blowing device. After separation, both seed lots were then counted using a commercially available counting machine. The empty husks were discarded. The filled husks were weighed on an analytical balance and the cross-sectional area of the seeds was measured using digital imaging. This procedure resulted in the set of the following seed-related parameters:

The number of filled seeds was determined by counting the number of filled husks that remained after the separation step. The total seed yield was measured by weighing all filled husks harvested from a plant. Total seed number per plant was measured by counting the number of husks harvested from a plant. Thousand Kernel Weight (TKW) is extrapolated from the number of filled seeds counted and their total weight. Harvest index is defined as the ratio between the total seed weight and the above-ground area ($mm^2$), multiplied by a factor $10^6$. These parameters were derived in an automated way from the digital images using image analysis software and were analysed statistically. Individual seed parameters (including width, length, area, weight) were measured using a custom-made device consisting of two main components, a weighing and imaging device, coupled to software for image analysis.

A two factor ANOVA (analyses of variance) corrected for the unbalanced design was used as statistical model for the overall evaluation of plant phenotypic characteristics. An F-test was carried out on all the parameters measured of all the plants of all the events transformed with that gene. The F-test was carried out to check for an effect of the gene over all the transformation events and to verify for an overall effect of the gene, also named herein "global gene effect". If the value of the F test shows that the data are significant, than it is concluded that there is a "gene" effect, meaning that not only presence or the position of the gene is causing the effect. The threshold for significance for a true global gene effect is set at 5% probability level for the F test.

To check for an effect of the genes within an event, i.e., for a line-specific effect, a t-test was performed within each event using data sets from the transgenic plants and the corresponding null plants. "Null plants" or "null segregants" or "nullizygotes" are the plants treated in the same way as the transgenic plant, but from which the transgene has segregated. Null plants can also be described as the homozygous negative transformed plants. The threshold for significance for the t-test is set at 10% probability level. The results for some events can be above or below this threshold. This is based on the hypothesis that a gene might only have an effect in certain positions in the genome, and that the occurrence of this position-dependent effect is not uncommon. This kind of gene effect is also named herein a "line effect of the gene". The p-value is obtained by comparing the t-value to the t-distribution or alternatively, by comparing the F-value to the F-distribution. The p-value then gives the probability that the null hypothesis (i.e., that there is no effect of the transgene) is correct.

The data obtained for Ste20 in the first experiment were confirmed in a second experiment with T2 plants. Four lines that had the correct expression pattern were selected for further analysis. Seed batches from the positive plants (both hetero- and homozygotes) in T1, were screened by monitoring marker expression. For each chosen event, the heterozygote seed batches were then retained for T2 evaluation. Within each seed batch an equal number of positive and negative plants were grown in the greenhouse for evaluation.

A total number of 120 Ste20 transformed plants were evaluated in the T2 generation, that is 30 plants per event of which 15 positives for the transgene, and 15 negatives.

Because two experiments with overlapping events had been carried out, a combined analysis was performed. This is useful to check consistency of the effects over the two experiments, and if this is the case, to accumulate evidence from both experiments in order to increase confidence in the conclusion. The method used was a mixed-model approach that takes into account the multilevel structure of the data (i.e. experiment-event-segregants). P-values are obtained by comparing likelihood ratio test to chi square distributions.

Example 5

Evaluation of Ste20 Transformants: Measurement of Yield-Related Parameters

Upon analysis of the seeds as described above, the inventors found that plants transformed with the Ste20 gene construct had a higher seed yield, expressed as number of filled seeds, total weight of seeds and harvest index, compared to plants lacking the Ste20 transgene. The results obtained for plants in the T1 generation are summarised in Table 6:

TABLE 6

|  | % difference | p-value |
|---|---|---|
| Nr filled seeds | +38 | 0.0003 |
| Total weight seeds | +38 | 0.0004 |
| Harvest Index | +42 | 0.0001 |

These positive results were again obtained in the T2 generation. In Table 7, data show the overall % increases for the number of filled seeds, total weight of seeds and harvest index, calculated from the data of the individual lines of the T2 generation, and the respective p-values. These T2 data were re-evaluated in a combined analysis with the results for the T1 generation, and the obtained p-values show that the observed effects were highly significant.

TABLE 7

|  | T2 generation | | Combined analysis |
|---|---|---|---|
|  | % difference | p-value | p-value |
| Nr filled seeds | +30 | 0.0004 | 0.0000 |
| Total weight seeds | +29 | 0.0008 | 0.0000 |
| Harvest Index | +33 | 0.0001 | 0.0000 |

The invention claimed is:

1. A method for increasing plant seed yield relative to control plants, comprising introducing and expressing in a plant a Ste20-like nucleic acid or a variant thereof; and selecting a plant having increased seed yield compared to a control plant, wherein said Ste20-like nucleic acid or variant thereof encodes a polypeptide comprising the sequence of SEQ ID NO: 2 or a sequence having at least 95% sequence identity to the sequence of SEQ ID NO: 2 and wherein said Ste20-like nucleic acid or variant thereof is operably linked to a constitutive promoter.

2. The method according to claim 1, wherein said Ste20-like nucleic acid or variant thereof is overexpressed in a plant.

3. The method according to claim 1, wherein said Ste20-like nucleic acid or variant thereof is of plant origin.

4. The method according to claim 1, wherein said constitutive promoter is a GOS2 promoter.

5. The method according to claim 1, wherein said increased yield is selected from: increased total weight of seeds, increased number of filled seeds or increased harvest index.

6. A plant obtained by the method according to claim 1.

7. A method for the production of a transgenic plant having increased seed yield, which method comprises:
(i) introducing and expressing in a plant or plant cell a Ste20-like nucleic acid or variant thereof;
(ii) cultivating the plant cell under conditions promoting plant growth and development; and
(iii) selecting a plant having increased seed yield compared to a control plant, wherein said Ste20-like nucleic acid or variant thereof encodes a polypeptide comprising the sequence of SEQ ID NO: 2 or a sequence having at least 95% sequence identity to the sequence of SEQ ID NO: 2 and wherein said Ste20-like nucleic acid or variant thereof is operably linked to a constitutive promoter.

8. The method according to claim 7, wherein said variant is a portion of a Ste20-like nucleic acid or a sequence capable of hybridizing to a Ste20-like nucleic acid, which portion or hybridizing sequence encodes a polypeptide comprising a kinase domain and the Ste20 signature sequence of SEQ ID NO: 6.

9. A transgenic plant having increased seed yield compared to a control plant, which plant comprises a construct comprising a GOS2 promoter and a Ste20-like nucleic acid or a variant thereof, wherein said Ste20-like nucleic acid or variant thereof encodes a polypeptide comprising the sequence of SEQ ID NO: 2 or a sequence having at least 95% sequence identity to the sequence of SEQ ID NO: 2.

10. The transgenic plant according to claim 6, wherein said plant is a monocotyledonous plant.

11. Harvestable parts of the plant according to claim 6, wherein said harvestable parts comprise the nucleic acid.

12. Harvestable parts of a plant according to claim 11 wherein said harvestable parts are seeds.

13. A product directly derived from the plant according to claim 10 and/or from harvestable parts therefrom, wherein the product comprises the nucleic acid.

14. The method according to claim 1, wherein said Ste20-like nucleic acid or variant thereof is from a dicotyledonous plant.

15. The method according to claim 1, wherein said Ste20-like nucleic acid or variant thereof is from the family Brassicaceae.

16. The method according to claim 1, wherein said Ste20-like nucleic acid or variant thereof is from *Arabidopsis thaliana*.

17. The transgenic plant according to claim 7, wherein said plant is selected from the group consisting of sugar cane, rice, maize, wheat, barley, millet, rye, oats, and sorghum.

18. The transgenic plant according to claim 9, wherein said plant is a monocotyledonous plant.

19. Harvestable parts of the plant according to claim 9, wherein said harvestable parts comprise the nucleic acid.

20. Harvestable parts of a plant according to claim 19, wherein said harvestable parts are seeds.

21. A product directly derived from the plant according to claim 9, and/or from harvestable parts therefrom, wherein the product comprises the nucleic acid.

22. The transgenic plant according to claim 9, wherein said plant is selected from the group consisting of sugar cane, rice, maize, wheat, barley, millet, rye, oats, and sorghum.

* * * * *

UNITED STATES PATENT AND TRADEMARK OFFICE
CERTIFICATE OF CORRECTION

| | | |
|---|---|---|
| PATENT NO. | : 8,119,858 B2 | Page 1 of 1 |
| APPLICATION NO. | : 11/988254 | |
| DATED | : February 21, 2012 | |
| INVENTOR(S) | : Christophe Reuzeau et al. | |

It is certified that error appears in the above-identified patent and that said Letters Patent is hereby corrected as shown below:

In Claim 17, in column 114, on line 50, "17. The transgenic plant according to claim 7, wherein said" should read -- 17. The transgenic plant according to claim 6, wherein said --

Signed and Sealed this
Fourteenth Day of August, 2012

David J. Kappos
*Director of the United States Patent and Trademark Office*